(12) United States Patent
Shi et al.

(10) Patent No.: US 8,198,039 B2
(45) Date of Patent: Jun. 12, 2012

(54) BIOSENSORS AND RELATED METHODS

(75) Inventors: Haibin Shi, Pittsburgh, PA (US); Joanne I. Yeh, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 252 days.

(21) Appl. No.: 12/204,407

(22) Filed: Sep. 4, 2008

(65) Prior Publication Data

US 2009/0061451 A1 Mar. 5, 2009

Related U.S. Application Data

(60) Provisional application No. 60/969,864, filed on Sep. 4, 2007.

(51) Int. Cl.
*C12Q 1/68* (2006.01)

(52) U.S. Cl. ........ 435/7.9; 435/7.1; 435/6.1; 435/283.1; 435/287.1; 435/287.2; 422/68.1; 422/82.01; 436/518; 436/532; 436/86

(58) Field of Classification Search .................. 436/518, 436/532, 86; 435/6, 7.1, 7.9, 283.1, 287.1, 435/287.2; 422/68.1, 82.01
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 5,556,524 A * | 9/1996 | Albers | 204/403.06 |
| 5,840,867 A | 11/1998 | Toole et al. | |
| 6,060,327 A * | 5/2000 | Keen | 506/9 |
| 6,063,569 A | 5/2000 | Gildea et al. | |
| 6,083,758 A | 7/2000 | Imperiali et al. | |
| 6,133,444 A | 10/2000 | Coull et al. | |
| 6,172,226 B1 | 1/2001 | Coull et al. | |
| 6,391,558 B1 * | 5/2002 | Henkens et al. | 435/6 |
| 6,544,776 B1 | 4/2003 | Gold et al. | |
| 7,045,285 B1 | 5/2006 | Kayyem et al. | |
| 7,179,896 B2 | 2/2007 | Kim et al. | |
| 7,211,668 B2 | 5/2007 | Kim et al. | |
| 7,511,142 B2 * | 3/2009 | Xie et al. | 546/2 |
| 7,563,588 B2 * | 7/2009 | Gao et al. | 435/14 |
| 2002/0058273 A1 * | 5/2002 | Shipwash | 435/6 |
| 2004/0005582 A1 * | 1/2004 | Shipwash | 435/6 |
| 2004/0053425 A1 | 3/2004 | Link et al. | |
| 2004/0067541 A1 | 4/2004 | Dwek et al. | |
| 2005/0196820 A1 | 9/2005 | Zweig | |
| 2007/0202559 A1 * | 8/2007 | Hasenbank et al. | 435/11 |
| 2007/0272294 A1 * | 11/2007 | Long et al. | 136/244 |

OTHER PUBLICATIONS

Crosslinking Reagents: Technical Handbook, No. 1601361, Mar. 2006, Pierce Biotechnology, Inc., Rockford, Illinois.
Fernández-Sánchez C, McNeil CJ, Rawson K, Nilsson O: Disposable noncompetitive immunosensor for free and total prostate-specific antigen based on capacitance measurement. Anal. Chem. 76 (2004), 5649-5656.
Okuno J, Maehashi K, Kerman K et al: Label-free immunosensor for prostate-specific antigen based on single-walled carbon nanotube array-modified microelectrodes. Biosen. Bioelectron. 2007, 22, 2377-2381.

(Continued)

*Primary Examiner* — Melanie J Yu
(74) *Attorney, Agent, or Firm* — The Webb Law Firm

(57) ABSTRACT

Provided herein are biosensors that comprise a biological signal source linked to a substrate by a peptide nucleic acid spacer and methods of use of the biosensor. In one embodiment, the biosensor is used to detect prostate-specific antigen.

25 Claims, 21 Drawing Sheets

OTHER PUBLICATIONS

Popescu, D.; Parolin, T.; Achim, C., Metal Ion Incorporation in PNA Duplexes, J. Am. Chem. Soc. 2003 ; 125 (21); 6354-6355.

Sarkar P, Pal PS, Ghosh D et al: Amperometric biosensors for detection of the prostate cancer marker (PSA). International Journal Pharmaceutics. 2002, 238, 1-9.

Sato K, Hosokawa K, Maeda M. Rapid aggregation of gold nanoparticles induced by non-cross-linking DNA hybridization. J Am Chem Soc. Jul. 9, 2003;125(27):8102-3.

Segond von Banchet G, Heppelmann B. Non-radioactive localization of substance P binding sites in rat brain and spinal cord using peptides labeled with 1.4-nm gold particles. J Histochem Cytochem. Aug. 1995;43(8):821-7.

Shim, M., Kam, N., Chen, R., Li, Y., Dai, H., 2002. Nano Lett. 2, Shim M, Shi Kam NW, Chen RJ, Li Y, Dai H. Functionalization of Carbon Nanotubes for Biocompatibility and Biomolecular Recognition. Nano Lett. 2002;2(4):285-8.

Song YH, Liu YQ, Yang ML, Zhang BL, Li Z. Diluting thiol-derivatized oligonucleotide monolayers on Au(1 1 1) by mercaptohexanol replacement reaction . Appl Surf Sci. Jun. 2006;252(16):5693-9.

Sotiropoulou S, Chaniotakis NA. Carbon nanotube array-based biosensor. Anal Bioanal Chem. Jan. 2003;375(1):103-5. Epub Oct. 31, 2002.

Taft BJ, Lazareck AD, Withey GD, Yin A, Xu JM, Kelley SO. Site-specific assembly of DNA and appended cargo on arrayed carbon nanotubes. J Am Chem Soc. Oct. 13, 2004;126(40):12750-1.

Tsang SC, Chen YK, Harris PJF, Green MLH. A simple chemical method of opening and filling carbon nanotubes. Nature. Nov. 2002;372(6502):159-62.

Ugo P, Pepe N, Moretto LM, Battagliarin M. Direct voltammetry of cytochrome c at trace concentrations with nanoelectrode ensembles. J. Electroanal. Chem. 2003, 560, 51-58.

Wang J, Scampicchio M, Laocharoensuk R, Valentini F, Gonzalez-García O, Burdick J. Magnetic tuning of the electrochemical reactivity through controlled surface orientation of catalytic nanowires. J Am Chem Soc. Apr. 12, 2006;128(14):4562-3.

Wang L, Reipa V, Blasic J. Silicon Nanoparticles as a Luminescent Label to DNA. Bioconjugate Chem. 2004;15(2):409-12.

Wang SG, Zhang Q, Wang R, Yoon SF. A novel multi-walled carbon nanotube-based biosensor for glucose detection. Biochem Biophys Res Commun. Nov. 21, 2003;311(3):572-6.

Wang SG, Zhang Q, Wang R, Yoon SF, Ahn J, Yang DJ, Tian JZ, Li JQ, Zhou Q. Multi-walled carbon nanotubes for the immobilization of enzyme in glucose biosensors. Electrochem Commun. Sep. 2003;5(9):800-3.

Wang C, Liu Q, Shao X, Yang G, Xue H, Hu X. One step fabrication of nanoelectrode ensembles formed via amphiphilic block copolymers self-assembly and selective voltammetric detection of uric acid in the presence of high ascorbic acid content. Talanta. Jan. 15, 2007;71(1):178-85. Epub May 9, 2006.

Watson, R.M.; Skorik, Y.; Patra, G.K.; Achim, C., Influence of Metal Coordination on the Mismatch Tolerance of Ligand-Modified PNA Duplexes, J. Am. Chem. Soc. 2005, 127(18), 14628-14639.

Weizmann Y, Patolsky F, Katz E, Willner I. Amplified DNA sensing and immunosensing by the rotation of functional magnetic particles. J Am Chem Soc. Mar. 26, 2003;125(12):3452-4.

Weizmann Y, Elnathan R, Lioubashevski O, Willner I. Endonuclease-based logic gates and sensors using magnetic force-amplified readout of DNA scission on cantilevers. J Am Chem Soc. Sep. 14, 2005;127(36):12666-72.

Withey GD, Lazareck AD, Tzolov MB, Yin A, Aich P, Yeh JI, Xu J. Ultra-high redox enzyme signal transduction using highly ordered carbon nanotube array electrodes. Biosens Bioelectron. Feb. 2006;21(8):1560-5.

Xia T, Kovochich M, Brant J, Hotze M, Sempf J, Oberley T, Sioutas C, Yeh JI, Wiesner MR, Nel AE. Comparison of the abilities of ambient and manufactured nanoparticles to induce cellular toxicity according to an oxidative stress paradigm. Nano Lett. Aug. 2006;6(8):1794-807.

Xian Y, Hu Y, Liu F, Xian Y, Feng L, Jin L. Template synthesis of highly ordered Prussian blue array and its application to the glucose biosensing. Biosens Bioelectron. Jun. 2007;22(12):2827-33.

Xiao Y, Patolsky F, Katz E, Hainfeld JF, Willner I. Plugging into enzymes: nanowiring of redox enzymes by a gold nanoparticle. Science. Mar. 2003;299(5614):1877-81.

Xiao S, Liu F, Rosen AE, Hainfeld JF, Seeman NC, Musier-Forsyth K, Kiehl RA. Selfassembly of Metallic Nanoparticle Arrays by DNA Scaffolding. J Nanoparticle Res. Aug. 2002;4(4):313-7.

Xu YY, Bian C, Chen S, Xia S. A microelectronic technology based amperometric immunosensor for $\alpha$-fetoprotein using mixed self-assembled monolayers and gold nanoparticles. Anal Chim Acta. Mar. 2006;561(1-2):48-54.

Xu W, Xu S, Ji X, Song B, Yuan H, Ma L, Bai Y. Preparation of gold colloid monolayer by immunological identification. Colloids Surf B: Biointerfaces. Feb. 2005;40(3-4):169-72.

Yang M, Qu F, Lu Y, He Y, Shen G, Yu R. Platinum nanowire nanoelectrode array for the fabrication of biosensors. Biomaterials. Dec. 2006;27(35):5944-50. Epub Sep. 1, 2006.

Yang Y, Wang Z, Yang M, Li J, Zheng F, Shen G, Yu R. Electrical detection of deoxyribonucleic acid hybridization based on carbon-nanotubes/nano zirconium dioxide/chitosan-modified electrodes. Anal Chim Acta. Feb. 19, 2007;584(2):268-74. Epub Nov. 28, 2006.

Yao H, Yi C, Tzang CH, Zhu J, Yang M. DNA-directed self-assembly of gold nanoparticles into binary and ternary nanostructures. Nanotechnology. Jan. 2007;18(1).

Yeh, et al. Nanowiring of a Redox Enzyme by Metallized Peptides, Biosensors and Bioelectronics (2005) 21:973-978.

Yeh JI, Claiborne A. Crystal structures of oxidized and reduced forms of NADH peroxidase. Methods Enzymol. 2002;353:44-54.

Yu S, Li N, Wharton J, Martin CR. Nano Wheat Fields Prepared by Plasma-Etching Gold Nanowire-Containing Membranes. Nano Lett. 2003;3(6):815-8.

Yu X, Munge B, Patel V, Jensen G, Bhirde A, Gong JD, Kim SN, Gillespie J, Gutkind JS, Papadimitrakopoulos F, Rusling JF. Carbon nanotube amplification strategies for highly sensitive immunodetection of cancer biomarkers. J Am Chem Soc. Aug. 30, 2006;128(34):11199-205.

Claiborne A, Mallett TC, Yeh JI, Luba J, Parsonage D. Structural, redox, and mechanistic parameters for cysteine-sulfenic acid function in catalysis and regulation. Adv Protein Chem. 2001;58:215-76.

Dai, H., Nanotube Growth and Characterization, Dresselhaus, M., Dresselhaus, G.; Avouris, P. (Eds.), 2001. Carbon Nanotubes: Synthesis, Structure, Properties, and Applications. Springer-Verlag, Berlin, pp. 29-53.

Franzini R.; Watson, R. M.; Patra, G.K.; Popescu, D. L.; Achim, C., Metal Incorporation in Modified Peptide Nucleic Acids, Polymer Preprints, 2004, 45, 337-338.

Niemeyer, C.M. (Ed.), 2004. Bioconjugation Protocols: Strategies and Methods. Humana Press, Totowa, NJ, pp. 295-304.

Saito, R., Dresselhaus, G., Dresselhaus, M. (Eds.), 1998. Physical Properties of Carbon Nanotubes. Imperial College Press, London, UK, Table of Contents, pp. 220-225.

Zheng G, Patolsky F, Cui Y, Wang WU, Lieber CM. Multiplexed electrical detection of cancer markers with nanowire sensor arrays. Nature Biotechnology, Oct. 2005;23(10):1294-301.

International Preliminary Report on Patentability, Patent Cooperation Treaty Application No. PCT/US2008/075217, University of Pittsburgh, et al., Mailed Mar. 18, 2010 (related application).

Alivisatos AP, Johnsson KP, Peng X, Wilson TE, Loweth CJ, Bruchez MP Jr, Schultz PG. Organization of 'nanocrystal molecules' using DNA. Nature. Aug. 15, 1996;382(6592):609-11.

Che G, Cabrera CR. Molecular recognition based on (3-mercaptopropyl) trimethoxysilane modified gold electrodes. J Electroanal Chem. Nov. 1996;417(1-2):155-61.

Claiborne A, Yeh JI, Mallett TC, Luba J, Crane EJ 3rd, Charrier V, Parsonage D. Protein-sulfenic acids: diverse roles for an unlikely player in enzyme catalysis and redox regulation. Biochemistry. Nov. 23, 1999;38(47):15407-16.

Csáki A, Garwe F, Steinbrück A, Maubach G, Festag G, Weise A, Riemann I, König K, Fritzsche W. A parallel approach for subwavelength molecular surgery using gene-specific positioned metal nanoparticles as laser light antennas. Nano Lett. Feb. 2007;7(2):247-53. Epub Jan. 24, 2007.

Csáki A, Möller R, Straube W, Köhler JM, Fritzsche W. DNA monolayer on gold substrates characterized by nanoparticle labeling and scanning force microscopy. Nucleic Acids Res. Aug. 15, 2001;29(16):E81.

F. Faßbender, G. Schmitt, M. J. Schöning, H. Lüth, G. Buß, J. -W. Schultze. Optimization of passivation layers for corrosion protection of silicon-based microelectrode arrays. Sensors Actuators B. Aug. 2000;68(1-3):128-33.

Franzini RM, Watson RM, Patra GK, Breece RM, Tierney DL, Hendrich MP, Achim C.Metal binding to bipyridine-modified PNA. Inorg Chem. Nov. 27, 2006;45(24):9798-811.

Gasparac R, Taft BJ, Lapierre-Devlin MA, Lazareck AD, Xu JM, Kelley SO. Ultrasensitive electrocatalytic DNA detection at two- and three-dimensional nanoelectrodes. J Am Chem Soc. Oct. 6, 2004;126(39):12270-1.

Georgiadis R, Peterlinz K, Peterson A, Quantitative Measurements and Modeling of Kinetics in Nucleic Acid Monolayer Films Using SPR Spectroscopy. J Am Chem Soc. Mar. 2000;122(13):3166-73.

Hazarika P, Irrgang J, Spengler M, Niemeyer CM. Biochemical Synthesis and Manipulation of a 70nm DNA Linker for the Assembly of DNA-Functionalized Gold Nanoparticles. Adv Functional Mat. Feb. 2007;17(3):437-42.

Helfrich MR, El-Kouedi M, Etherton MR, Keating CD. Partitioning and assembly of metal particles and their bioconjugates in aqueous two-phase systems. Langmuir. Aug. 30, 2005;21(18):8478-86.

Hirsch R, Katz E, Willner I. Magneto-Switchable Bioelectrocatalysis. J Am Chem Soc. Nov. 2000;122(48):12053-4.

Itaya K, Ataka T, Toshima S. Spectroelectrochemistry and electrochemical preparation method of Prussian blue modified electrodes. J Am Chem Soc. Sep. 1082;104(18):4767-72.

Karpovich DS, Blanchard GJ. Direct Measurement of the Adsorption Kinetics of Alkanethiolate Self-Assembled Monolayers on a Microcrystalline Gold Surface. Langmuir. 1994;10(9):3315-22.

Koehne J, Chen H, Li J, Cassell AM, Ye Q, Ng HT, Han J, Meyyappan M. Ultrasensitive label-free DNA analysis using an electronic chip based on carbon nanotube nanoelectrode arrays. Nanotechnology. Oct. 2003;14(12):1239-45.

Koehne J, Li J, Cassell AM, Chen H, Ye Q, Ng HT, Pan J, Meyyappan M. The fabrication and electrochemical characterization of carbon nanotube nanoelectrode arrays. J Mater Chem. 2004;14(4):676-84.

Koehne JE, Li J, Cassell AM, Chen H, Ye Q, Han J, Meyyappan M. System Optimization for the Development of Ultrasensitive Electronic Biosensors Using Carbon Nanotube Nanoelectrode Arrays. Mech Chem Biosyst. 2004;1(1):69-80.

Krantz BA, Sosnick TR. Engineered metal binding sites map the heterogeneous folding landscape of a coiled coil. Nat Struct Biol. Dec. 2001;8(12):1042-7.

Krishnamoorthy K, Zoski CG. Fabrication of 3D gold nanoelectrode ensembles by chemical etching. Anal Chem. Aug. 1, 2005;77(15):5068-71.

Lapierre-Devlin MA, Asher CL, Taft BJ, Gasparac R, Roberts MA, Kelley SO. Amplified electrocatalysis at DNA-modified nanowires. Nano Lett. Jun. 2005;5(6):1051-5.

Li J, Ng HT, Cassell A, Fan W, Chen H, Ye Q, Koehne J, Han J, Meyyappan M. Carbon Nanotube Nanoelectrode Array for Ultrasensitive DNA Detection. Nano Lett. 2003;3(5):597-602.

Li J, Papadopoulos C, Xu JM, Moskovits M. Highly-ordered carbon nanotube arrays for electronics applications. Appl Phys Lett. Jul. 1999;75:367-9.

Lin YY, Wang J, Liu G, Wu H, Wai CM, Lin Y. A nanoparticle label/immunochromatographic electrochemical biosensor for rapid and sensitive detection of prostate-specific antigen. Biosens Bioelectron. Jun. 2008;23(11):1659-65.

Liu J, Chou A, Rahmat W, Paddon-Row MN, Gooding JJ. Achieving Direct Electrical Connection to Glucose Oxidase Using Aligned Single Walled Carbon Nanotube Arrays. Electroanalysis. Jan. 2005;17(1):38-46.

Liu S, Zhang X, Wu Y, Tu Y, He L. Prostate-specific antigen detection by using a reusable amperometric immunosensor based on reversible binding and leasing of HRP-anti-PSA from phenylboronic acid modified electrode. Clin Chim Acta. Sep. 2008;395(1-2):51-6. Epub May 10, 2008.

Liu Y. Electrochemical detection of prostate-specific antigen based on gold colloids/alumina derived sol-gel film. Thin Solid Films. Feb. 2008;516(8):1803-8.

Luo L, Zhang Z, Hou L. Development of a gold nanoparticles based chemiluminescence imaging assay and its application. Anal Chim Acta. Feb. 12, 2007;584(1):106-11. Epub Nov. 7, 2006.

Menon VP, Martin CR. Fabrication and Evaluation of Nanoelectrode Ensembles. Anal Chem. Jul. 1996;67(13):1920-8.

Mirkin CA, Letsinger RL, Mucic RC, Storhoff JJ. A DNA-based method for rationally assembling nanoparticles into macroscopic materials. Nature. Aug. 15, 1996;382(6592):607-9.

Mo Z, Wang H, Liang Y, Liu F, Xue Y. Highly reproducible hybridization assay of zeptomole DNA based on adsorption of nanoparticle-bioconjugate. Analyst. Dec. 2005;130(12):1589-94. Epub Oct. 3, 2005.

Mu C, Yu Y, Liao W, Zhao X, Xu D, Chen X, Yu D. Controlling growth and field emission properties of silicon nanotube arrays by multistep template replication and chemical vapor deposition. Appl Phys Lett. Sep. 2005;87(11).

Mu C, Zhao Q, Xu D, Zhuang Q, Shao Y. Silicon Nanotube Array/Gold Electrode for Direct Electrochemistry of Cytochrome c. J Phys Chem B. Jan. 2007;111(6):1491-5.

O'Shea EK, Klemm JD, Kim PS, Alber T. X-ray structure of the GCN4 leucine zipper, a two-stranded, parallel coiled coil. Science. Oct. 25, 1991;254(5031):539-44.

Panini NV, Messina GA, Salinas E, Fernández H, Raba J. Integrated microfluidic systems with an immunosensor modified with carbon nanotubes for detection of prostate specific antigen (PSA) in human serum samples. Biosens Bioelectron. Feb. 28, 2008;23(7):1145-51. Epub Nov. 13, 2007.

Papadopoulos C, Chang B, Yin A, Xu J. Engineering Carbon Nanotubes via Template Growth. Int J Nanosci. Jun./Aug. 2002;1(3/4):205-12.

Parsonage D, Miller H, Ross RP, Claiborne A. Purification and analysis of streptococcal NADH peroxidase expressed in *Escherichia coli*. J Biol Chem. Feb. 15, 1993;268(5):3161-7.

Petrovykh DY, Kimura-Suda H, Whitman LJ, Tarlov MJ. Quantitative analysis and characterization of DNA immobilized on gold. J Am Chem Soc. Apr. 30, 2003;125(17):5219-26.

Poole LB, Claiborne A. Interactions of pyridine nucleotides with redox forms of the flavin-containing NADH peroxidase from *Streptococcus faecalis*. J Biol Chem. Nov. 5, 1986;261(31):14525-33.

Qu B, Chu X, Shen G, Yu R. A novel electrochemical immunosensor based on colabeled silica nanoparticles for determination of total prostate specific antigen in human serum. Talanta. Aug. 15, 2008;76(4):785-90. Epub Apr. 20, 2008.

Ribrioux S, Kleymann G, Haase W, Heitmann K, Ostermeier C, Michel H. Use of nanogold- and fluorescent-labeled antibody Fv fragments in immunocytochemistry. J Histochem Cytochem. Mar. 1996;44(3):207-13.

Ricci F, Palleschi G. Sensor and biosensor preparation, optimisation and applications of Prussian Blue modified electrodes. Biosens Bioelectron. Sep. 2005;21(3):389-407.

Roberts MA, Kelley SO. Ultrasensitive detection of enzymatic activity with nanowire electrodes. J Am Chem Soc. Sep. 19, 2007;129(37):11356-7. Epub Aug. 22, 2007.

Sabatani E, Rubinstein I. Organized self-assembling monolayers on electrodes. 2. Monolayer-based ultramicroelectrodes for the study of very rapid electrode kinetics. J Phys Chem. Dec. 1987;91(27):6663-9.

* cited by examiner

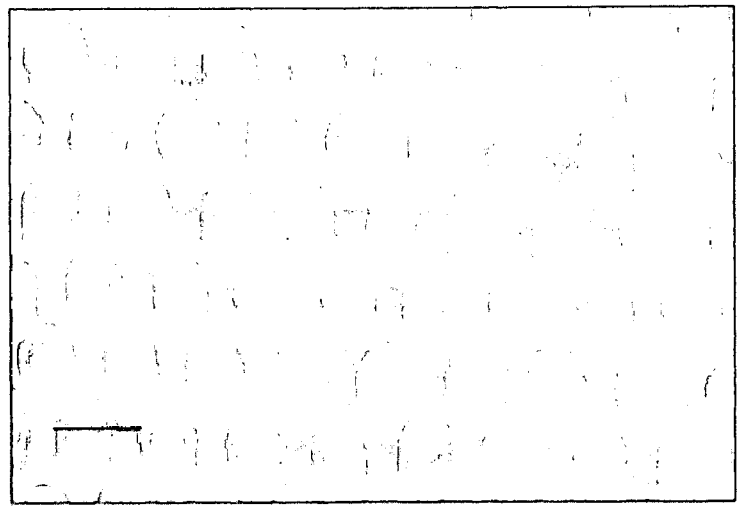
Fig. 6
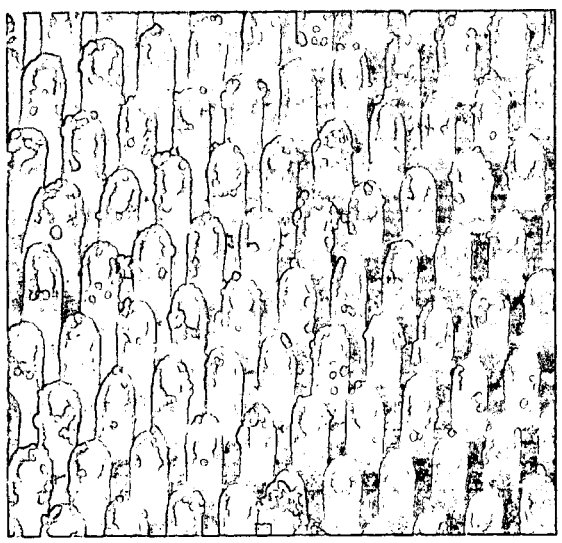
Fig. 7A Fig. 7B

BIOSENSORS AND RELATED METHODS

CROSS-REFERENCE TO RELATED APPLICATIONS

This application claims the benefit under 35 U.S.C. §119(e) to U.S. Provisional Patent Application No. 60/969,864 filed on Sep. 4, 2007, which is incorporated herein by reference in its entirety.

STATEMENT REGARDING FEDERAL FUNDING

The U.S. Government has a paid-up license in this invention and the right in limited circumstances to require the patent owner to license others on reasonable terms as provided for by the terms of Grant No. GM-66466 awarded by the National Institutes of Health and Grant No. F49620-03-1-0365 awarded by the Air Force Office of Scientific Research.

Provided herein are biosensors and methods of detecting analytes in a solution. In one non-limiting embodiment, the analyte is Prostate Specific Antigen (PSA).

Biosensors are a type of analytical device that use biological molecules to monitor biorecognition events and interactions. Coupled to the progress in nanotechnologies over recent years, the development of a nanobiosensor based on individual nanoelectrodes and nanoelectrode arrays or nanoelectrode ensembles offers unprecedented avenues for screening and detection at ultrahigh sensitivities. These capabilities provide the basis for a paradigmatic change in biomedical diagnostics and treatment.

The ability to monitor biorecognition events and interactions on platforms offers pathways to the application of biological macromolecules as detectors. Coupled with the ability to produce conductive elements precisely on the nanoscale, biosensing offers unprecedented opportunities for screening and detection at increasing sensitivities. Recent progress in nanotechnology has enabled the development of highly sensitive nanobiosensors. Generally, a nanobiosensor comprises a biological component, a linker or mediator alongside nanoelectrodes; the various components can be equated with the electronic elements of a sensor because the components transduce the signal generated at the source (bioelement) to the detector (electrode).

The biological component can be a protein (e.g., enzymes or antibodies), nucleic acid (DNA or RNA) or even entire cells. The bioelement is responsible for the binding and recognition of the special target analyte, whether a small molecule or a large protein partner. The binding event is the basis for signal generation and a physical element, such as an electrode, captures the signal as the output. As the electrode, this component translates information from the biological element into a chemical or physical output with a defined sensitivity. The information that is detected can be chemical, energetic, such as detection of light, or essentially any information that organisms innately process because all of these signals depend on biological molecules for their generation and/or signal detection and transduction.

As the detector, the electrode is the component that translates information from the biological element into a chemical or physical output signal with a defined sensitivity. Electrodes for fabrication of nanobiosensors can be divided into individual nanoelectrodes and nanoelectrode arrays (NEAs) or nanoelectrode ensembles (NEEs). Nanobiosensors can comprise individual nanoelectrodes, NEAs or NEEs. Nanoelectrodes have one or more critical dimensions in the nanometer range, typically ranging between one nanometer (nm) and less than one micron ($\mu$m), and more typically less than 500 nm. A critical dimension is a dimension that controls or otherwise impacts the electrochemical response of the electrode. Generally, in keeping with other aspects of nanoscience and nanotechnology in which the length scale of interest typically ranges from one to hundreds of nanometers, a critical dimension of a nanoelectrodes can also be taken as being in that range. NEAs and NEEs are usually based on the assembly of densely-packed or random collections of carbon nanotubes (CNTs) and other nanostructured materials (e.g., platinum and gold nanowires). Owing to the properties of these nanostructured materials, they constitute new platforms for biomolecular sensing that might provide increased sensitivity and amenability to miniaturization.

Prostate cancer (PCa) is one example of a condition associated with a marker amenable to detection by nanobiosensors. PCa is a deadly malignancy and major cause of death in men population aged between 55 and 80 years and accounts for ~10% of all deaths from cancer. At present, there is no available curative therapy once the disease spreads the beyond limits of the organ. The best way to control and decrease mortality rate from PCa is to detect the disease at early stage, while it is localized and organ-confined. Experimental studies investigated that serum prostate specific antigen (PSA) is a mostly used as the biomarker for PCa and established as the most reliable clinical tool for diagnosing and monitoring the disease. PSA is a serine protease that is produced by the prostate epithelium to maintain liquefaction of seminal fluid. The PSA is found in the serum, either free or in complex with various proteinase inhibitors, among which the complex with alpha-1-antichymotrypsin (ACT) is predominant. Trace levels of PSA (i.e. free PSA plus ACT-bound PSA) are naturally found in the serum; however, PCa tumor growth usually leads to the release of high concentrations of PSA into the circulatory system. A PSA measurement above a cut-off value of 4.0 ng/ml (and more recently 2.5 ng/ml) is generally regarded as positive and might indicate the need for a biopsy.

Currently, most PSA testing takes place at dedicated, centralized laboratories on large, automated high-throughput systems, and numerous analyzer-run PSA assays are currently available in the marketplace. The advantages of such systems include low detection limits (in the region of 0.05-0.005 ng/ml), proven reliability and high-throughput of samples. However, an important disadvantage is that these large systems are only found in dedicated laboratories and this requires sample transportation to the testing site, which increases waiting times (often several weeks), administration and medical costs. Moreover, the cost of analyzer and associated instrumentation, sample transportation and storage, required sets of reagents, highly trained technical personnel and administration is rather high. Thus, near-patient or point-of-care testing (POCT) portable devices have been in development, which can obtain the results within several minutes. This can help to reduce the number of clinic visits, decrease costs to the patient and the healthcare system, increase patient satisfaction and improve clinical outcome. Some immunostrip tests (also named immunochromatographic membrane test) have been developed. The major advantage of immunostrip devices is their low cost, robust nature and ease of use. However, the immunostrip devices have not proved to be a real alternative to centralized laboratory testing for clinical PSA samples because of their general lack of sensitivity and, at best, semi-quantitative nature.

Recently, the development of biosensors, especially coordinated biosensors and nanobiosensors, has brought POCT for PSA closer to reality because they provide rapid and reliable quantitative results "at anytime and anywhere". Compared to traditional measurement techniques, the biosensors have obvious advantages, which include the reduced to the size of devices, the requirement of only small amounts of sample and reagents, high specificity and high sensitivity. Electrochemical biosensors have received much attention in the field of PSA biosensing because they provide a simple, inexpensive and accurate platform for the measurement of the target analyte. Electrochemical biosensors determine the analyte level by detecting the changes in either potential, current, capacitance, conductance or impedance caused by a specific biorecognition reaction.

SUMMARY

Provided herein are biosensors that comprise a biological signal source linked to a substrate that is conductive to the biological signal (which can also be referred to as a "conductor"), by a peptide nucleic acid spacer ("PNA") and methods of use of the biosensor. In one non-limiting embodiment, the biological signal source is a redox enzyme linked to the PNA and the conductive substrate is one of an electrode, a nanoelectrode and a nanoelectrode needle. In another, the biological signal source is a binding reagent linked to a nanoelectrode by a conductive peptide nucleic acid spacer.

The binding reagent may be an antibody, such as an anti-PSA antibody. In use, binding reagent may be attached to a redox tag comprising an antigen for binding the reagent attached to a redox enzyme or a portion thereof, capable of catalyzing an electrochemical reaction (redox) in the presence of a substrate of the redox enzyme. In use, the redox tag is displaced by an analyte comprising the specific binding partner of the binding reagent, changing electron flow through the biosensor. In one non-limiting embodiment, the binding reagent is linked to the nanoelectrode by a protein spacer comprising one or more metal binding sites and is metalized with one or more metal atoms.

In another embodiment, the biosensor comprises a redox enzyme (or a functional portion thereof) that catalyzes redox event in the presence of an analyte, which is a substrate of the redox enzyme. In such a case, the redox enzyme, such as, without limitation, one of NADH peroxidase, glucose oxidase, alkaline phosphatase and horseradish peroxidase, is linked (attached) to the PNA, which, in-turn is linked to an electrode, nano-electrode or nanobioneedle, which all act as conductors of electrons to permit detection of any signal changes in the biosensor. Nanoelectrodes may be fabricated from one or more of a gold nanowire, a carbon nanotube, a platinum nanowire and a silicon nanotube. Nanobioneedles (also nano-electrodes) can be fabricated from carbon nanotubes, such as multi-walled carbon nanotubes.

In yet another embodiment the biological signal source generates a signal detectable by optical methods, such as, without limitation, surface plasmon resonance, or piezoelectric methods.

The conductivity of the PNA may be enhanced by any useful method, such as, without limitation, by coordinating a metal into the PNA in a metal-binding group that is incorporated into the PNA. Non-limiting examples of metal-binding groups include: pyridine, bipyridine, porphyrin, and hydroxyquinoline groups.

Also provided are methods of detecting or quantifying an analyte in a sample comprising contacting the sample with a biosensor comprising a biological signal source connected to a conductive substrate by a peptide nucleic acid spacer and determining if, or the extent of which, a signal from the biological signal source is changed in the presence of the sample as indicative of the presence or the analyte in the sample. In certain non-limiting embodiments, the biological signal source is one of a binding reagent specific to the analyte bound to a redox tag; and a redox enzyme specific to the analyte, in which case, the method comprises determining if, or to what extent, electron transfer through the peptide nucleic acid spacer is altered in the presence of the sample, as being indicative of presence of the analyte in the sample. For example and without limitation, the biosensor may comprise a binding reagent specific to the analyte linked to the spacer and bound to a redox tag, and a redox substrate is added to the sample, wherein displacement of the redox tag by the analyte alters electron transfer rates through the spacer. In another non-limiting example, the biosensor may comprise a redox enzyme linked to the spacer and the analyte is a substrate of the redox enzyme.

In another embodiment, a method is provided for detecting or quantifying PSA in a sample. The method comprising contacting the sample with a biosensor comprising a first anti-PSA binding reagent linked to a metalized polypeptide spacer which is linked to a nanoelectrode, and in which (a) the binding reagent is bound to a redox tag comprising a PSA antigen linked to a redox enzyme, and a redox substrate specific to the redox enzyme is added to the sample and further comprising determining if, or the extent of which, a signal from the redox tab is changed in the presence of the sample as indicative of the presence of PSA in the sample, wherein displacement of the redox tag by PSA in the sample alters electron transfer rates through the spacer; or (b) determining, in a solution comprising a redox tag comprising a redox enzyme linked to a second anti-PSA binding reagent and a substrate for the redox enzyme, wherein the redox tag binds PSA when the first anti-PSA binding reagent binds PSA, the extent of binding of the redox tag to PSA and to the first anti-PSA binding reagent as indicated by increased electron flow through the nanoelectrode.

BRIEF DESCRIPTION OF THE DRAWINGS

FIG. 3A is a schematic structure of a PSA biosensor comprising PNA, where FIG. 3B is a schematic structure of another PSA biosensor comprising PNA and AuNP (gold nanoparticle).

FIG. 4A shows CV curves of PNA/PSA-antibody assembled electrode before (curve a) and after (curve b) binding PSA-GOx complex. FIG. 4B is a graph showing the relationship between current and PSA concentration.

FIG. 6 is a SEM image taken at a 30 degree tilt angle; scale bar represents 100 nm, of the bare CNT electrode array.

FIGS. 7A and 7B are SEMs of CNT Electrode Arrays. FIG. 7A shows immobilized bioassembly, localized to CNT tips. FIG. 7B shows that controlled deposition of bioassembly can be achieved to attenuate or amplify output.

DETAILED DESCRIPTION

Figure 1A:
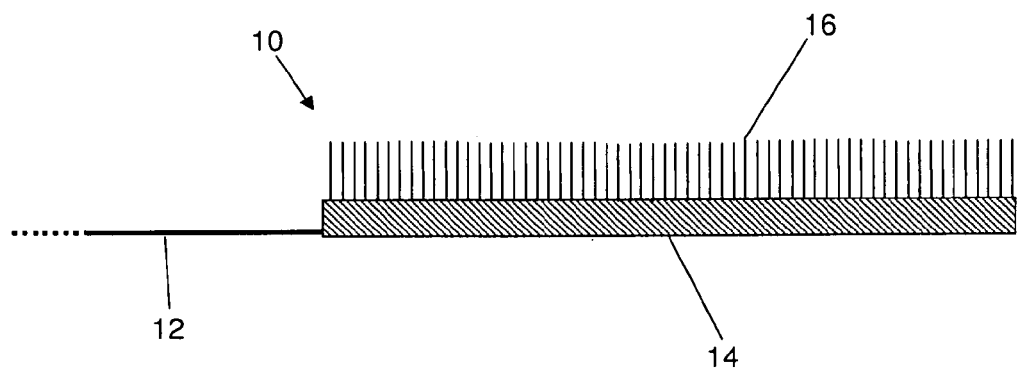
FIGS. 1A-1C show schematic cross-sections of non-limiting examples of useful electrode structures.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the term "analyte" refers to a substance which, when measured, may be used to assess a change or effect in a system, such as a biological system. A "biological marker" or "biomarker" is an analyte in a biological system and may be used as an indicator of the risk or progression of disease. A "redox" or "oxidation-reduction" reaction describes any reaction in which electrons are transferred from one molecule, compound, molecular group, etc. to another. The process of oxidation occurs in conjunction with (is coupled with) a reduction reaction, thus resulting in the transfer of electrons. A redox enzyme is an enzyme that catalyzes a reaction with one or more enzyme substrate(s), resulting in generation or utilization of electrons. In some instances, redox enzymes employ no prosthetic group, such as those that use reversible formation of a disulfide bond between two cysteine residues, as in the case of thioredoxin. Other redox enzymes use prosthetic groups, such as flavins, NAD, transition metal ions or clusters of such metal ions, etc. The use of the transition metal ions in these enzymes is due to their ability to attain multiple oxidation and spin states.

The application of biological macromolecules as detectors provides a means of monitoring biorecognition events and interactions on nanoplatforms. Coupled to the ability to precisely produce conductive elements on the nanoscale, biosensing offers unprecedented avenues for screening and detection at increasing sensitivities. Therefore provided herein are biosensor devices comprising a biological signal source attached to a conductive substrate (conductor, such as an electrode). In one non-limiting example, the biological signal source is an electrochemical signal source, such as a redox enzyme attached either directly, or through a binding partner intermediary, to a peptide nucleic acid (PNA) that optionally is modified to incorporate transition metal ions or otherwise treated to rationally change its electron transfer properties (an "enhanced-conductivity PNA"). Native PNA typically is sufficiently conductive to transfer electrons in the electrode systems described herein, but enhanced-conductivity PNA may be preferable in many instances. "Conductive peptide nucleic acids" refer both to PNAs and enhanced-conductivity PNAs having the ability to transfer electrons in a nanoelectrode. The PNA is then attached to an electrode or other conductor to facilitate the transfer of electrons to an output or analytical device, such as a meter and/or computer processor, optionally provided with software and/or hardware processes for outputting and/or analyzing a signal from the biosensor. The various components, whether biologic or synthetic in nature, can be equated with the electronic elements of a physical sensor as each of these components transduces the signal generated at the source (biomolecule) to the detector (electrode). A metalized protein linker, prepared, for example and without limitation, as described in Yeh et al. ((2005) *Biosensors and Bioelectronics*, 21:973-978) is useful in producing a biosensor specific to PSA.

In another non-limiting example, the biological signal source is not electrochemical, but the PNA structure offers may structural, functional, and conformational benefits over (e.g.) peptides and DNA. Detection of non-electrochemical changes in the biological signal source may be detected by any useful method, such as, without limitation, optically, for example and without limitation by fluorescence or surface plasmon resonance (SPR) or piezoelectrically. Tables 1-3 provide lists of analyte, biological signal sources and detection methods useful for electrochemical or other forms of detection of analytes in a sample, cell or organism.

Table 1—PNA can be used as a linker between the electrode surface and enzymes to fabricated enzyme biosensors. These biosensors are usually used to detect the analytes by electrochemical methods such as amperometry and voltammetry. The following is a non-limiting list of enzyme biosensors that can be used for detection of different analytes.

nosensors. These immunosensors usually use many different detection methods to detect analytes, including electrochemical methods (e.g., amperometry and voltammetry), optical methods (e.g., SPR, fluorescence) and piezoelectric methods (e.g., microcantilever). Table 2 shows some potential immunosensors for detection of different biomarkers of cancer. PNA can be used as the linker to connect most antibodies to detect specific antigens. An antigen-modified electrode or BIAcore chip can be used to detect antibodies. Table 3 shows some examples of antibody-antigen combinations for detection of specific analytes/biomarkers.

TABLE 1

Enzyme biosensors for different targets

| Enzyme | Analyte | Application | Detection method |
| --- | --- | --- | --- |
| Glucose oxidase | Glucose | Clinical diagnosis, food industry | Electrochemical detection (e.g., amperometry, voltammetry, etc.) |
| Alcohol oxidase or alcohol dehydrogenase | Ethanol | Forensic laboratories, clinical diagnosis, food industry | Electrochemical detection (e.g., amperometry, voltammetry, etc.) |
| Cholesterol oxidase and Cholesterol esterase | Total cholesterol | Clinical diagnosis | Electrochemical detection (e.g., amperometry, voltammetry, etc.) |
| Choline oxidase and acetylcholinesterase | Choline; acetylcholine; pesticide detection | Clinical diagnosis, organophosphorous- and carbamate-based pesticides analysis in agriculture | Electrochemical detection (e.g., amperometry, voltammetry, etc.); Optical detection (e.g., optical fiber biosensor, fluorescence, surface plasmon resonance (SPR));[a] Piezoelectric (e.g., quartz crystal microbalance)[a] |
| Galactose oxidase | Galactose | Clinical diagnosis | Electrochemical detection (e.g., amperometry, voltammetry, etc.) |
| Glutamate oxidase or glutamate dehydrogenase | Glutamate | Clinical diagnosis | Electrochemical detection (e.g., amperometry, voltammetry, etc.) |
| Lactate oxidase | Lactic acid | Clinical diagnosis | Electrochemical detection (e.g., amperometry, voltammetry, etc.) |
| Lysine oxidase | Lysine | Foods and drugs evaluation | Electrochemical detection (e.g., amperometry, voltammetry, etc.) |
| Oxalate oxidase | Oxalate | Clinical diagnosis | Electrochemical detection (e.g., amperometry, voltammetry, etc.) |
| Xanthine oxidase | Xanthine | Food evaluation | Electrochemical detection (e.g., amperometry, voltammetry, etc.) |
| Hemoglobin | Nitric oxide | Clinical diagnosis, environmental analysis | Electrochemical detection (e.g., amperometry, voltammetry, etc.) |
| NADH peroxidase or horseradish peroxidase | hydrogen peroxide | Pharmaceutical analysis, environmental analysis | Electrochemical detection (e.g., amperometry, voltammetry, etc.) |
| Glycerol-3-phosphate dehydrogenase or glycerol-3-phosphate oxidase and glycerol kinase | Glycerol-3-phosphate; Glycerol; ATP | Clinical diagnosis | Electrochemical detection (e.g., amperometry, voltammetry, etc.); Optical detection (e.g., SPR) |
| tyrosinase, horseradish peroxidase, acetyl cholinesterase and butyryl cholinesterase et al. | chemical oxygen demand (COD), biological oxygen demand (BOD), total organic carbon (TOC), inhibition of nitrification, inhibition of respiration and toxicity | Environmental analysis | Electrochemical detection (e.g., amperometry, voltammetry, etc.) |

[a] Optical detection (optical fiber biosensor, fluorescence, SPR) and piezoelectric (quartz crystal microbalance) are used for detection of organophosphorous and carbamate-based pesticides.

Table 2—PNA can be also used as the linker between the electrode surface and the antigen/antibody to fabricate immu-

TABLE 2

Immunosensors for detection of different biomarkers of cancer

| Biomarker | Cancer | Detection method |
| --- | --- | --- |
| Prostate specific antigen | Prostate cancer | Electrochemical detection (amperometry, voltammetry, impedance, etc.); Optical detection (e.g., fluorescence, SPR); Piezoelectric (e.g., microcantilever) |
| Alpha-fetoprotein, carcinoembryonic antigen | Liver cancer | Electrochemical detection (e.g., amperometry, capacitance, etc.); Optical detection (e.g., optical fiber, SPR); Piezoelectric (e.g., Quartz crystal microbalance) |
| Carcinoembryonic antigen, CA19-9, CA24-2 | Colorectal and pancreatic cancer | Optical detection (e.g., optical fiber, SPR) |

TABLE 2-continued

Immunosensors for detection of different biomarkers of cancer

| Biomarker | Cancer | Detection method |
| --- | --- | --- |
| Carcinoembryonic antigen; CA72-4, CA19-9 squamous cell carcinoma antigen | Gastric carcinoma Esophagus carcinoma | Optical detection (e.g., optical fiber, SPR) microcantilever, SPR |
| Carcinoembryonic antigen, CA19-9, squamous cell carcinoma antigen, CYFRA21-1, Neuron specific enolase | Lung cancer | Optical detection (e.g., optical fiber, SPR) microcantilever |
| Carcinoembryonic antigen, CA15-3, CA125 | Breast cancer | Optical detection (e.g., optical fiber, SPR), microcantilever |
| Alpha-fetoprotein, carcinoembryonic antigen, human chorionic gonadotropin, CA125 | Epithelial ovarian tumors | SPR microcantilever |
| human chorionic gonadotropin, squamous cell carcinoma antigen | Trophoblastic cancer | SPR microcantilever |

TABLE 3

Immunosensors for detection of some risk biomarkers.

| Immunosensor | Analyte | Detection method |
| --- | --- | --- |
| Antibody | C-reactive protein, myoglobin, serum amyloid A, TNF-α, fatty acid binding protein | Optical detection (fluorescence, SPR); Piezoelectric (microcantilever) |
| 2,4-dichlorphenoxyacetic acid or other antigen | monoclonal antibody polyclonal antibody | Piezoelectric (microcantilever) |

As biomolecules are integral sensing units, the kinetics of the interactions between individual molecules and between the molecules and their surroundings dictate the rates of signal transduction, as is the case in native biological systems. Consequently, as in enzymes, rate improvements can occur from proximity and geometric effects, with potential enhancements of $10^2$ to $10^3$ at each junction. Signal-to-noise improvements have been shown to be achieved in carbon nanotubes, as well as other nanotube or nanofiber structures, through changing their dimensions. This advantage can be exploited if individual nanotubes are accessed physically and electrically, as described herein. This benefit is multiplied when precise, atomically-resolved coordinates of biological structures are known and rationally used in the design of the nanoelectrode platform to further align the signal transducing units.

Therefore, described herein is the application of highly stable PNA linkers that, optionally, are modified to enhance their electron conduction properties. For example and without limitation, the PNA linkers comprise PNA modified to bind metals or other compounds to enhance their electron transfer capability. These PNAs are functionalized at one end with a biomolecular source (for example and without limitation, a redox enzyme-conjugated tag or redox tag). They are attached at the other end to an electrode surface or other conductor for detecting current produced by electrochemical events at the biomolecular source(s) to an output/analytical device such as an electrochemical workstation. The PNA linker acts as a bridge that transfers electrons between the biomolecular source and the electrode. This allows for the modular production of biosensors in which the protein and electrode components can be readily swapped and replaced, as would be in the non-limiting embodiment where a biomolecular source is attached to a first strand of a PNA and a second PNA strand, complementary, and therefore capable of hybridizing to the first strand; is attached to an electrode. Modularity in design allows facile production of biosensors to detect a large array of ligands.

The PNA linker serves multiple purposes. Its well-defined stable structure serves as a spacer between the binding reagent or enzyme and the electrode surface, helping to prevent surface denaturation. Functionalization of the PNA allows for specific linkage to the binding reagent or enzyme and electrode, facilitating a homogenous distribution of the assembly on an electrode surface. The PNA's structural integrity and elongated conformation permits attachment to the binding reagent or enzyme with little perturbation to the binding reagent's or enzyme's structure, and, where relevant, provides a means of directing the electrons generated at the enzyme center to the electrode.

In one non-limiting embodiment, the biomolecular complex is attached specifically to the tips of nanoelectrodes, such as, without limitation, carbon nanotube electrodes. The biomolecular complexes are attached to the electrodes using a stoichiometric labeling approach. In a biocomplex comprising a binding reagent, such as an antibody, attached to a PNA linker, the PNA may be first linked to the binding reagent. The biocomplex is then metallized, for example with copper and/or cobalt. Optionally, a gold nanoparticle can be attached to the PNA prior to metalizing (see, e.g., Yeh, et al. Nanowiring of a Redox Enzyme by Metallized Peptides, *Biosensors and Bioelectronics* (2005) 21:973-978). An electrode-less deposition approach to enhance the gold nanoparticle's size to aid in visualization via scanning electron microscopy (SEM) can then be done. This would permit controlled growth of the nanoparticle size as a phasing reagent while allowing for stoichiometric linkage of nanoparticles to the assembly. Once the peptide-protein reaction is completed, the whole assembly can be purified from non-reacted material by chromatography.

According to one embodiment of the present disclosure, a biosensor is provided comprising a binding reagent, such as an antibody or a receptor, linked to an electrode via a PNA linker. The PNA linker is typically treated with a metal ion in order to augment the electron transfer capacity of the PNA and to produce a PNA "wire". Functionality of the biosensor depends on the binding association of the biosensor with a reagent or analyte that has the capacity to create electron flow (current) within the biosensor when bound to the biosensor. The term "binding reagent" and like terms, refers to any molecule or ion capable of specifically or substantially specifically (that is with limited cross-reactivity) bind another chemical entity, which, in the case of immune-recognition, contains an epitope. In many instances, the binding reagents are antibodies, such as polyclonal or monoclonal antibodies. "Binding reagents" also include derivatives or analogs of antibodies, including without limitation: Fv fragments; single chain Fv (scFv) fragments; Fab' fragments; F(ab')2 fragments; humanized antibodies and antibody fragments; camelized antibodies and antibody fragments; and multivalent versions of the foregoing. Multivalent binding reagents also may be used, as appropriate, including without limitation: monospecific or bispecific antibodies, such as disulfide stabilized Fv fragments, scFv tandems ((scFv) fragments), diabodies, tribodies or tetrabodies, which typically are covalently linked or otherwise stabilized (e.g., leucine zipper or helix stabilized) scFv fragments. "Binding reagents" also include aptamers (oligonucleic acid or peptide molecules that bind a specific target molecule), as described in the art. Binding partners, such as, without limitation, biotin/avidin and receptor/substrate combinations also are considered to be within the class of "binding reagents," though antibodies and their respective antigens also are considered to be binding partners. Further, two or more binding partners may be included in a single composition (e.g., a polypeptide chain). In one embodiment, this is a string of epitopes. In such a configuration, the epitopes contained in one compound (e.g., a polypeptide chain) do not have to be identical.

Methods of making antigen-specific or non-specific binding reagent compositions, including antibodies and their derivatives and analogs, are well-known in the art. Directed polyclonal antibodies can be generated by immunization of an animal and recovery of plasma. Pooled polyclonal antibodies are obtained from multiple subjects, including humans, which may be directed (each subject is vaccinated with a specific antigen, as in the common case of production of polyclonal antibodies in animal subjects, such as rabbits or horses). Monoclonal antibodies can be prepared according to standard (hybridoma) methodology. Antibody derivatives and analogs, including humanized antibodies can be prepared recombinantly by isolating a DNA fragment from DNA encoding a monoclonal antibody and subcloning the appropriate V regions into an appropriate expression vector according to standard methods. Phage display and aptamer technology is described in the literature and permit in vitro clonal amplification of antigen-specific binding reagents with good affinity and low cross-reactivity. Phage display reagents and systems are available commercially, and include the Recombinant Phage Antibody System (RPAS), commercially available from GE Healthcare Bio-Sciences Corp. of Piscataway, N.J. and the pSKAN Phagemid Display System, commercially available from MoBiTec GmbH, of Goettingen Germany. Aptamer technology is described for example and without limitation in U.S. Pat. Nos. 5,270,163; 5,475,096; 5,840,867 and 6,544,776.

Peptide nucleic acid (PNA) is a DNA analogue with a pseudopeptide backbone. For example and without limitation, the PNA backbone typically is 2-aminoethyl glycine to which, one of the four bases (adenine, guanine, thymine, or cytosine) found in DNA is linked through a methylenecarbonyl linkage. Other non-standard bases, such as inosine and uridine may be also linked to the backbone, as well as other functional groups, such as metal chelating groups as described herein. Any group(s), other than standard or non-standard bases capable of base pairing, that are incorporated linked to the PNA backbone must still allow the molecule to serve as a linker for purposes described herein. Like amino acids, PNA monomers have amino and carboxyl termini. Unlike DNA nucleotides, PNAs lack pentose sugar phosphate groups. PNA is an excellent structural mimic of DNA (or RNA), and PNA oligomers are able to form very stable duplex structures with Watson-Crick complementary DNA, RNA (or PNA) oligomers.

PNA oligomers, for example and without limitation, as long as 20 bases are easily synthesized using standard peptide synthesis protocols. Complementary strands of PNA will be synthesized to produce a double-stranded PNA and/or a single-stranded PNA may comprise palindromic or other internally-complementary sequences to impart conformational stability. The PNA may contain a metal-binding site, for example and without limitation, as in the Example below. The PNA strands typically will form a double-stranded structure with base-stacking interactions and with the metal-ligand moiety situated within or outside the duplex depending on the PNA sequence and length, and on the metal ion linked to the PNA. A number of commercial entities can produce PNA structures by various synthetic methods. Panagene (Dacjeon, Korea), is one commercial provider of PNA oligomers. U.S. Pat. Nos. 7,211,668, 7,179,896, 6,172,226, 6,133,444 and 6,063,569 describe PNA structures and methods of making PNA structures. Incorporation of one or more metal binding sites, such as, without limitation, pyridine, bipyridine, porphyrin, and hydroxyquinoline groups may be accomplished. For example, Achim et al. described PNA structures that incorporates metal binding groups (see, e.g., Franzini R. M.; Watson, R. M.; Patra, G. K.; Breece, R. M.; Tierney, D. L.; Hendrich, M. P.; Achim, C., Metal Binding to Bipyridine-Modified PNA Duplexes. *Inorg. Chem.* 2006, 45(18), 9798-9811; Watson, R. M.; Skorik, Y.; Patra, G. K.; Achim, C., Influence of Metal Coordination on the Mismatch Tolerance of Ligand-Modified PNA Duplexes, *J. Am. Chem. Soc.* 2005, 127(18), 14628-14639; Franzini R.; Watson, R. M.; Patra, G. K.; Popescu, D. L.; Achim, C., Metal Incorporation in Modified Peptide Nucleic Acids, *Polymer Preprints,* 2004, 45, 337-338 and Popescu, D.; Parolin, T.; Achim, C., Metal Ion Incorporation in PNA Duplexes, *J. Am. Chem. Soc.* 2003; 125 (21); 6354-6355).

In one non-limiting embodiment, a PNA with the sequence $NH_2$-LysCCGTQ$_1$ACGG-H, where A, C, G and T refer to adenine, cytosine, guanine and thymine bases, respectively, as with standard DNA, and $Q_1$ is a metal binding group, such as, without limitation a hydroxyquinoline or bipyridine group. Other metal binding groups or redox active groups may be attached to the PNA backbone, including, without limitation, a porphyrin or ferrocene group. As used in the examples below, $Q_1$ is hydroxyquinoline. The PNA may be of any suitable length, but is typically from 4 to 10 residues in length and either single stranded or double-stranded. The PNA may have various sequences, one example shown below, but not limiting to, palindromes and has distinct structural topology, according to X-ray crystallography analysis. Metal binding groups may be inserted into the helix at any place that does not functionally or structurally affect the PNA to render it useless for its intended purpose. Other secondary structures can be produced depending on the primary sequence of the PNA and the nature of the metal binding group and the metal ion. Multiple metal-binding sites can be incorporated into the PNA structure at any position. The length, secondary structure, number of metal-binding groups, etc., of the PNA may be varied in any manner, as long as the electron transfer ability of the PNA is not diminished below useful levels.

PNA oligomers may be synthesized to include standard amino acids, for instance at the N or C terminus, and to produce a PNA-peptide hybrid compound that contains the PNA structure combined with peptide functionality. In one non-limiting embodiment, a leucine zipper motif is attached to the PNA structure to connect the PNA linker to a redox enzyme, such as NADH peroxidase.

Metal ions bind to PNA oligomers containing one or more metal-binding groups by contacting the oligomer with stoichiometric or slightly excess quantities of a metal ion at a suitable pH, typically 7. Any metal ion useful in producing a fast electron transfer rate through the PNA structure will suffice. Non-limiting examples of suitable metals include Fe, Co, Ni, Cu, Pt, or Ru. The reduction potential and the degree of participation in the electron transfer through PNA are properties specific for each metal ion and can be modulated by the metal-binding groups and the position in the PNA structure where the metal ion is bound.

In embodiments described herein in which an antibody or other binding reagent is linked to an electrode by a metalized polypeptide, conductive metals, a such as those described herein can be introduced to polypeptides modified to contain metal-binding groups, as is known in the literature, for example and without limitation, in Yeh et al. ((2005) *Biosensors and Bioelectronics,* 21:973-978, by introducing histidine(s) along the polypeptide. One non-limiting example of this is in the examples, below, where anti-PSA antibody is linked to a nanoelectrode by a metalized polypeptide. Any polypeptide sequence may find use as a suitable linker when metalized, so long as it substantially retains the ability to permit transfer of electrons from the binding reagent or other source, to the nanoelectrode in useful, detectable amounts.

Figure 1B:
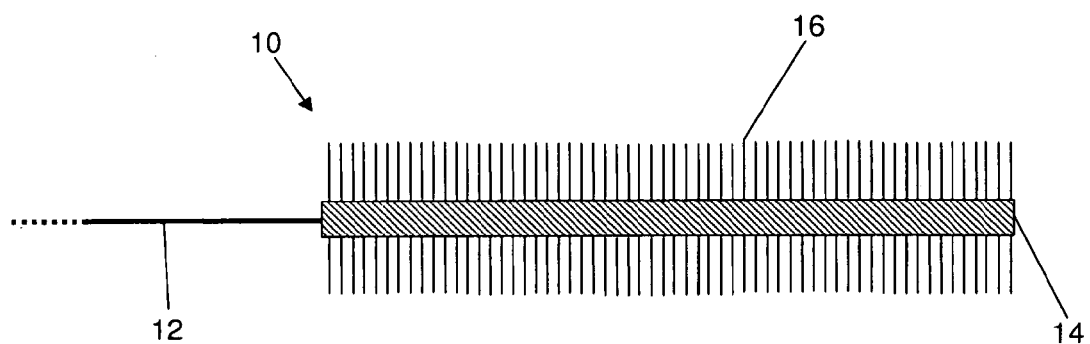
Figure 1C:
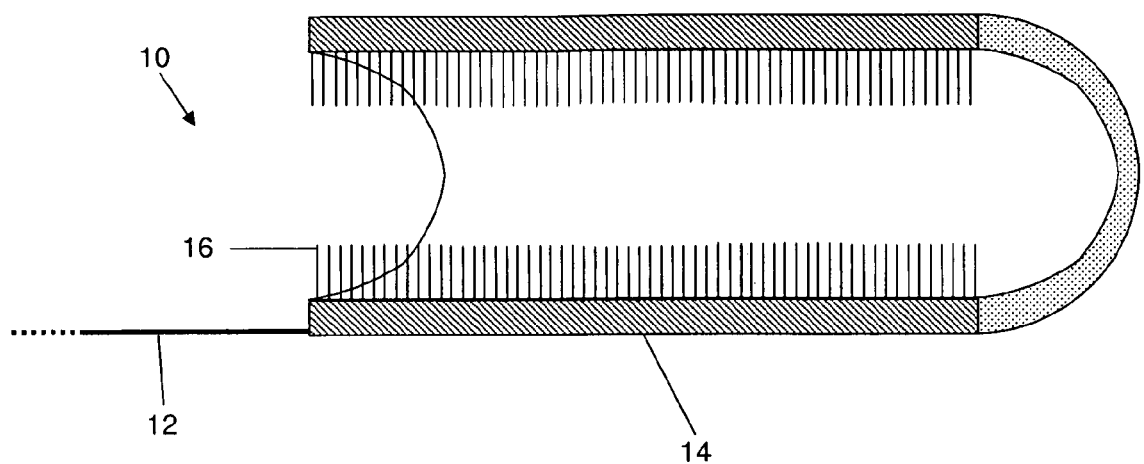

Electrode and nanoelectrode composition, structure and arrangement may vary considerably. FIGS. 1A-1C depict schematically a cross-section of a typical electrode 10 that includes a lead 12 that is a wire, electrical lead, connection, electrical contact or the like that is attached at one end to a detection unit for transmitting electrical signals to and from an electrode substrate 14, which is an example of a conductive substrate or conductor as described herein. Nanoelectrodes 16, as described herein are attached to the electrode substrate 12. Depicted in FIG. 1A is one embodiment of an electrode 10 having a nanoelectrode array or ensemble having the nanoelectrodes 16 on one side of the electrode substrate 14, as in a biosensor "chip." FIG. 1B is a schematic cross-section of an electrode 10 having a nanoelectrode array or ensemble having the nanoelectrodes 16 on more than one side of the electrode substrate 14 although the actual topology and three-dimensional configuration can vary greatly, including different patterns, nanoelectrode quantities and shapes, electrode substrate compositions, shapes and substrates. For example and without limitation, the conductive substrate can be spherical, ovoid, triangular, cylindrical, conical, or other simple or complex shapes or combinations of shapes. The nanoelectrodes can be patterned on one side or all sides of the surface of the electrode substrate, or portions thereof. As depicted in schematic cross-section in FIG. 1C, the electrode substrate 14 can form a tubular structure having the nanoelectrodes on an internal surface (lumen) of the tube, permitting a flow-through configuration. In FIG. 1C, nanoelectrodes 16 can cover all or part of the internal surface of the electrode 10, only one layer of which is depicted for clarity in FIG. 1C. Typical, though non-limiting nanoelectrode compositions include gold nanowires, carbon nanotubes, platinum nanowires, silicon nanotubes, polyaniline/poly(acrylic acid) (PAN/PAA), block copolymers of PAA and polystyrene (PS-β-PAA), and prussian blue have shown utility in formation of nanoelectrodes, nanoelectrode arrays and/or nanoelectrode ensembles. Single electrodes comprise a lead wire attached to a nanoelectrode and are not shown due to their simplicity.

The electrode system, typically with the biological components immobilized onto its surface (herein referred to as the "electrode assemblies"), also contains a reference, such as an Ag/AgCl electrode and an auxiliary electrode such as a Pt wire, is connected to an electronic and/or a computing device to obtain and, optionally, analyze data in the form of an electric current generated by the biological assembly. Electrode assemblies can be configured within a chamber, such as a Faraday box for minimizing electrical noise, a reaction cell, or a flow-cell or any other container that can be inserted (plugged into) a device for connecting the chamber to an electronic or computer device for depicting and, optionally, analyzing the data generated by the electrode. A reaction cell is a container that comprises components for carrying out the biomarker detection method, and may include a nanoelectrode, macroelectrode, or arrays. A reaction cell may comprise a substrate for a redox reaction for use in the methods described herein, a nanoelectrode such as those described herein, and a counter electrode to complete an electrical circuit. A large variety of workstations are available that are capable of amplifying and reading or otherwise obtaining current readouts from the electrode assembly and analyzing them by a variety of methods. Workstations can have varying degrees of automation, and can employ robotics and fluidics as is necessary and/or desirable, to implement a detection assay for an analyte in a biological sample. Two examples of useful workstations are an Epsilon Electrochemical Workstation from BASi (West Lafayette, Ind.) and an Autolab PGSTAT electrochemical analysis station from EcoChemie (the Netherlands). Various analytical methods can be used to detect and analyze signals generated by the electrodes, such as, without limitation, cyclic voltammetry and differential pulse voltammetry. Generally, any workstation and analytical method capable of quantifying an analyte via detection of electrochemical, optical, mass, refractive index or other changes as the signal being detected in a given electrode/nanoelectrode/assay combination will be useful in performing the assays described herein.

Carbon nanotubes (CNTs) are of great utility, particularly when they are highly ordered and vertically aligned as in arrays. These geometrical parameters are advantageous for bio-functionalization and bio-sensing applications (Shim, M., Kam, N., Chen, R., Li, Y., Dai, H., 2002. Nano Lett. 2, 285-288; Sotiropoulou, S., Chainiotakis, N., 2003. Anal. Bioanal. Chem. 375, 103-105; Tsang, S., Chen, Y., Harris, P., Green, M., 1994. Nature 372, 159-162; Wang, S., Zhang, Q., Wang, R., Yoon, S., 2003. Biochem. Biophys. Res. Commun. 311, 572-576; Wang, S. Zhang, Q., Wang, R., Yoon, S., Ahn, J., Yang, D., Tain, J., Li, J., Zhour, Q., 2003. Electrochem. Commun. 5, 800-803; Yang Y., Wang Z., Yang M., Li J., Zheng F., Shen G., Yu R., 2007. Analytica Chimica Acta 584, 268-274) as they exhibit high conductivity and can be modified with site specificity (Withey, G. D., Lazareck, A. D., Tzolov, M. B., Yin, A., Aich, P., Yeh, J. I., Xu, J., 2006. Biosensors and Bioelectronics 21 (8), 1560-1565 and Taft, B., Lazareck, A., Withey, G., Yin, A., Xu, J. M., Kelley, S. O., 2004. J. Am. Chem. Soc. 126(40), 12750-12751) as their closed sidewalls and open ends exhibit inherently different physical and chemical properties (Saito, R., Dresselhaus, G., Dresselhaus, M. (Eds.), 1998. Physical Properties of Carbon Nanotubes. Imperial College Press, London, UK and Dresselhaus, M., Dresselhaus, G;. Avouris, P. (Eds.), 2001. Carbon Nanotubes: Synthesis, Structure, Properties, and Applications. Springer, Berlin).

In one non-limiting embodiment, a plurality of nanoelectrodes is aligned substantially parallel relative to one another on a conductive substrate and substantially perpendicular to the substrate. A PNA is attached to a first end of at least a portion of the plurality of nanotubes. Suitable substrates responsive to an electrochemical signal include electrodes. The term "electrode" refers to an electrical conductor that transduces a current in and out of, or to and from, an electrically conducting medium or source, which, in the context of the present disclosure is to and from a biosensor placed in a solution or sample or in situ in a cell/organism. The electrode may be an array, comprising a number of individually-addressable electrodes. The electrode comprises an electrically conductive material. For example, gold, copper, carbon, tin, silver, platinum, palladium, indium tin oxide (ITO) or combinations thereof. Among these materials, because of excellent electrical conductivity and chemical stability, gold, tin oxide, and especially carbon electrodes may be preferable, depending upon the end use and the desired properties of the electrode. It is to be understood that as used herein, a "layer" may have a variety of configurations, for example rectangular, circular, a line, an irregular dot, or other two- or three-dimensional configuration. One non-limiting example of a suitable electrode is a gold disk electrode.

Linkage between CNTs and enzymes via PNAs, metal-containing PNAs or other PNA-protein combinations provides one means of assembling the various components, for instance, in accessing and aligning to an enzyme's active site. For example and without limitation, NADH peroxidase (Npx) enzyme exists in the thiolate state under reducing conditions of the reaction to form the bioassembly. The activity (Poole, L. B., Claiborne, A., 1986. J. Biol. Chem., 261, 14525-145233 and Parsonage, D., Miller, H., Ross, P. R., Claiborne, A., 1995. J. Biol. Chem. 268, 3161-3167) of the enzyme can be determined prior to assembly formation to ascertain the reduced state of the cysteine and competency for disulfide bond formation under all conditions, including in the presence of GnHCl and PNA.

To form the linkage between Npx and the PNA, oxidation to form a disulfide (or a thioester bond, depending on the functional group synthesized) can be catalyzed by hydrogen peroxide under mild conditions. If the concentration of hydrogen peroxide is in excess, the peroxide could potentially oxidize the Npx Cys-sulfenic acid (Cys-SOH, secondary redox center) further to Cys-sulfinic (Cys-SO$_2$H) and/or -sulfonic acid (Cys-SO$_3$H), oxidation states that are unable to react with PNA's Cys-thiol group (Yeh, J. I., Claiborne, A., 2002. In: Sen, C. and Packer. L. (Eds.), Methods in Enzymology. Academic Press, New York, N.Y., 353, 44-45; Claiborne, A., Mallett, C., Yeh, J. I., Luba, J., Parsonage, D., 2001. Advances in Protein Chemistry 58, 215-276 and Claiborne, A., Yeh, J. I., Mallett, T. C., Luba, J., Crane, E. J., Charrier, V., Parsonage, D., 1999. Biochemistry 38, 15407-15416). Thus, the amount of hydrogen peroxide should be controlled and limited to a quantitative ratio of Npx in order to maximize Npx-PNA formation.

Nanoelectrodes can be manufactured in a variety of ways. In one non-limiting embodiment, a carbon or platinum fiber is attached to a wire, such as a copper wire. Single carbon fiber nanoelectrodes can be prepared by flame etching or electrochemical etching. Single electrodes can be inserted into a glass capillary and sealed, for instance with epoxy resin to produce a useful probe.

Individual nanoelectrodes have their uses for in situ and intracellular monitoring. Their disadvantage is that they generate an extremely small current. Therefore it is desirable to produce an electrode comprising a plurality or nanoelectrodes capable of operation in parallel, namely ensembles and arrays of nanoelectrodes (NEE and NEA, respectively). NEEs can be prepared by various approaches.

Single biosensors or electrodes can be used not only in detecting an analyte in vitro, but in situ in a cell or organism. In situ use can benefit from a suitable bionanoneedle structure in which the nanoelectrode is used to penetrate a cell or skin of an organism to place the biosensor at a desired location. Generally, a single nanoelectrode needle can be a smooth needle-shaped carbon nanotube or platinum fiber. The diameter of the single nanoelectrode tip is from several nanometers (e.g., CNT, for example and without limitation, to multiple walled CNT) to hundreds of nanometers (e.g. fibers). Moreover, the surface of the single electrode is quite smooth, which results in excellent electrochemical characteristics (such as increasing the ratio of signal/noise and allowing the high scan rate for their low-charged currents) and high sensitivity in the electrochemical detection. Single nanoelectrodes can be functionalized with biological components, as described above for nanoelectrode arrays, to fabricate "bionanoneedles". The main difference in the bionanoneedles versus a biofunctionalized nanoelectrode array is the dimensionality whereby a nanoneedle is less that 50 nm in diameter and more typically ~20 nm in diameter. This is $10^2$-$10^3$ smaller in diameter than prokaryotic or eukaryotic cells. Consequently, these bionanoneedles can have the capability of interrogating cellular content at the single cell level, permitting unprecedented investigations and quantitation of cellular components.

Figure 2A:
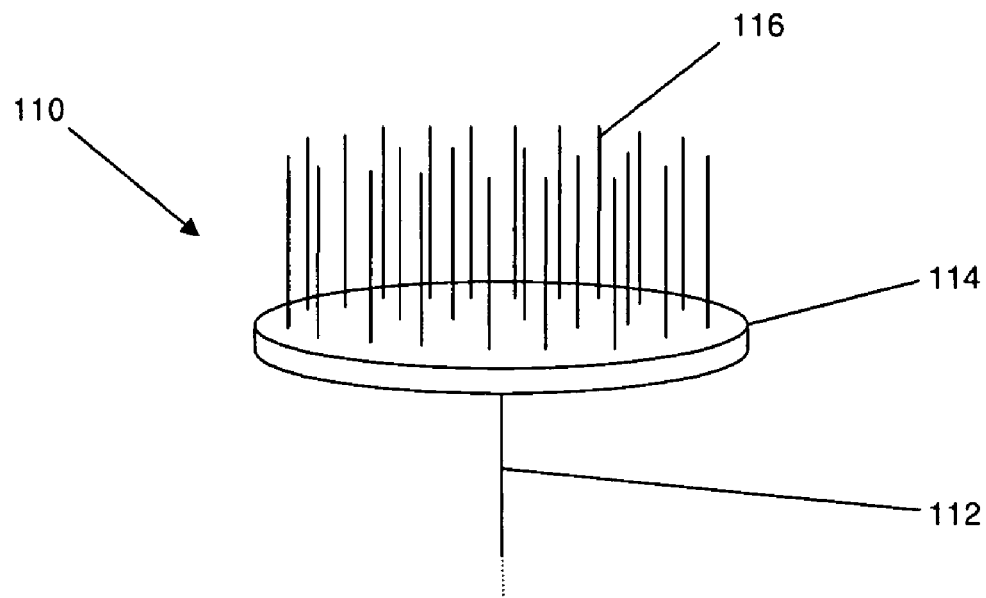
FIG. 2A shows schematically a bionanoneedle array.
Figure 2B:
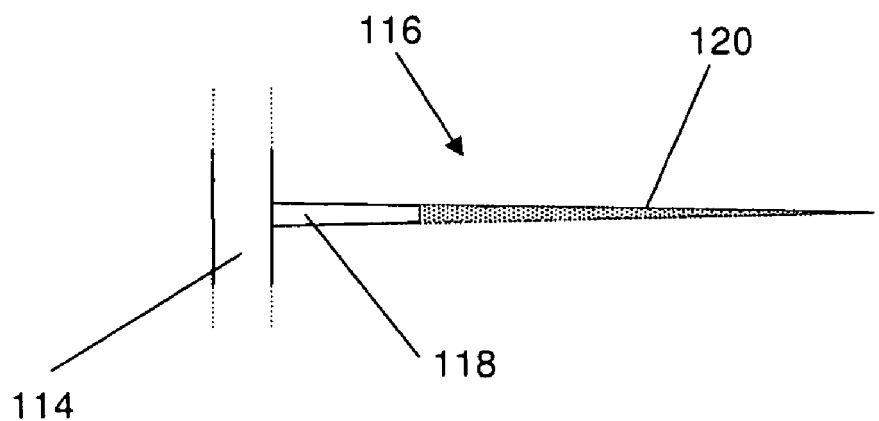
FIG. 2B shows schematically a single bionanoneedle of FIG. 2A.

Bionanoneedles also have sufficient structural strength to penetrate protective layers, such as membranes, permitting their use in detecting analytes in an organism and, in instances where the biological component of the nanoneedle does not require regeneration, continuous detection of the analyte over time. Indeed, in systems that require regeneration (e.g. the binding reagent/redox tag system described herein), the bionanoneedle only can be used over a (calibrated) fixed time because over time the in situ analyte typically will replace all of the redox tag. An array of bionanoneedles would be suitable for this use, as the multiplicity of needles would generate a stronger signal. FIG. 2A shows schematically a bionanoneedle array 110 in the form of a disk or patch. Array comprises a conductive lead(s) 112, electrode 114 and bionanoneedles 116. FIG. 2B shows schematically a single bionanoneedle 116 of FIG. 2A in which nanoelectrode 118, for example and without limitation, a CNT, is attached to electrode 114 and comprises a region or portion 120 which comprises one or more nanosensors, as described herein, which comprise a PNA linker. In certain non-limiting embodiments, the needles are arrayed substantially parallel to each-other (see FIG. 2A) on a disk-shaped conductor (electrode) that can be placed against the skin or mucous membrane. The bionanoneedles should be of sufficient length to accomplish their task, for example of passing through skin or mucosa, typically at least about 2-5 mm for both skin and mucosa in an organism, or through a cell membrane of a cell.

Several methods have proved to be successful in preparing NEEs. In "templated synthesis", metal fibers are grown electrochemically or chemically to fill the pores of a template membrane. For example, metal cylindrical nanotubes, conical nanotubes and nanowires have been synthesized using porous templates, such as polycarbonate, polyester and alumina membranes. For the deposition of gold nanofibers with diameters as small as 10 nm, Menon and Martin developed an electroless plating procedure (Menon et al., *Anal. Chem.* 67:1920-1928 (1995)), which has also been applied successfully by others. Other approaches are based on the defects generated in self-assembled mono layers, exploiting these as NEEs (Sabatini et al., (1987, J. Phys. Chem. 91:6663-6669; Chailapakul et al. (1993, *J. Am. Chem. Soc.* 115:12459-12467) and Che et al. (1996), *J. Electroanal. Chem.* 417:155-161.).

Recently, Hu et al. reported a one-step approach to glassy carbon (GC) NEEs with pores of approximately 20-120-nm radii using an amphiphilic block copolymer polystyrene-block [-PS-b]-poly(acrylic acid) (PAA) self-assembly (Wang et al. 2007, *Talanta* 71:178-185). This procedure required conventional, inexpensive electrochemical instrumentation. PS-b-PAA was dissolved in tetrahydrofuran, with a typical concentration in solution of 0.1% by weight. A drop of PS-b-PAA-tetrahydrofuran solution was spin-cast onto the polished GC electrode surface in a humid atmosphere (approximately 50% relative humidity) with air flow across the surface. After several seconds, the whole surface of the electrode was covered with a translucent layer. The thin film consists of a 1-μm thick film with pores of approximately 20-120-nm radii.

Jin et al. used porous sol-gel (PSG) film as a template for the electrochemical polymerization of aniline in the presence of PAA (Xian et al. (2007) *Electrochem. Commun.* 9:773-780). An ordered polyaniline (PAN)-PAA composite was prepared by electropolymerization of aniline in the presence of PAA with PSG as a template. A PSG-coated GC electrode was cycled in a solution of distilled aniline, PAA, $H_2SO_4$ and $Na_2SO_4$ during the cyclic voltammetry. The resulting modified electrode was then washed with the background electrolyte solution of $H_2SO_4$ and $Na_2SO_4$ to exclude any residual monomer. The PAN/PAA fibers were about 100±25 nm in apparent diameter, ranging in height from 30 to 50 nm. In addition, the conductive polymer is highly ordered. The densities and sizes of the nanoelectrodes can be controlled easily using electrochemical methods. The conductive polymer 'wires' of PAN-PAA formed in the PSG matrix can behave as an ensemble of closely spaced but isolated nanoelectrodes. Owing to the biocompatibility of PSG and the electroactivity of PAN-PAA at neutral pH, the NEEs are suitable for modification with biomolecules to fabricate nanobiosensors.

In the past decade, there has been intense interest in the fabrication of 3D nanostructured ensembles for broad applications in the development of various nanobiosensors. The small surface area of the NEEs can be increased in a controlled way by suitable etching, in order to partially remove the upper layers of the polycarbonate template membrane. This causes the structure of the final ensemble to change from a flat 2D surface made of metal nanodiscs imbedded into the polycarbonate to a 3D structure made by an ensemble of nanotubes or nanowires protruding partially from the polycarbonate insulating layer. 3D NEEs were obtained from 2D NEEs by two different etching procedures: one with $O_2$/Ar plasma (Yu et al. (2003) *Nano Lett.* 3:815-818; Gasparac et al. (2004) *J. Am. Chem. Soc.* 126(39):12270-12271 and Lapierre-Devlin et al. (2005) *Nano Lett.* 5(6):1051-1055) and the other using a solvent mixture of dichloromethane and ethanol as a chemical-etching agent (Krishnamoorthy et al. (2005) *Anal. Chem.* 77:5068-5071).

Martin et al. first proposed $O_2$ plasma as a way for achieving the controlled removal of polycarbonate (Yu et al. (2003) *Nano Lett.* 3:815-818). They fabricated the 3D NEEs using gold electro less deposition in polycarbonate membranes followed by $O_2$ plasma-etching. Plasma-etching resulted in consistent exposure of approximately 200 nm of the gold nanowires. They suggested that the 3D NEE architecture of the nanowires could facilitate the electro catalytic reaction because of enhanced diffusion around the nanofibers.

Instead of the plasma approach, Zoski et al. proposed substituting the plasma-etching with a chemical-etching method based on the partial dissolution of the polycarbonate membrane in suitable solvent mixtures (Krishnamoorthy et al. (2005) *Anal. Chem.* 77:5068-5071). A solvent ratio of 50:50 dichloromethane/ethanol was optimal for selective and controlled etching of the surface layers of the polycarbonate membrane to expose up to 200-nm lengths of gold nanowires. After chemical etching, in spite of the expected increase of active area, double-layer charging current did not increase significantly with respect to 2D NEEs. However, the Faradaic current for a reversible redox probe (e.g., ferrocenemethanol 10 mM) increases with the etching of the NEE surface.

Similar to 2D or 3D NEEs, NEAs can produce a much higher current than a single nanoelectrode, which can circumvent the need for expensive electronic amplifiers to improve the signal:noise ratio. The NEAs also have more practical values as ultrasensitive electrochemical sensors for chemical and biological sensing. CNTs have received much attention from an electroanalytical and biosensing viewpoint. There are two main types of CNT that have high structural perfection: single-walled CNTs (SWCNTs) and multiwalled CNTs (MWCNTs). The attractiveness of CNTs as molecular wires is that they can be metallic or semiconducting, are small, rigid and simple to produce in large quantities. CNTs also have many interesting properties, such as fast electron transfer rate and high electrocatalytic activity. In addition, CNTs can be functionalized with different biomolecules, such as DNA and proteins. Furthermore, vertically aligned CNTs have good materials properties and are of the right size (~20-200 nm) to be NEAs. CNT forest electrodes have been reported for biosensor application (see, e.g., United States Patent Application No. 2006/0240492 to Rusling et al. describing arrays of single wall carbon nanotubes (SWNTs) and methods of making the same. Carbon nanotube (CNT) "forests" can be deposited/grown/patterned in any desirable configuration). However, the CNT forest electrodes do not act as individual nanoelectrodes due to the high density of the CNT forest. A more optimal spacing requires the center-to-center distances of CNTs to be sufficiently larger than the diameter of the nanotube, such that each nanotube works as an individual electrode.

Consequently, in the fabrication of NEAs, certain important requirements should be met. First, the interspacing of the individual electrodes should be much larger than the radius of each electrode, otherwise the closely packed NEAs will behave similarly to a macroelectrode owing to the diffusion-layer overlap. Second, there must be a sufficient passivation layer that can protect the underlying conducting layer as well as prevent current leakage and corrosion. Both inorganic materials, such as $SiO_2$ and $Si_3N_4$, and organic materials, such as epoxy and photo resist, have been tested previously (Faβbender et al. (2000) *Sens. Actuators B* 68:128-133). The ideal passivation layer is captive and crack-free, is long lasting in aqueous electrolyte solutions, possesses good adhesion to substrates and electrodes, is strong mechanically and is processed easily.

Li et al. reported an approach for the fabrication of NEAs using vertically aligned MWCNTs embedded within a $SiO_2$ matrix (Li et al. (2003) *Nano let.* 3(5):597-602; Koehne et al. (2003) *Nanotechnology* 14:1239-1245; Koehne et al. (2004) *Mech. Chem. Biosyst.* 1(1):69-80 and Koehne et al. (2004) *J. Mater. Chem.* 14:676-684). This platform can be used widely in analytical applications as well as fundamental electrochemical studies, such as DNA nanobiosensors. Using this method, it was possible to prepare NEAs with an extremely low density of sites (i.e., of individual CNTs). Such low density offers advantages to electroanalysis because it incorporates enhanced mass transport to each CNT in the array and also has a lower charging current. The important advantage in this method is that the spacing between individual CNTs is controllable and thus the electrochemical properties can be manipulated. The fabrication method is based on the growth of CNTs at nickel-catalyst sites across the surface and the arrangement of catalyst deposits controlled the geometry of the eventual CNT NEAs. The space between individual CNTs could be filled with a suitable insulator material, such as $SiO_2$. The radii of individual CNTs in the resulting array were 17 nm, whereas the average inter-CNT spacing was 1.3 µm for the low-density NEAs. This method could prepare NEAs with an extremely low density of sites, such as individual CNTs. Such low density of NEAs offers advantages to electroanalysis because it incorporates the enhanced mass transport to each CNT in the array and also has a lower charging current. The CNT NEAs can be used widely in analytical applications, such as DNA nanobiosensors.

CNT NEAs have also been fabricated through the method of self-assembled matrix by Gooding et al. (Liu et al. (2005) *Electroanalysis* 17(1):38-46). The aligned SWCNT arrays were created and controlled through a self-assembly method and used to achieve direct electrical connection to glucose oxidase. In this method, gold electrodes were first modified with a self-assembled monolayer of cysteamine. The shortened SWCNTs were then aligned to the gold electrode surface by self-assembly. The surface density of tubes in this study was $2 \times 10^{13}$ tubes/cm$^2$ and was in excess of the density required for tubes to act as individual nanoelectrodes (Li et al. (2003) *Nano let.* 3(5):597-602; Koehne et al. (2003) *Nanotechnology* 14:1239-1245; Koehne et al. (2004) *Mech. Chem. Biosyst.* 1(1):69-80 and Koehne et al. (2004) *J. Mater. Chem.* 14:676-684). The electrochemical experiment results also indicated that the diffusion layers of neighboring SWCNT electrodes overlap, such that the entire aligned SWCNT-modified electrode acts as a macroelectrode. Thus, an important target for future fabrication of CNT NEAs by the self-assembly method is to lower the CNT densities on the electrode surface. These are promising because the more-electro active ends of the CNTs are readily accessible to species in solution and the rigidity of the tubes enables them to be "plugged into" biomolecules, which enables electrical connection to the redox centers of the biomolecules. Subsequently, the CNTs were plugged into glucose oxidase in one of two ways. In the first method, native glucose oxidase was attached covalently to the ends of the aligned CNTs, which enabled the close approach to flavin adenine dinucleotide (FAD) and direct electron transfer to be observed with a rate constant of 0.3 s$^{-1}$. In the second strategy, FAD was attached to the ends of the nanotubes and the enzyme reconstituted around the surface-immobilized FAD. The latter approach enabled more efficient electron transfer to the FAD with a rate constant of 9 s$^{-1}$. This provides a potential application of this kind of CNT NEA in fabricating glucose nanobiosensors.

Besides CNTs, other nanostructured materials are also used to fabricate NEAs. Metal platinum is one of the most studied noble metals; its potential applications have been demonstrated in the fields of biosensors, catalysts and fuel cells. Yu et al. synthesized a platinum nanowire array in polycarbonate membranes by means of a direct electrodeposition technique directly on a GC electrode (Yang et al. (2006) *Biomaterials* 27:5944-5950). The diameter of each nanowire was approximately 250 nm and the height was approximately 2 µm. The nanowire array prepared by this proposed method can be considered as a NEA with a nanoelectrode density of $5 \times 10^8$ cm$^{-2}$ with each nanowire acting as an individual nanoelectrode. The nanostructure properties of the platinum NEAs can improve the signal:noise ratio and decrease the detection limit. Moreover, the electroactive surface area of the platinum NEAs was approximately six-times larger than the conventional platinum electrode and circumvented the problem of conventional platinum electrodes associated with the limited electroactive site. For example, this platinum NEA was used to detect $H_2O_2$ and the direct response of the NEA can be achieved at low potential of 0 V with a sensitivity of 50-times more than that of the conventional platinum electrode. The high sensitivity of the NEA toward $H_2O_2$ and the large surface area illustrate its ideal application to the absorption of enzymes to fabricate nanobiosensors.

Owing to the many functional groups on the surface of silicon, such as Si—H and Si—O, it might provide good biocompatibility and can be grafted with other functional groups. Thus, silicon nanotubes (SiNTs) have also been used for the fabrication of NEAs. Shao et al. reported a multistep produce a highly ordered SiNT array and demonstrated that such a SiNT array displayed excellent field-emission properties (Mu et al. (2005) *Appl. Phys. Lett.* 87:113104(1-3) and Mu et al. (2007) *J. Phys. Chem. B* 111: 1491-1475). The average outer-pore diameter was approximately 70 nm, the wall thickness was approximately 10 nm and the nanotube length was approximately 20 µm. The possibility of the SiNT array as an electrode was studied by determining the electrochemical behaviors of redox proteins. The experimental results demonstrate that the hollow structures of SiNT arrays can provide a molecular channel to let the protein arrive easily at the electrode surface and the surfaces of the inner wall of the SiNTs possess good biocompatibility. The feasibility of the chemical-modification approach can be assessed by the maintenance of the activity of the biomaterial. These studies show that SiNT arrays are promising as biosensors for protein characterization.

Prussian blue (PB) is a well-known coordination compound studied extensively in basic and technologically oriented research. PB has been used recently in a new range of applications, including NEA fabrication (Itaya et al. (1982) *J. Am. Chem. Soc.* 104:4767-4772 and Ricci et al. (2005) *Biosen. Bioelectron.* 21:389-407). Jin et al. proposed a strategy to form high-aspect ratio of PB NEAs by electrochemical deposition of the PB through highly ordered porous anodic alumina membrane (Xian et al. (2007) *Biosen. Bioelectron.* 22(12):2827-2833). The porous anodic alumina membrane with a specified pore diameter of 200 nm was used as the template material for PB array fabrication. A thin layer of gold was deposited by vacuum evaporation onto the branched side of the porous anodic alumina template, followed by electrodeposition of PB. After deposition, the porous anodic alumina has a highly ordered pore arrangement with an average pore diameter of approximately 200 nm. The diameter of PB nanotubes corresponds well to the diameter of nanoholes in porous anodic alumina. Since the highly ordered PB arrays can behave as an ensemble of closely spaced but isolated nanoelectrodes, the nanostructured PB might be used potentially to fabricate nanobiosensors.

Some magnetic nanowires (e.g., Fe or Ni nanowires) have also been used for the development of nanoelectrode platforms (Hirsch et al. (2000) *J. Am. Chem. Soc.* 122:12053-12054; Weizmann et al. (2003) *J. Am. Chem. Soc.* 125:3452-3454; Weizmann et al. (2005) *J. Am. Chem. Soc.* 127:12666-12672 and Wang et al. (2006) *J. Am. Chem. Soc.* 128:4562-4563). Magnetic nanowires demonstrate unique anisotropic behavior correlated to their shape; high remnant magnetization makes suspended nanowires highly orientable and manipulated easily in small external magnetic fields. This property can be used to control the nanowires to obtain highly ordered structures. Additionally, the nanowires can be functionalized to fabricate nanobiosensors (Hirsch et al. (2000) *J. Am. Chem. Soc.* 122:12053-12054; Weizmann et al. (2003) *J. Am. Chem. Soc.* 125:3452-3454; Weizmann et al. (2005) *J. Am. Chem. Soc.* 127:12666-12672 and Wang et al. (2006) *J. Am. Chem. Soc.* 128:4562-4563).

In one embodiment of the present disclosure of a biosensor, a competitive assay is described herein in which a binding reagent such as an antibody or a receptor, is linked to an electrode via a PNA linker. The PNA linker contains typically, but without limitation, a metal or other electron transfer group in order to increase the electron transfer capacity of the PNA and to produce a PNA "nanowire". The functionality of the biosensor depends on the binding association of the biosensor with a reagent or analyte that has the capacity to create electron flow (current) within the biosensor when bound to the biosensor. In one non-limiting embodiment, current can be created by binding a redox enzyme to a biosensor comprising a binding reagent forming a binding pair with an epitope that is conjugated, typically covalently, to the redox enzyme to produce a redox tag. The redox tag is produced by conjugating a binding partner of the reagent within the biosensor to a redox enzyme. The binding partner can be conjugated, typically covalently linked, by any chemical method useful for conjugating proteins (see, e.g., Crosslinking Reagents Technical Handbook, No. 1601361, March 2006, Pierce Biotechnology, Inc., Rockford, Ill.), typically by use of a suitable reagent such as, without limitation N-ethyl-N-(dimethylaminopropyl) carbodiimide (EDC), N-hydroxysuccinimide (NHS) and ethanolamine-HCl. The redox tag may be prepared also by synthesizing a chimeric protein comprising both the redox enzyme and the binding partner, as is possible with glucose oxidase ("GOx", see, e.g., United States Patent Application No. 2004/0053425, which is incorporated herein by reference in its entirety for its technical disclosure). In use, the redox tag is bound to the biosensor and is contacted in solution with its redox substrate (e.g., glucose for a GOx-based redox tag), thereby generating a signal transmitted by the biosensor to the nanoelectrode. When an analyte containing the same epitope as that of the redox tag is introduced in the solution, it displaces the redox tag, thereby decreasing the signal output. After calibration of this system using known quantities of the analyte, the concentration of the analyte in a biological sample can be determined, as in the case of PSA, shown in the Examples below.

As shown below, in one non-limiting embodiment, the binding reagent is anti-PSA antibody or other anti-PSA binding reagent, and the redox tag is a part or complete PSA bound to a GOx enzyme. When a biological sample comprising PSA is analyzed, a decrease in signal caused by the competition of the PSA in the sample with the PSA/GOx redox tag can be used to quantify the PSA present in a sample. Once used, the biosensor can be regenerated with PSA/GOx by washing at a suitable pH or under other conditions to cause release of the PSA/GOx and bound PSA from the biological sample, and by then adding sufficient quantities of PSA/GOx to bind substantially all of the biosensors.

Example 1

Biosensor for Detection of PSA Using a GOx-Based Redox Tag

Materials and Chemicals

Prostate specific antigen (PSA) and goat polyclonal PSA antibody were purchased from RD&D. Glucose oxidase (GOx) from *Apergillus niger* was purchased from Sigma. A 10 μM solution of 8-hydroxyquinoline-containing PNA oligomer (NH-LysCCGTQ$_1$ACGG-H) was annealed by slow cooling in a pH 7 10 mM buffer in the presence of one equivalent of Cu$^{2+}$ N-ethyl-N-(dimethylaminopropyl) carbodiimide (EDC), N-hydroxy-succinimide (NHS) and ethanolamine-HCl were purchased from Sigma. All other chemicals were products of Sigma.

Fabrication of PSA Biosensor

Figure 3A:
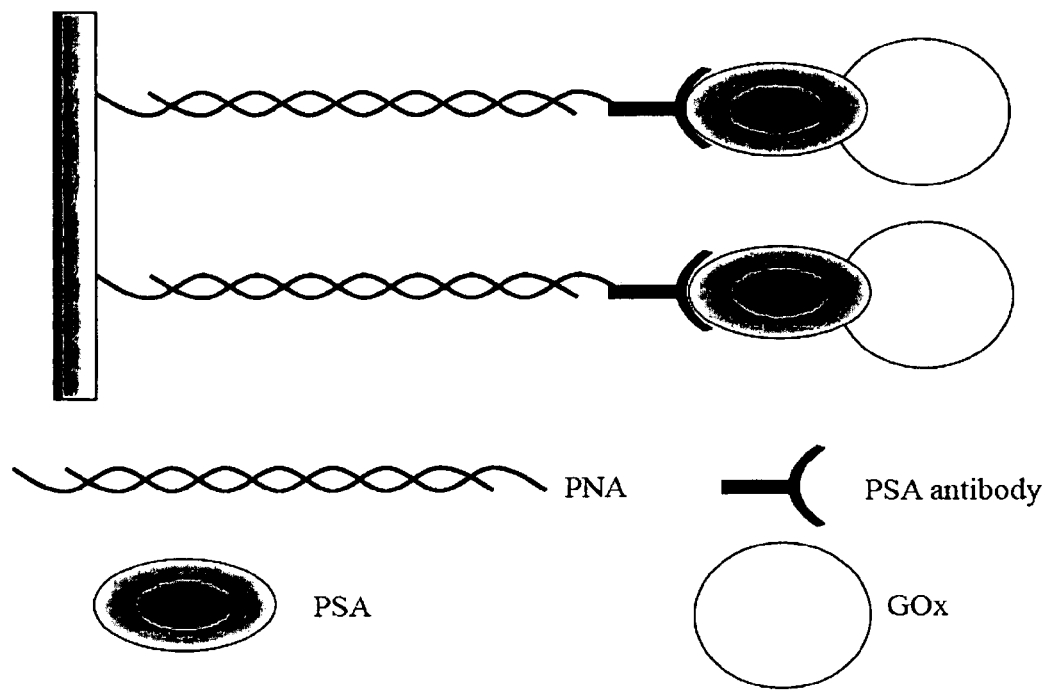
FIGS. 3A and 3B schematically show non-limiting embodiments of a PSA biosensor.
Figure 3B:
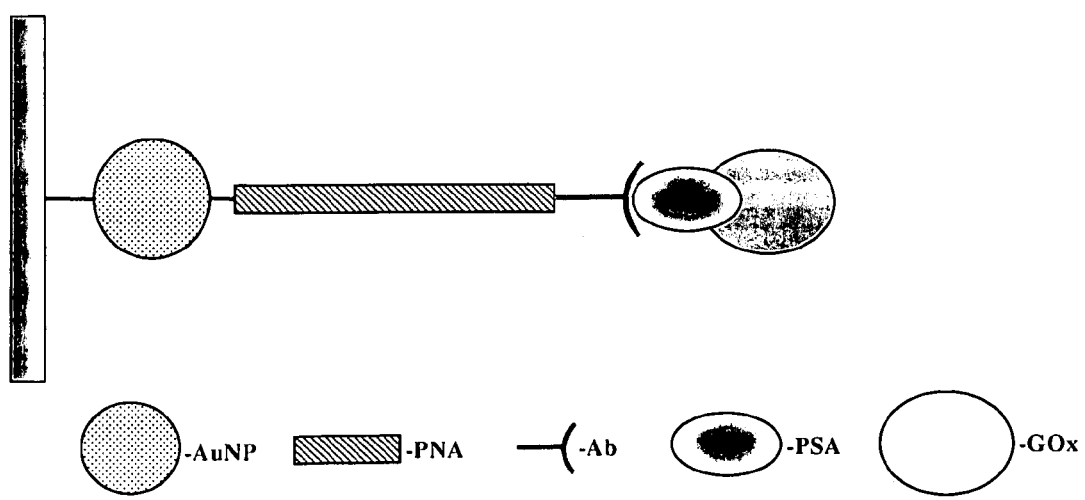

The gold disc electrode (diameter: 1.6 mm) was polished using 0.05 μm alumina slurry and sonicated in water for 10 min. Then the electrode was treated electrochemically in 0.1 M H$_2$SO$_4$ by scanning the potential from 0 to 1.5 V at 100 mV/s for 15 min. The gold electrode was pretreated overnight with 10 mM 3-mercaptopropionic acid (in ethanol) at 4° C. The pretreated gold electrode was washed with ethanol followed by water, and then further treated with EDC/NHS mixed solution at 4° C. for 30 min. Then the electrode was reacted with the solution of PNA to immobilize PNA on the electrode surface. The PSA-antibody was reacted with EDC/NHS mixture for 30 min to form an activated ester and then was added to the PNA-modified electrode to create a peptide bond between the C terminus of the PSA-antibody and the PNA. The GOx was reacted with EDC/NHS mixture for 30 min and then mixed with PSA for 1 h to form a PSA-GOx complex. The PSA-antibody-modified gold electrode was immersed into PSA-GOx solution for 5 min and then used as PSA biosensor. FIG. 3A shows the schematic structure of the PSA biosensor. FIG. 3B shows another embodiment of a PSA biosensor that comprises gold nanoparticle ("AuNP").

Detection of PSA

The fabricated PSA biosensor can be used for detection of PSA directly. The PSA biosensor containing the PNA, PSA antibody, PSA, and GOx was immersed into a solution containing the PSA analyte for 5 min during which PSA replaced the PSA-GOx complex due to the difference in affinities (shown as Table 4). The concentration of the analyte PSA can be determined from the decreased peak current. After the detection of PSA, as a non-limiting example, the PSA biosensor can be regenerated using 10 mM glycine-HCl (pH 2.0) to wash the electrode for 2 min. Other non-limiting examples of regeneration buffers include 10 mM glycine-HCl, pH 3.0-1.5, 1-100 mM NaOH, 0.5-5 M NaCl, 1-4 M MgCl$_2$, 0.02-0.05% SDS, 50-100% ethylene glycol.

TABLE 4

Affinity of PSA or PSA-GOx complex to the PSA-antibody.

| | $k_a$ | $k_d$ | $K_A$ | $K_D$ | $\chi^2$ |
|---|---|---|---|---|---|
| PSA | $2.65 \times 10^4$ | $5.96 \times 10^{-3}$ | $4.46 \times 10^6$ | $2.24 \times 10^{-7}$ | 0.207 |
| PSA-GOx | $3.36 \times 10^4$ | $1.12 \times 10^{-1}$ | $2.99 \times 10^5$ | $3.34 \times 10^{-6}$ | 2.24 |

Instrument

Electrochemical experiments were performed on an Epsilon Electrochemical Workstation from BASi. The modified gold electrode was used as the working electrode, an Ag/AgCl electrode used as the reference electrode and a platinum wire electrode used as the auxiliary electrode. All the measurements were carried out in 20 mM phosphate buffer (pH 7.5).

Results

Figure 4A:
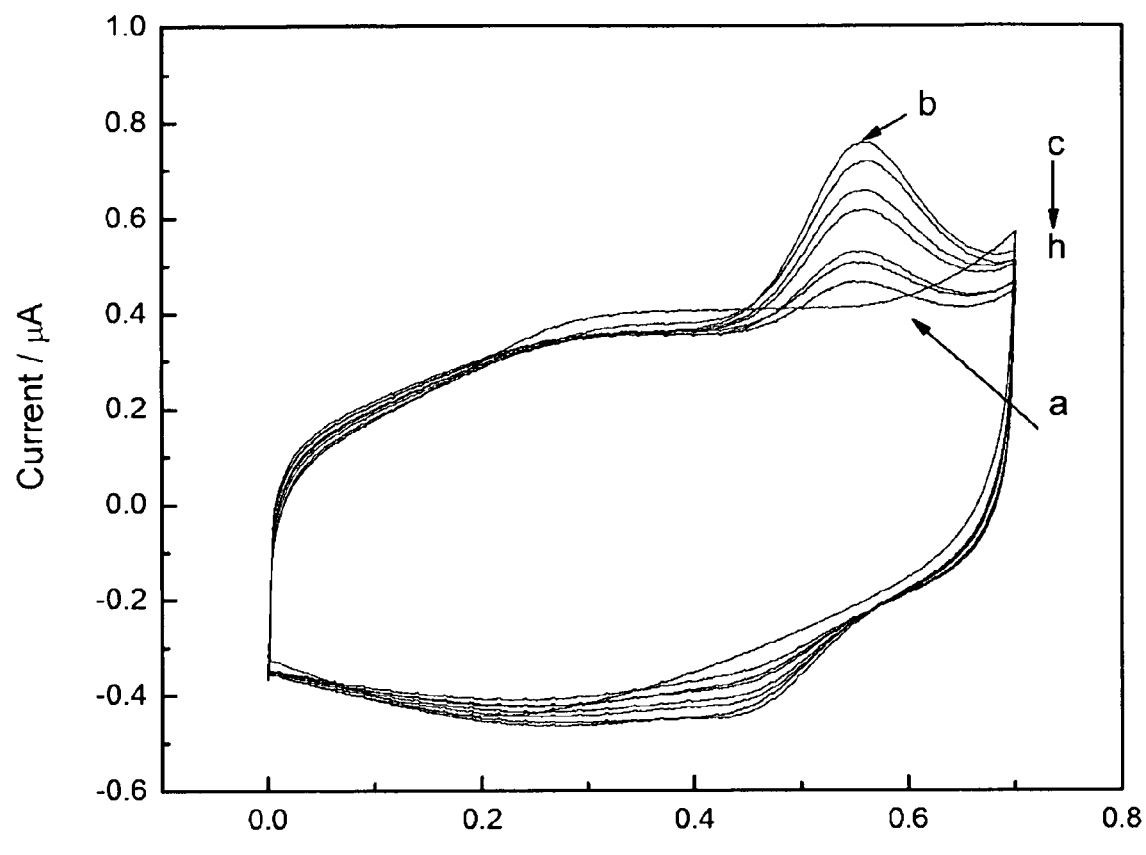
FIGS. 4A and 4B show electrochemical signals of a PSA biosensor for detection of PSA using cyclic voltammetry ("CV").
Figure 4B:
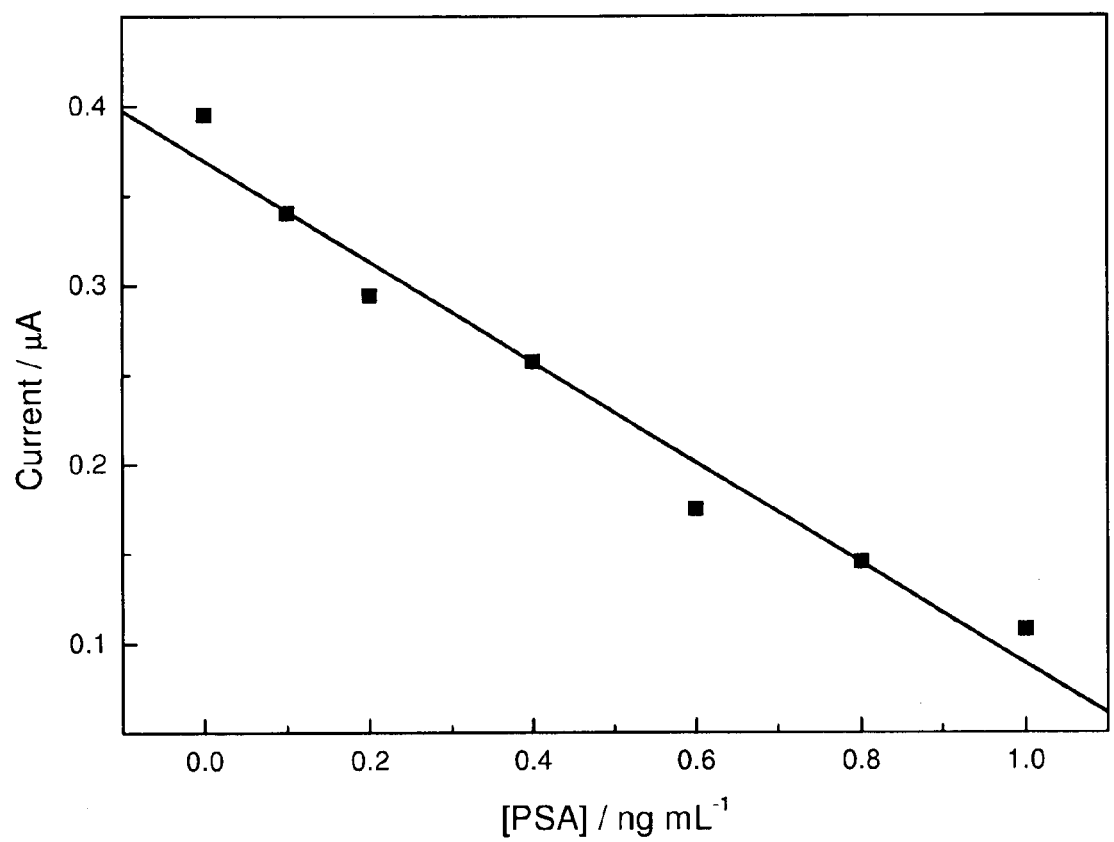

FIG. 4A shows cyclic voltammetry curves of the PNA/PSA-antibody assembled electrode before (curve a) and after (curve b) the binding of the PSA-GOx complex. The fabricated PSA biosensor was used for the detection of PSA at 0.1 ng/mL, 0.2 ng/mL, 0.4 ng/mL, 0.6 ng/mL, 0.8 ng/mL and 1.0 ng/mL (from curve c to curve h). FIG. 4B shows the dependence of the anodic current on the PSA concentration.

The results showed that the PSA-GOx complexes were successfully bound to the PSA-antibody. The results showed that the PSA-GOx complexes were partially replaced by PSA due to the higher affinity of the PSA-antibody for PSA. Consequently, the peak current decreased (shown as curve c to h in FIG. 4A) after the electrode was immersed in PSA solution of various concentrations and the decrease in current was proportional to the PSA concentration (shown in FIG. 4B).

Figure 5:
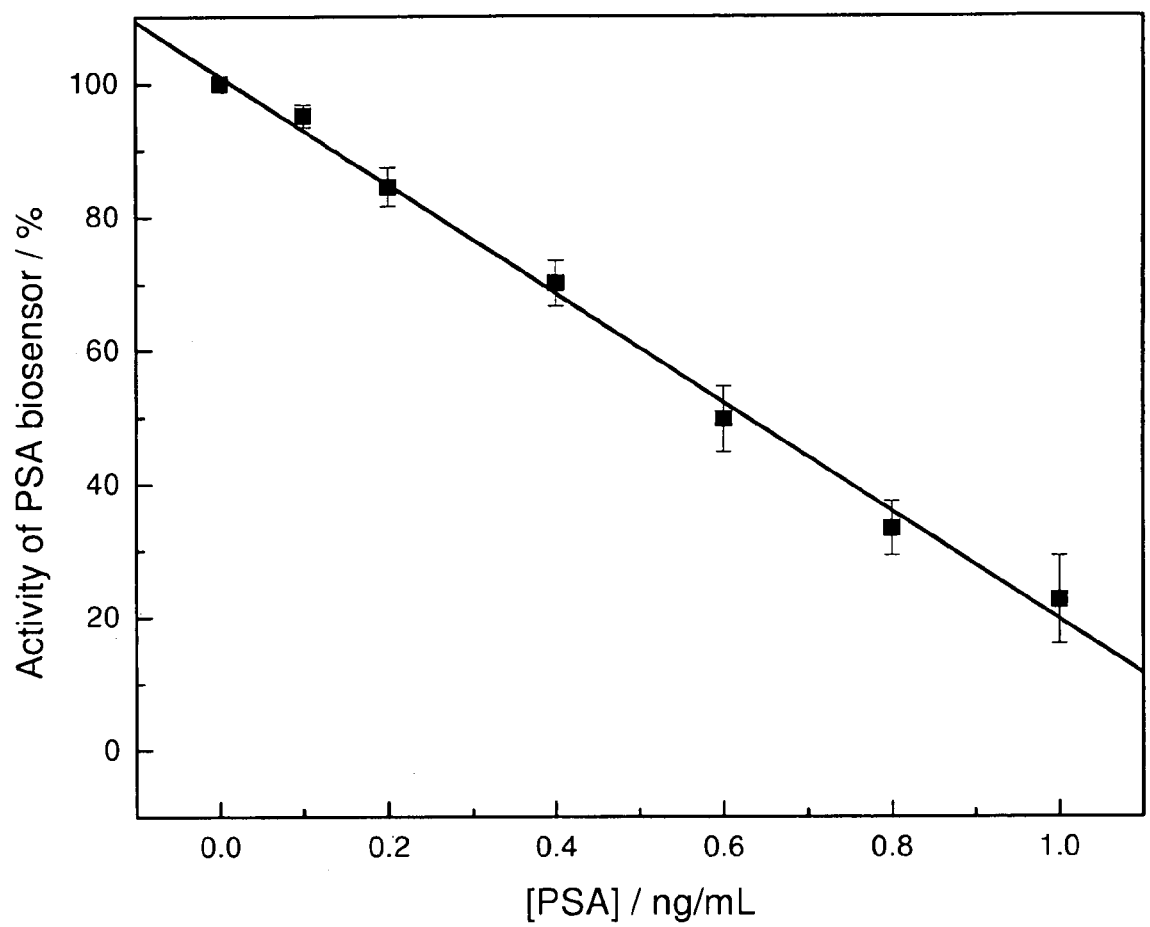
FIG. 5 is a graph showing the dependence of the electrochemical signals of PSA biosensors on PSA concentration. The error bars indicate the R.S.D. of three replicative measurements (n=3).

The electrochemical current of the PSA biosensors was plotted as a function of PSA concentration, as shown in FIG. 5. The PSA biosensor had a lower detection limit (0.1 ng/mL) than current electrochemical PSA biosensors. The error bars indicate the R.S.D. of three independent measurements (n=3) and the good reproducibility of the results measured with PSA biosensor is revealed in FIG. 5 and Table 5. These properties of the PSA biosensors determine a great potential of the biosensors for applications in clinical and medical tests.

TABLE 5

Quantitation of PSA Concentrations

| [PSA] ng/mL | Mean of activity of PSA biosensors (100%) | Standard deviation | n |
|---|---|---|---|
| 0.1 | 95.67845 | 1.34737 | 3 |
| 0.2 | 83.10795 | 2.10285 | 3 |
| 0.4 | 70.3735 | 2.11453 | 3 |
| 0.6 | 52.72759 | 3.53929 | 3 |
| 0.8 | 32.98292 | 4.81234 | 3 |
| 1.0 | 22.71766 | 7.78482 | 3 |

Conclusion

We have fabricated an electrochemical PSA biosensor using a metal-containing modified peptide nucleic acid (PNA) as the linker between the electrode surface and PSA antibody. The electrochemical detection of PSA was carried out using cyclic voltammetry and exhibited high sensitivity of 0.1 ng/mL and good reproducibility. The detection limit (0.1 ng/mL) is much lower than other electrochemical PSA biosensors (0.25 ng/mL, Okuno J, Maehashi K, Kerman K et al: Label-free immunosensor for prostate-specific antigen based on single-walled carbon nanotube array-modified microelectrodes. Biosen. Bioelectron. 2007, 22, 2377-2381; 0.25 ng/ml, Sarkar P, Pal P S, Ghosh D et al: Amperometric biosensors for detection of the prostate cancer marker (PSA). International Journal Pharmaceutics. 2002, 238, 1-9; 3.0 ng/ml, Fernandez-Sanchez C, McNeil C J, Rawson K, Nilsson O: Disposable noncompetitive immunosensor for free and total prostate-specific antigen based on capacitance measurement. Anal. Chem. 76 (2004), 5649-5656). Compared to the currently available and generally used commercial methods for PSA testing using dedicated, centralized laboratories on large and automated high-throughput systems, the PSA biosensor present here has the great advantages including low cost, rapid and reliable quantitative results as well as small amounts of sample and reagents required for operation. Another advantage is the PSA biosensor described here is a POC device providing immediate results whereas currently used methods require dedicated laboratories. Thus the PSA biosensors described here is promising for clinical and medical diagnostic.

Example 2

The NADH peroxidase (Npx) of *S. faecalis* can be expressed and tested for enzyme activity (see, Poole and Claiborne, 1986, Parsonage, et al., 1995). The enzyme can be purified with a HiTrap Q column from GE Healthcare, eluted with 20 mM Tris/HCl pH 7.5 and 0-1 M NaCl in the presence of 1 mM TCEP. The enzyme can be concentrated to >10 mg/mL with an intensely yellow color from the flavin cofactor and stored at −80° C. In a standard assay condition, the solution mixture may consist of 0.3 mM EDTA, 0.16 mM NADH, and 1.3 mM $H_2O_2$ in 0.1 M potassium acetate buffer, pH 5.4. NADH can be added just prior to assay to avoid nonenzymatic loss. The assay can be started by adding 1 μg/ml Npx, and monitored by the decrease in 340 nm absorbance of NADH.

Reaction of the Npx enzyme with metal-containing PNA prepared as described above may be achieved by first slightly unfolding the Npx in guanidine hydrochloride followed by oxidation to form the linkage to Npx. As a non-limiting example, 50 μg (1 nmol) of Npx can be dissolved in 0.2 ml of Tris-HCl, pH 8.0 with 1.0 M guanidine. Hydrogen peroxide (1 nmol) can be added and incubated at 0° C. for 5 to 30 min. Then metal-containing PNA (for example, 5 nmol) can be added and incubated at 4° C. overnight. Hydrogen peroxide may be added to Npx stoichiometrically, converting the Npx Cys-thiol group to Cys-sulfenic acid which can easily react with peptide Cys-thiol group of MHP to form disulfide bond. The Npx-MHP complex may be purified with a HiTrap Q High Performance column, eluting with 20 mM sodium phosphate buffer pH 7.4 with 0.15-1.0 M NaCl. Complex of Npx-MHP with >95% purity may be eluted at around 0.3 M NaCl. The peptide can optionally be metalized, for example with $Co^{2+}$, after conjugation with the enzyme by mixing Npx-PNA with $CoCl_2$.

Example 3

Metalized Protein Linker in PSA Assay

Materials and Methods

N-hydroxysuccinimide (NHS), N-(3-Dimethylaminopropyl)-N'-ethylcarbodiimide (EDC), β-nicotinamide adenine dinucleotide reduced form (NADH) and tris (2-carboxyethyl) phosphine (TCEP) were purchased from Sigma. Hydrogen peroxide (30%) was from Mallinckrodt. Peptides were made by Bio-Synthesis, Inc. Monofunctionalized gold nanoparticle (AuNP), mono-sulfo-NHS-nanolgold, was from Nanoprobes. UV-visible absorption measurements were carried out on a SPECTRAmax® PLUS[384] Spectrophotometer from Molecular Devices. MALDI-TOF-MS spectra were obtained on a Voyager DE-PRO Biospectrometry Workstation. All scanning electron microscope images were taken with a JEOL-1200 SEM.

Enzyme Expression, Purification, Activity Assay

The NADH peroxidase (Npx) of *S. faecalis* was expressed, and tested for enzyme activity as described (Poole, L. B., Claiborne, A., 1986. J. Biol. Chem., 261, 14525-145233; Parsonage, D., Miller, H., Ross, P. R., Claiborne, A., 1995. J. Biol. Chem. 268, 3161-3167). The enzyme was purified with a HiTrap Q column from GE Healthcare, eluted with 20 mM Tris/HCl pH 7.5 and 0-1 M NaCl in the presence of 1 mM TCEP. The enzyme was concentrated to >10 mg/mL with an intensely yellow color from the flavin cofactor and stored at −80° C. In a standard assay condition, the solution mixture consisted of 0.3 mM EDTA, 0.16 mM NADH, and 1.3 mM $H_2O_2$ in 0.1 M potassium acetate buffer, pH 5.4. NADH was added just prior to assay to avoid nonenzymatic loss. The assay was started by adding 1 μg/ml Npx, and monitored by the decrease in 340 nm absorbance of NADH.

Peptides

Sequences and electrochemical measurements on a number of peptides, their binding characteristics to divalent metals and electron-transfer properties were characterized and reported earlier (Yeh, J. I., Zimmt, M. B., Zimmerman, A. L., 2005. Biosensors and Bioelectronics 21, 973-978). Briefly, the leucine-zipper region of a transcriptional factor, GCN4, was synthesized and this comprised of 33 amino acids in length. Mutations of residues to histidines were made at i, i+4 positions to bind metals at the outer faces of peptides and a previously reported multiple histidine peptide (MHP) (Yeh, J. I., et al. Biosensors and Bioelectronics 21, 973-978) was used for the majority of the studies reported here. A thioester moiety at the carboxyl-termini of the peptide or a sulfhydryl group from a cysteine was designed to react with the active site thiolate of Npx to form a covalent linkage.

Metallization of Peptide and Mass Spectrometry

The binding of metal ions to the MHP was studied using isothermal titration calorimetry (ITC), as reported earlier (Yeh, J. I., et al. Biosensors and Bioelectronics 21, 973-978) and mass spectrometry (MS) methods, in this study. The MS samples were made by mixing MHP peptide with $CoCl_2$ in a ratio of 2 mole of $Co^{2+}$ per mole of histidine, accounting for the multiple histidines in each chain. Reaction conditions were 10 mM Tris.HCl at pH 7.0, 8.0, 8.5 and 9.0 respectively. Excess $Co^{2+}$ were removed by exchanging the buffer to 10 mM Tris.HCl at the respective pH with YM-3 concentrators (Millipore). The products were subsequently mixed with a matrix of saturated α-cyano-4-hydroxycinnamic acid (CHCA) in 0.3% trifluoroacetic acid and 50% acetonitrile in water in preparation of MALDI-TOF-MS spectroscopy.

Conjugation of Peptide to Enzyme and Metallization

Enhanced reaction of the enzyme with peptide was achieved by first slightly unfolding the enzyme in guanidine hydrochloride followed by oxidation to form the linkage to Npx. To do this, 50 μg (1 nmol) of Npx was dissolved in 0.2 ml of Tris-HCl, pH 8.0 with 1.0 M guanidine. Hydrogen peroxide (1 nmol) was added and incubated at 0° C. for 5 to 30 min. Peptide MHP (5 nmol) was then added and incubated at 4° C. overnight. Hydrogen peroxide was added to Npx stoichiometrically, converting the Npx Cys-thiol group to Cys-sulfenic acid which can easily react with peptide Cys-thiol group to form disulfide bond. The Npx-MHP complex was purified with a HiTrap Q High Performance column, eluting with 20 mM sodium phosphate buffer pH 7.4 with 0.15-1.0 M NaCl. Complex of Npx-MHP with >95% purity was eluted at around 0.3 M NaCl. The peptide was then metallized with $Co^{2+}$ by mixing Npx-MHP with $CoCl_2$.

Labeling of Bioassembly

Npx bioassembly was labeled with 1.4 nm AuNP, monofunctionalized with a sulfo-1,4-succimido group (Nanoprobes) for reaction to primary amines. In a representative procedure, 6 mol of AuNP was dissolved in 200 μl $dH_2O$ immediately before use, then added to the Npx bioassembly, containing 60 μg of Npx-peptide in 100 μl PBS buffer (20 mM sodium phosphate and 0.15 M sodium chloride, pH 7.4). The mixture was incubated at 4° C. overnight. Excess AuNP was removed by concentrating with YM-30 concentrator, washed with PBS buffer, and then concentrated again. This efficiently removed unbound AuNP through size partition, since the bioassembly is ~64 kD (Npx enzyme 49 kD, AuNP 15 kD), readily retained from passing through the membrane while free nanoparticles easily permeate through. The AuNP labeled Npx bioassembly was further purified by gel-filtration to isolate the fully-labeled bioassembly.

Reaction of Bioassembly to CNT

The CNT electrodes were subjected to reactive ion etching. This procedure simultaneously opens the tips while producing a high density of carboxylic acid groups at the tips for subsequent peptide linkage reactions. Npx linking to the CNT tips was accomplished with well known amine coupling procedures (Withey, G. D., Lazareck, A. D., Tzolov, M. B., Yin, A., Aich, P., Yeh, J. I., Xu, J., 2006. Biosensors and Bioelectronics 21 (8), 1560-1565) to the CNTs free carboxyl groups. The carboxylate groups on the CNT electrode tips were activated by pre-treating with a freshly made EDC-NHS mixture at room temperature for 1 h, which contains 0.4 M EDC/HCl and 0.1 M NHS in water (pH 6 to 7). The pre-treated electrode was rinsed thoroughly with PBS buffer and de-ionized water and then treated with Npx assembly in PBS buffer, pH 7.4 at 4° C. overnight.

Imaging of CNT-Bioassembly

Scanning Electron Microscopy (SEM) was used to image gold nanoparticle labeled Npx-bioassembly conjugated at the tips of highly ordered carbon nanotubes (CNT) arrays. The highly ordered CNT arrays were beneficial to forming evenly distributed bioassembly, which was confirmed through the SEM imaging. They are fabricated through growth of multi-walled nanotubes (MWNTs) within an aluminum oxide nanopore template (Li, J., Papadopoulos, C., Xu, J., Moskovits, M., 1999. Appl. Phys. Lett. 75, 367-369; Papadopoulos, C., Chang, B., Yin, A., Xu, J., 2002. International Journal of Nanoscience 1, 205-212). The template defines the geometric features of the CNT array, with the three dimensional structure of the sensor elucidated in FIG. 6. For the applications described here, the CNTs are 50 nm in diameter, have walls of 3 nm thickness, and exhibit an exposed length of 60 nm, a total length of 10 um, and a center-to-center spacing of 100 nm between adjacent tubes as verified FIG. 6 (All scanning electron microscope (SEM) images were taken with a LEO 1530 SEM).

Electrochemical Measurements

Electrochemical experiments were performed on an Epsilon Electrochemical Workstation from BASi. The modified CNT electrodes (i.e. working electrodes) and controls, were cycled in 0.1 M potassium acetate buffer, pH 5.4. The reference electrode was a Ag/AgCl electrode and a platinum wire electrode was used as the auxiliary electrode.

Results and Discussion

CNTs are of great utility, particularly when they are highly ordered and vertically aligned as in the arrays used in the work described here. These geometrical parameters are advantageous for bio-functionalization and bio-sensing applications (Shim, M., Kam, N., Chen, R., Li, Y., Dai, H., 2002. Nano Lett. 2, 285-288; Sotiropoulou, S., Chainiotakis, N., 2003. Anal. Bioanal. Chem. 375, 103-105 Tsang, S., Chen, Y., Harris, P., Green, M., 1994. Nature 372, 159-162; Wang, S., Zhang, Q., Wang, R., Yoon, S., 2003. Biochem. Biophys. Res. Commun. 311, 572-576; Wang, S., Zhang, Q., Wang, R., Yoon, S., Ahn, J., Yang, D., Tain, J., Li, J., Zhour, Q., 2003. Electrochem. Commun. 5, 800-803; Yang Y., Wang Z., Yang M., Li J., Zheng F., Shen G., Yu R., 2007. Analytica Chimica Acta 584, 268-274) as they exhibit high conductivity and can be modified with site specificity (Withey, G. D., et al., 2006. Biosensors and Bioelectronics 21 (8), 1560-1565; Taft, B., Lazareck, A., Withey, G., Yin, A., Xu, J. M., Kelley, S. O., 2004. J. Am. Chem. Soc. 126(40), 12750-12751) as their closed sidewalls and open ends exhibit inherently different physical and chemical properties (Saito, R., Dresselhaus, G., Dresselhaus, M. (Eds.), 1998. Physical Properties of Carbon Nanotubes. Imperial College Press, London, UK; Dresselhaus, M., Dresselhaus, G.; Avouris, P. (Eds.), 2001. Carbon Nanotubes: Synthesis, Structure, Properties, and Applications. Springer, Berlin). Linkage between CNTs and enzymes via metallized peptides provides a mean of coordinating formation between the various components, particularly accessing and aligning to the enzyme's active site. The Npx enzyme exists in the thiolate state under reducing conditions of the reaction to form the bioassembly. The activity (Poole, L. B., Claiborne, A., 1986. J. Biol. Chem., 261, 14525-145233; Parsonage, D., et al., 1995. J. Biol. Chem. 268, 3161-3167) of the enzyme was determined prior to assembly formation to ascertain the reduced state of the cysteine and competency for disulfide bond formation under all conditions, including in the presence of GnHCl and peptide (Table 6).

TABLE 6

Relative Npx activity (normalized against Npx activity in the absence of Guanidine; all measurements have standard deviations of +/−18%) during Npx and peptide reaction. The reaction buffer contains 50 mM Tris-HCl pH 8.0 and 1.0 M Guanidine.

| Time (minutes) | Npx only, in reaction buffer | Npx and $H_2O_2$ (1:1) in reaction buffer | Peptide MHP added into the mixture of Npx and $H_2O_2$ at 30 min |
|---|---|---|---|
| 2 | 67% | 72% | — |
| 15 | | 70% | — |
| 30 | 81% | 67% | 57%, peptide was added at this point. |
| 50 | 79% | 87% | |
| 65 | | | 43% |
| 110 | 70% | 72% | 32% |
| 210 | 63% | 63% | 30% |

To form the linkage between enzyme and peptide, oxidation to form a disulfide (or a thioester bond, depending on the functional group synthesized) is catalyzed by hydrogen peroxide under mild conditions. If the concentration of hydrogen peroxide is in excess, the peroxide could potentially oxidize the Npx Cys-sulfenic acid (Cys-SOH, secondary redox center) further to Cys-sulfinic (Cys-$SO_2H$) and/or -sulfonic acid (Cys-$SO_3H$), oxidation states that are unable to react with peptide's Cys-thiol group (Yeh, J. I., Claiborne, A., 2002. In: Sen, C. and Packer. L. (Eds.), Methods in Enzymology. Academic Press, New York, N.Y., 353, 44-45; Claiborne, A., Mallett, C., Yeh, J. I., Luba, J., Parsonage, D., 2001. Advances in Protein Chemistry 58, 215-276; Claiborne, A., Yeh, J. I., Mallett, T. C., Luba, J., Crane, E. J., Charrier, V., Parsonage, D., 1999. Biochemistry 38, 15407-15416). Thus, the amount of hydrogen peroxide was controlled and limited to a quantitative ratio of Npx in order to maximize Npx-peptide formation.

For labeling, colloidal conjugation of metals and semiconductors to biological molecules packed into specific geometrical arrangements is the subject of intense scientific investigation (Xiao, S., Liu, F., Rosen, A., Hainfeld, J., Seeman, N., Musier-Forsyth, K., Kiehl, R., 2002. Journal of Nanoparticle Research 4, 313-317; Xu, W., Xu, S., Ji, X., Song, B., Yuan, H., Ma, L., Baib, Y., 2005. Colloids and Surfaces B: Biointerfaces 40, 169-172; Xu Y. Y., Bian C., Chen S., Xia S., 2006. Analytica Chimica Acta 561 (1-2), 48-54). Bio-conjugated colloidal structures have been used for a wide variety of higher order structures including multi-particle complexes (Alivisatos, A. P., Johnsson, K. P., Peng, X., Wilson, T. E., Loweth, C. J., Bruchez, M. P., Schultz, P. G., 1996. Nature 382, 609-611; Hazarika, P., Irrgang, J., Spengler, M., Niemeyer, C. M., 2007. Advanced Functional Materials 17(3), 437-442; Yao, H., Yi, C. Q., Tzang, C. H., Zhu, J. J., Yang, M. S., 2007. Nanotechnology 18 (1), Art. No. 015102), DNA scaffolds (Xiao, S., et al., 2002. Journal of Nanoparticle Research 4, 313-317; Helfrich M. R., El-Kouedi M., Etherton M. R., Keating C. D., 2005. Langmuir 21(18), 8478-8486; Yao, H., et al., 2007. Nanotechnology 18 (1), Art. No. 015102), nanotube hybrids (Taft, B., Lazareck, A., Withey, G., Yin, A., Xu, J. M., Kelley, S. O., 2004. J. Am. Chem. Soc. 126(40), 12750-12751) and immunological identification platforms (Xu, W., et al., 2005. Colloids and Surfaces B: Biointerfaces 40, 169-172; Luo L., Zhang Z., Hou L., 2007. Analytica Chimica Acta 584 (1) 106-111). Prior to visualizing molecules with nanoparticles, fluorescence based labeling was the dominant technique for characterizing immobilized bio-molecules, and is still a useful technique for studies not requiring resolution at the nanoscale (Csaki, A., Moller, R., Straube, W., Kohler, J., Fritzche, W., 2001. Nucleic Acids Research 29(16), E81; Csaki A., Garwe F., Steinbruck A., Maubach G., Festag G., Weise A., Riemann I., Konig K., Fritzsche W., 2007. Nano Lett. 7 (2), 247-253). Additionally, while optical imaging limitations can be addressed by fluorescing semiconductor nanodots, their potential toxicity to biological molecules requires them to be encapsulated, complicating the bio-conjugation process and lowering the optical fluorescence yield (Wang, L., Reipa, V., Blasic, J., 2004. Bioconjugate Chem. 15, 409-412). In contrast, gold colloids have been highly utilized in biomolecule labeling/visualization assays as they are stable over long periods of time, have readily controlled sizes and are compatible with antibodies, antigen proteins, DNA and RNA (Alivisatos, A. P., et al., 1996. Nature 382, 609-611; Mirkin, C. A., Letsinger, R. L., Mucic, R. C., Storhoff, J. J., 1996. Nature 382, 607-609; Hazarika, P., et al., 2007. Advanced Functional Materials 17(3), 437-442; Yao, H., et al., 2007. Nanotechnology 18 (1), Art. No. 015102). Perhaps the most robust form of gold colloid bioconjugation relies on a gold-thiol interaction for the adsorption of thiol-labeled molecules on gold (Csaki, A., et al., 2001. Nucleic Acids Research 29(16), E81; Georgiadis, R., Peterlinz, K., Peterson, A., 2000. J. Am. Chem. Soc. 122, 3166-3173; Petrovykh, D., Kimura-Suda, H., Whitman, L., Tarlov, M., 2003. J. Am. Chem. Soc. 125, 5219-5226; Karpovich, D. S., Blanchard, G. J., 1994. Langmuir 10, 3315-3322; Song Y. H., Liu Y. Q., Yang M. L., Zhang B. L., Li Z., 2006. Applied Surface Science 252 (16), 5693-5699; Yao, H., et al., 2007. Nanotechnology 18 (1), Art. No. 015102). Its well known fast kinetics and single step incubation process reduce contamination risk by avoiding multiple washes (Mo, Z., Wang, H., Liang, Y., Liu, F., Xue, Y., 2005. The Analyst 130, 1589-1594). Chemiabsorption of gold nanoparticles to bio-molecules is typically through free thiol groups available on the analyte which, given the correct stoichiometry, facilitates bio-functionalization of the gold (Taft, B., et al., 2004. J. Am. Chem. Soc. 126(40), 12750-12751; Mo, Z., et al., 2005. The Analyst 130, 1589-1594; Sato, K., Hosokawa, K., Maeda, M., 2003. J. Am. Chem. Soc. 125, 8102-8103; Csaki, A., et al, 2001. Nucleic Acids Research 29(16), E81). Alternatively, gold nanoparticle modification through terminal amine or carboxyl groups is also common, but additional coupling steps are required (Withey, G. D., et al., 2006. Biosensors and Bioelectronics 21 (8), 1560-1565; Niemeyer, C. M. (Ed.), 2004. Bioconjugation Protocols: Strategies and Methods. Humana Press, Totowa, N.J.).

Using monofunctionalized gold nanoparticles permitted stochimetric labeling of biomolecules through reaction of an activated succinimide group to amino terminus of proteins and peptides (Ribrioux, S., Kleymann, G., Haase, W., Heitmann, K., Ostermeier, C., Michel, H., 1996. J. Histochem. Cytochem. 44, 207-213; Segond von Banchet, G., and Heppelman, B., 1995. J. Histochem. Cytochem. 43, 821-827). For the AuNP labeling, the main benefit is that the standard of specificity of a chemical bond (gold-thiolate) is enhanced by the steric requirement of gold having to access a geometrically confined thiol functional group. As the gold nanoparticle size is at 1.4 nm, small as a phase contrast reagent in SEM, it would be difficult to image without size enhancement. We used a solution approach to deposit gold ions onto the nanoparticle to reproducibly enlarge the nanogold particles to about 7-8 nm in diameter, resulting in improved backscatter detection of the labeled bioassembly on CNT electrode tips. Gold ions catalytically deposited permits reproducible growth of bioassembly-linked nanoparticle. This linking scenario's specificity is demonstrated by the negligible amount of non-specific CNT sidewall absorption of Npx-AuNP conjugate and the subsequent high affinity of Npx-AuNP present virtually exclusively and stoichiometrically (relative to the bioassembly) on the carboxyl-etched tips of CNTs tips (FIG. 7).

Figure 8:
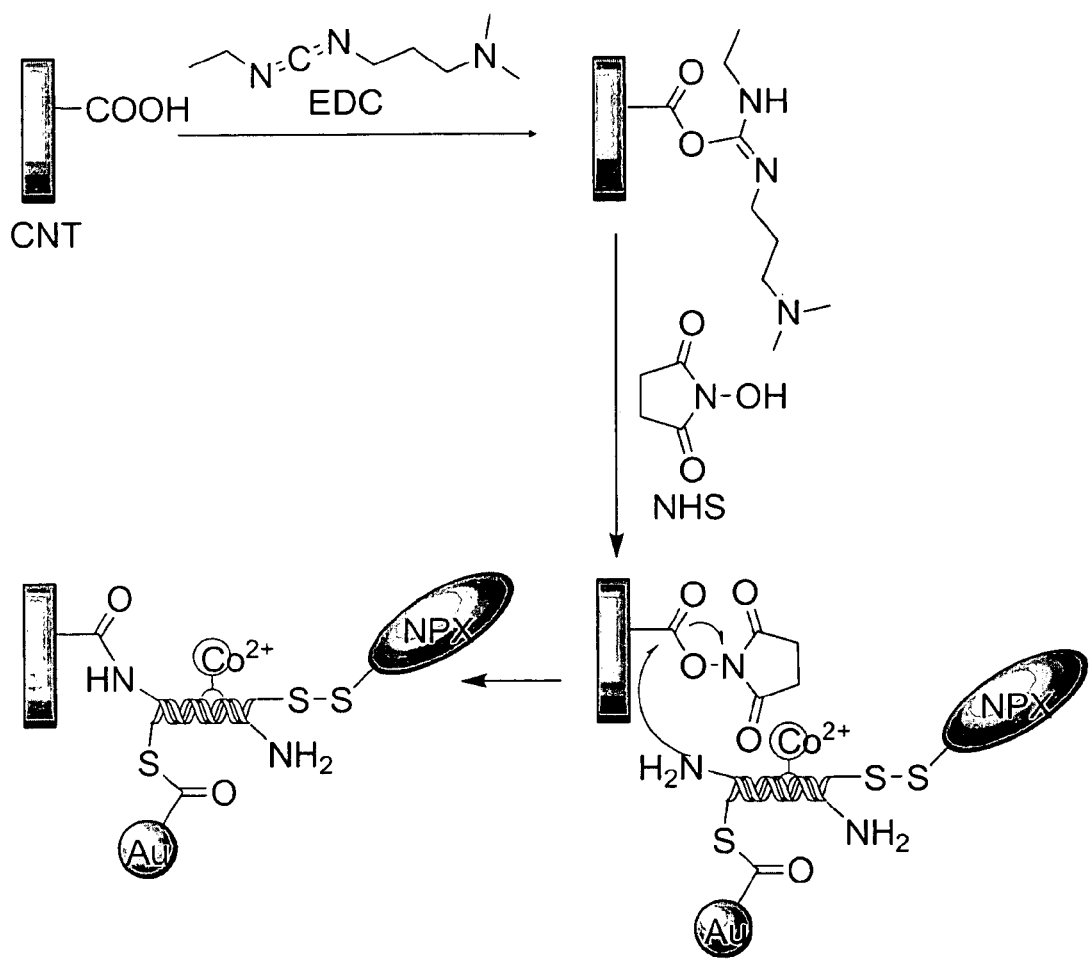
FIG. 8 shows schematically the formation of a CNT-Npx electrode through subsequent EDC and NHS conjugation. The helices represent the peptide nanowire.

This strategy distinguishes itself in that the visualization of successful bioassembly-CNT conjugation is based on imaging chemioabsorbed gold nanoparticle Npx conjugates linked together via labeled peptide, specifically reacted with the sulfenic acid center of the enzyme, as indicated in FIG. 8.

An additional advantage of this approach is that this offers a non-denaturing means of accessing the buried active sites of enzymes. Globular proteins fold such that their reactive centers are protected from nonproductive side-reactions. Consequently, a difficulty in linking modular enzymes to electrodes is penetrating their active centers, where signals are generated, to the electrodes, where these signals are detected. We have circumvented this problem by utilizing peptides that are highly elongated, with a stable and well-defined helical topology that can penetrate into active sites with apparently minimal disruption of conformation, as confirmed by maintenance of enzymatic activity. The activity of Npx was maintained, falling to about 50% of control values when monitored along the Npx-peptide reaction profile, extending the reaction to over three hours (Table 6). It should be noted that this value is skewed negatively due to the nature of the assay and the average functional state of the enzyme is likely higher. The structural integrity of these peptides, confirmed through high resolution structure elucidation recently completed by our group (manuscript in preparation) and by others on leucine zippers (O'Shea, E. K., Klemm, J., Kim, P. S., Alber, T., 1991. Science 254, 538-544) indicates that these can coordinate metals and maintain distance and geometrical relationships that are conducive to electron transfer. The ease at which peptides can be functionalized highlights the general applicability of this approach to other systems.

Figure 9:
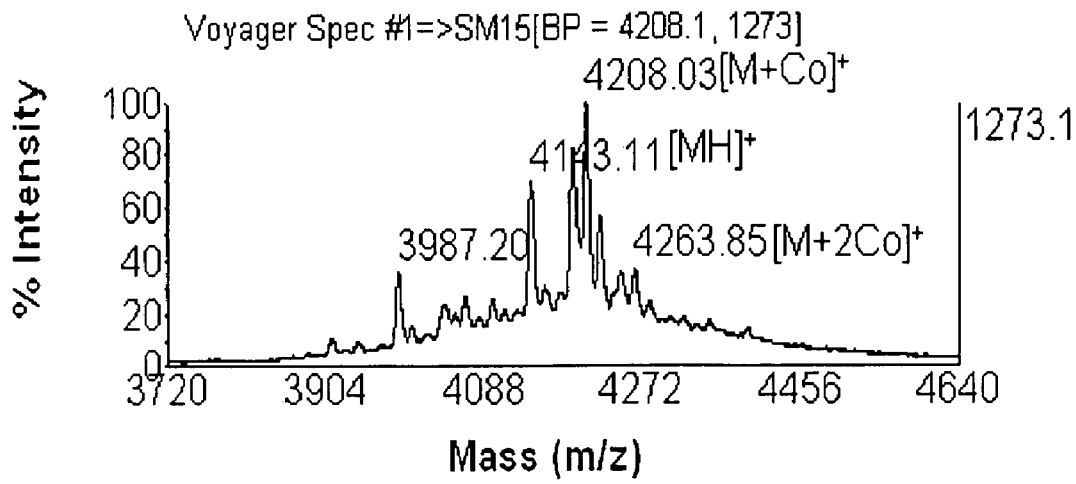
FIG. 9 shows MALDI-TOF-MS spectra of peptide MHP binding complex with $Co^{2+}$ in 10 mM Tris/HCl, pH 9.0. $MH^+$=4143.11.

Although metallization of peptides is well documented, multiple metallization is less common. This was achieved in the case of the MHP peptide by designing metal-binding sites at outward faces of the strands. These binding sites did not disrupt the critical leucine zipper interaction required for conformational stability (Krantz, B. A., Sosnick T. R., 2001. Nat. Struct. Biol. 8(12), 1042-1047). Several peptides were synthesized which had variable metal-binding stochiometries (Yeh, J. I., et al., 2005. Biosensors and Bioelectronics 21, 973-978). The most efficient transducer of electrons were peptides with multiple binding sites, whereas peptides that bound two metals, one on each end of the peptide, did not transduce any signals, highlighting the importance of maintaining a critical distance between metal centers for electron conduction. Evidence of metal binding to the peptide has been obtained by isothermal titration calorimetry, X-ray absorption fluorescence spectroscopy (EXAF) measurements (Yeh, J. I., et al., 2005. Biosensors and Bioelectronics 21, 973-978) and most recently by mass spectrometry analysis of the peptide-$Co^{2+}$ complex (FIG. 9). For the peptide-$Co^{2+}$ complex formed at pH 9.0, both $[M+Co]^+$ and $[M+2Co]^+$ were clearly observed, indicating that at least two cobalt atoms were bound to one peptide strand under basic conditions. It is very likely additional cobalt atoms were bound to the MHP backbone, as indicated by the earlier ITC analysis, but these higher metallization states could not be easily detected by the MALDI-TOF-MS, since the matrix used for MS sample preparation contains trifluoroacetic acid, potentially disruptive to stability of cobalt binding to the histidines of MHP. Nonetheless, these results, in conjunction with the earlier reported solution characterization, strongly indicates metal binding stoichimetries of two to four metals per strand and these are sufficient for electron transduction.

Figure 10:
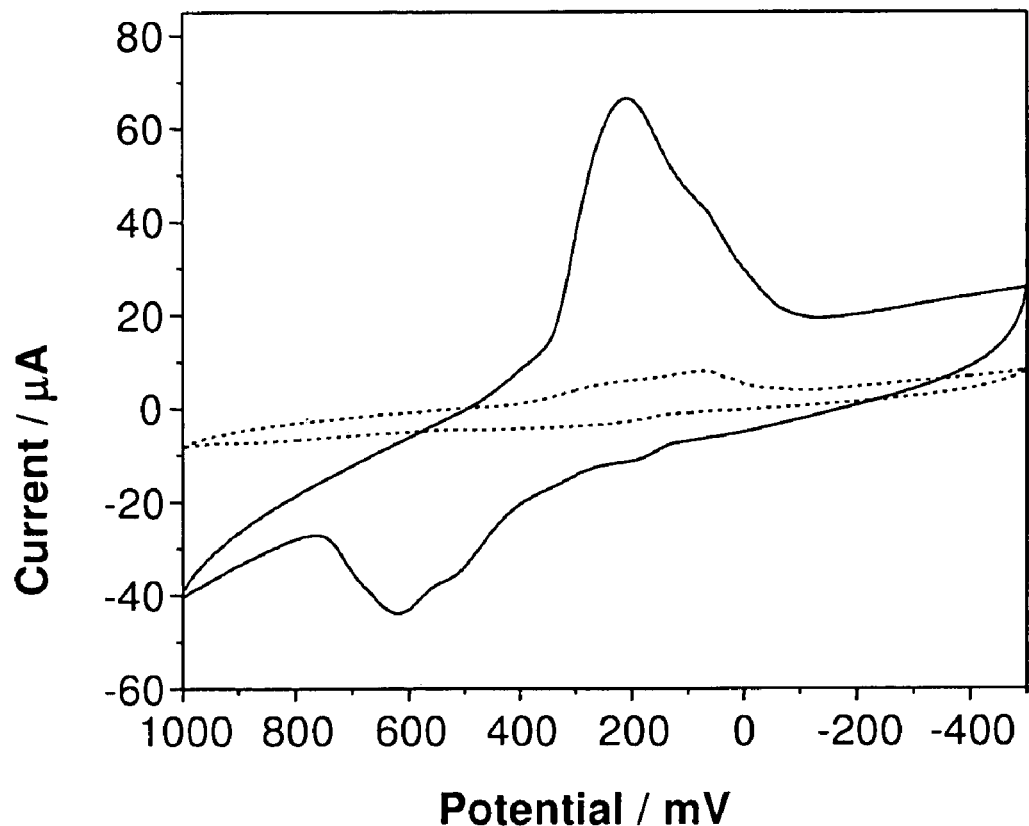
FIG. 10 graphically illustrates a CNT electrode immobilized with Npx-MHP-$Co^{2+}$-AuNP (solid line) and with Npx-AuNP (dash line) bioassemblies in 0.1 M potassium acetate buffer, pH 5.4 at a scan rate of 100 mVs$^{-1}$.
Figure 11:
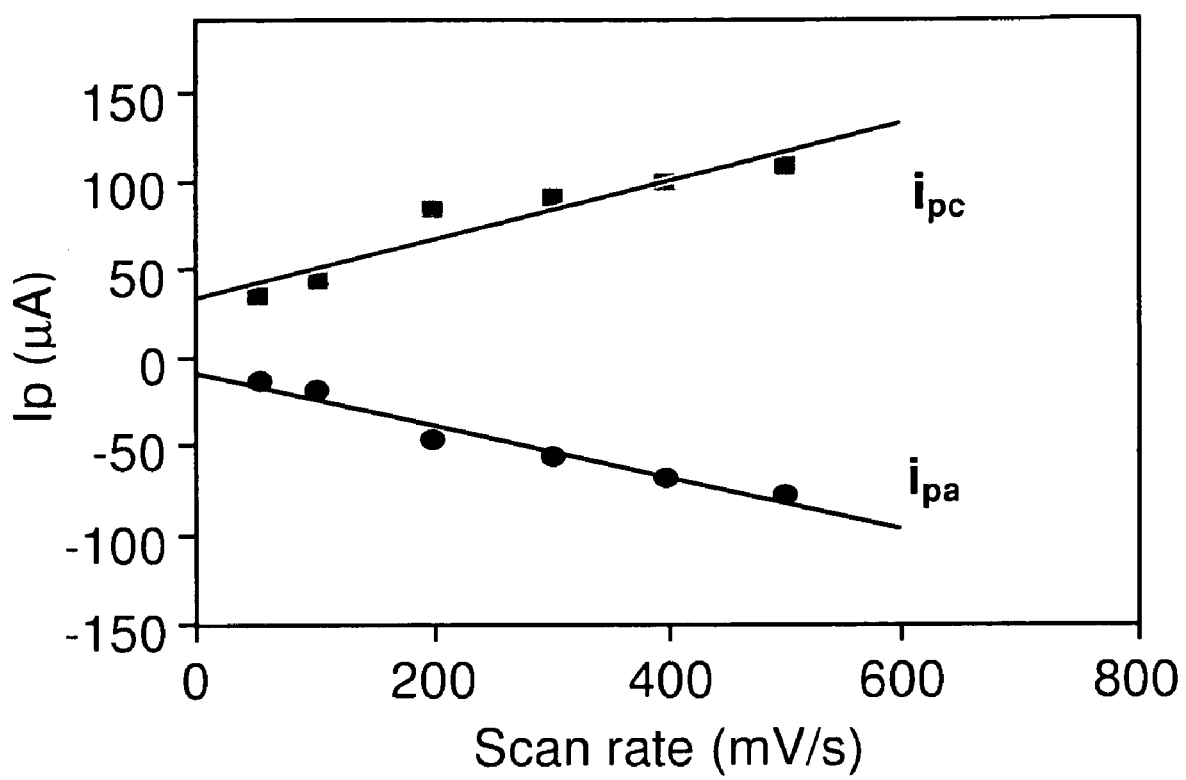
FIG. 11 is a plot of peak currents of cyclic voltammetrys (CVs) of a CNT electrode immobilized with Npx-MHP-$Co^{2+}$-AuNP. The CVs were measured at scan rates of 50, 100, 200, 300, 400, 500 mV/s respectively in 0.1 M potassium acetate buffer, pH 5.4.

Electrochemical measurements of the Npx-bioassembly linked CNT electrode array showed strong cyclic voltammetry (CV) signals when the metallized peptide nanowire was incorporated (FIG. 10, solid line). At a scan rate of 100 mV/s, the anodic peak current is −22.51±3.71 µA and cathodic peak current is 45.62±3.76 µA for this electrode. A control electrode comprised of CNT electrode linked with Npx-AuNP without peptide as a spacer only gave weak signals (FIG. 10, dashed line). The effect of scan rate for cyclic voltammetry measurements on the response of the immobilized CNT electrode is shown in FIG. 11. The anodic and cathodic peak currents ($i_{pa}$ and $i_{pc}$) increased in a linearly proportional manner as the scan rate increased from 50 mV to 500 mV (FIG. 11). The linearity of response confirms that the signal is generated via immobilized bioassembly on the CNT electrodes and not through solution electroactive species.

Conclusion

We have successfully fabricated nanobioassembly arrays comprised of the redox enzyme, Npx, covalently linked to a CNT electrode array through metallized multi-histidine peptides based on the sequence of GCN4 leucine zipper. Our results demonstrate that this modularly assembled electrode is a highly sensitive electrochemical biosensor. This biosensor array is capable of detecting changes in redox status in-situ (Xia, T., Kovochich, M., Brant, J., Hotze, M., Sempf, J., Oberley, T., Sioutas, C., Yeh, J. I., Wiesner, M. R., Nel, A. E., 2006. Nano Lett. 6 (8), 1794-1807). Evidence from isothermal titration calorimetry, EXAF (Yeh, J. I., et al., 2005. Biosensors and Bioelectronics 21, 973-978), and MALDI-TOF-MS (this report), shows that the peptide MHP binds to metal ions with micromolar binding affinities. Chemical linkage strategies allow specific covalent linkage of Npx through the disulfide or thioester bond formation between the Cys-thiol or thioester of the peptide and Cys-42 of Npx. Through stepwise formation, the bioassembly of Npx-MHP can also be subsequently covalently linked to CNT electrodes through NHS-assisted amide bond formation. The CNT-bioassembly labeled with gold nanoparticles, whose phase contrast properties were enhanced through a controlled solution deposition approach, can be viewed via SEM. The SEM results confirmed precise Npx-bioassembly linkage onto the carboxyl-terminated tips of CNT electrode array and not to the sidewalls.

In coordinating the various electron-transducing units of the bioassembly, the metallized peptide served both as a conductor and spacer and was essential in maintaining conformational stability of the enzyme. Our modular assembly method and concept for bioelectrode formation using a peptide as a specific linker and functioning as a nanowire conduit of signals are generalizable and applicable to other bionanoelectrode systems.

Example 4

Figure 12:
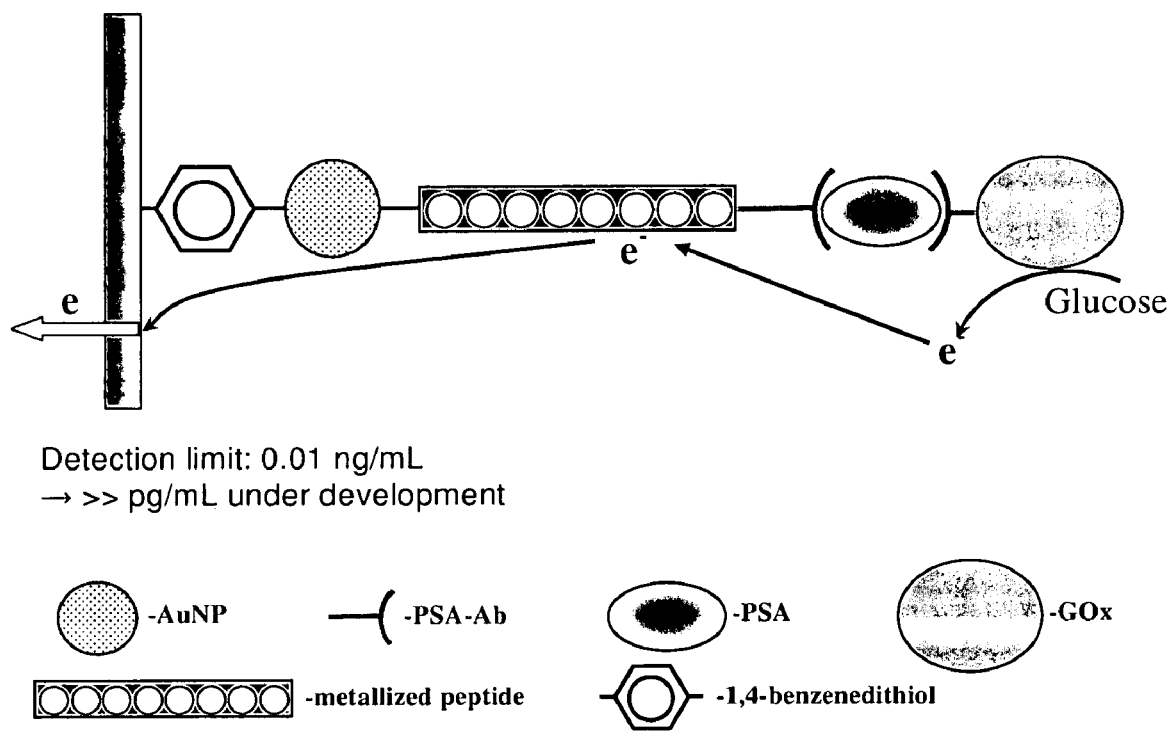
FIG. 12 shows schematically a biosensor for detecting PSA, where the PSA-antibody is covalently anchored onto the AuNP-metallized peptide using EDC/NHS. For detection of PSA, the PSA-antibody modified electrode is recognized by PSA and further recognized with PSA-antibody-GOx complex as detectable signal upon forming a sandwich structure.

A biosensor for detecting PSA levels in a sample may be constructed as shown in one non-limiting embodiment in FIG. 12. Briefly, a binding reagent specific to PSA (Anti-PSA binding reagent) is attached to a metalized polypeptide spacer, which, in turn, is linked to an electrode. The peptide spacer may be prepared in any manner and have any useful sequence, for example as described in Example 3 or elsewhere in this document. A redox tag comprises PSA linked to a redox enzyme, such as GOx is bound to the anti-PSA binding reagent. PSA in a sample will displace the redox tag, resulting in loss of electron flow when an enzyme substrate of the redox enzyme is present, substantially as shown above. In another embodiment shown in FIG. 12, the redox tag is a redox enzyme bound to an anti-PSA antibody that can bind PSA at a different epitope that the anti-PSA antibody linked to the metalized peptide. In the presence of a substrate for the redox enzyme, such as glucose/GOx, and PSA, a connection is formed between the redox enzyme and the nanoelectrode, thereby increasing electron flow through the nanoelectrode and permitting quantification of PSA levels in a sample.

Example 5

Figure 13A:
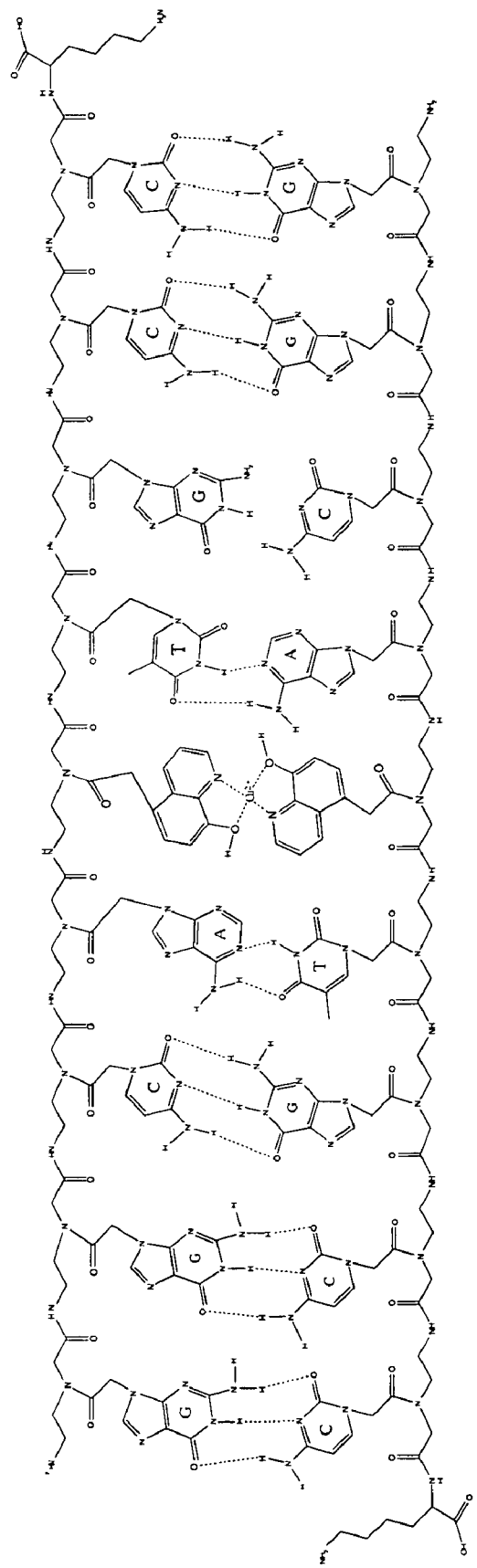
FIG. 13A shows a structure and sequence of PNA (8hqR) bound with $Cu^{2+}$, as described in Example 5.
Figure 13B:
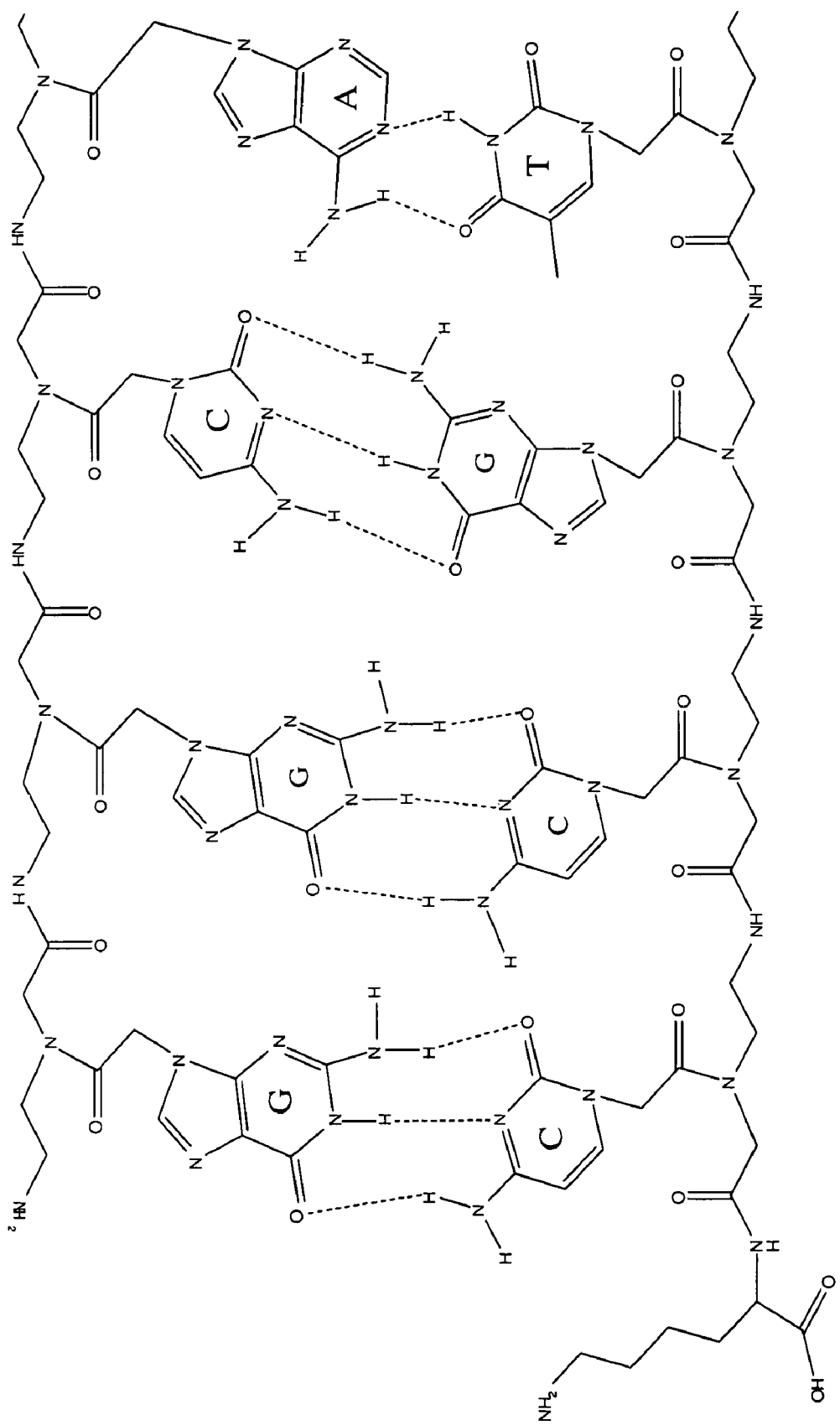
FIGS. 13B and 13C are expanded views of the left (13B) and right (13C) sides of the structure of FIG. 13A.
Figure 13C:
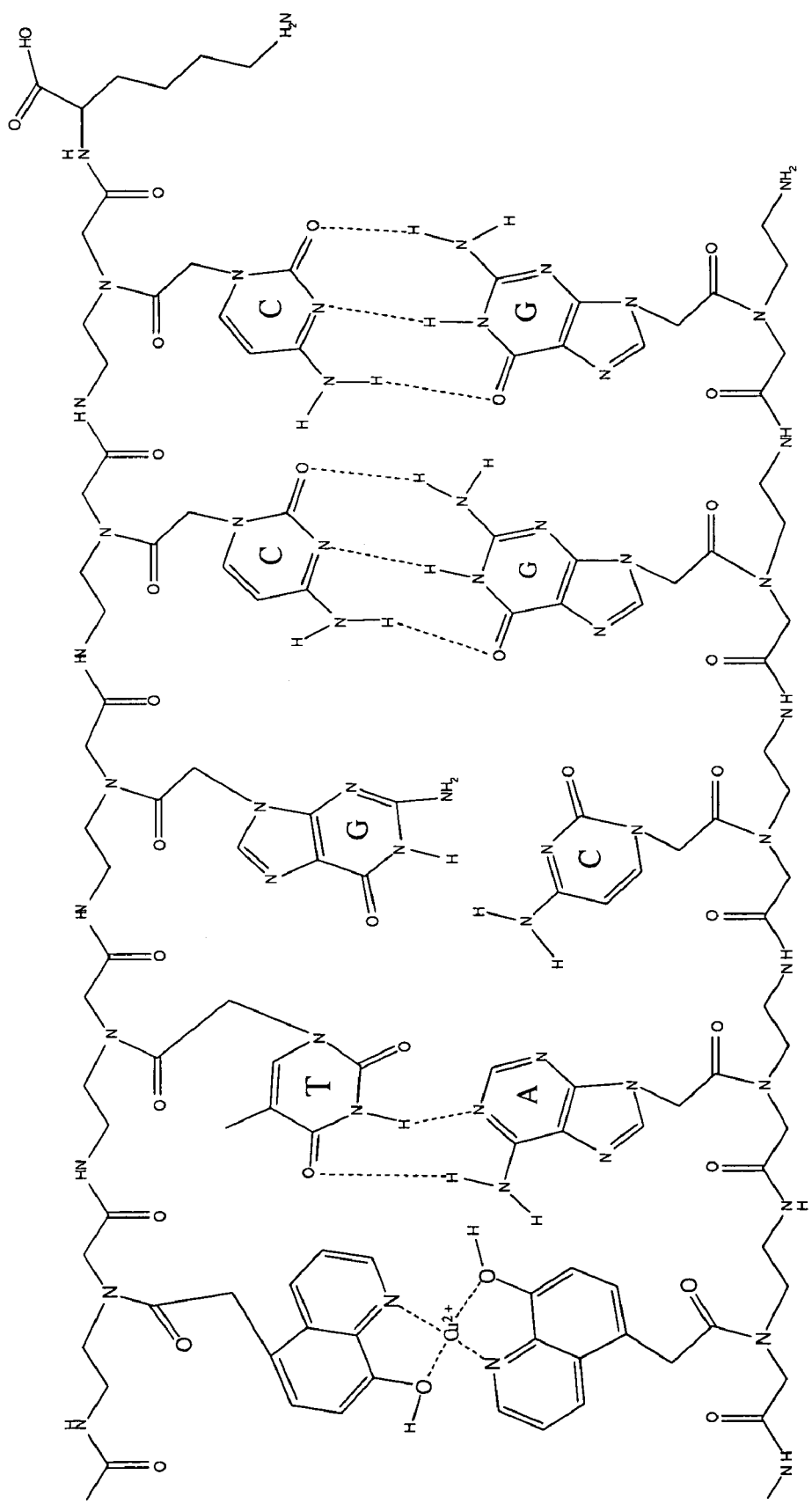

Materials—Prostate specific antigen (PSA), mouse monoclonal PSA antibody and human PSA immunoassay (ELISA, Cat: DKK300) were purchased from RD&D Co. Peptide nucleic acid (PNA: $NH_2LysCCGTQ_1ACGG$-H, 8hqR) was synthesized and bound with $Cu^{2+}$. FIG. 13 shows the structure of the PNA. The 3D gold nanoelectrode ensembles (NEE) were fabricated by Dr. Kelley's laboratory at Toronto University. Glucose oxidase (GOx) from *Apergillus niger,* 3-mercapto-propionic acid (MPA), N-ethyl-N-(dimethylaminopropyl) carbodiimide (EDC), N-hydroxy-succinimide (NHS) and ethanolamine-HCl were purchased from Sigma. All other chemicals and materials were purchased from Sigma unless otherwise noted.

Figure 14:
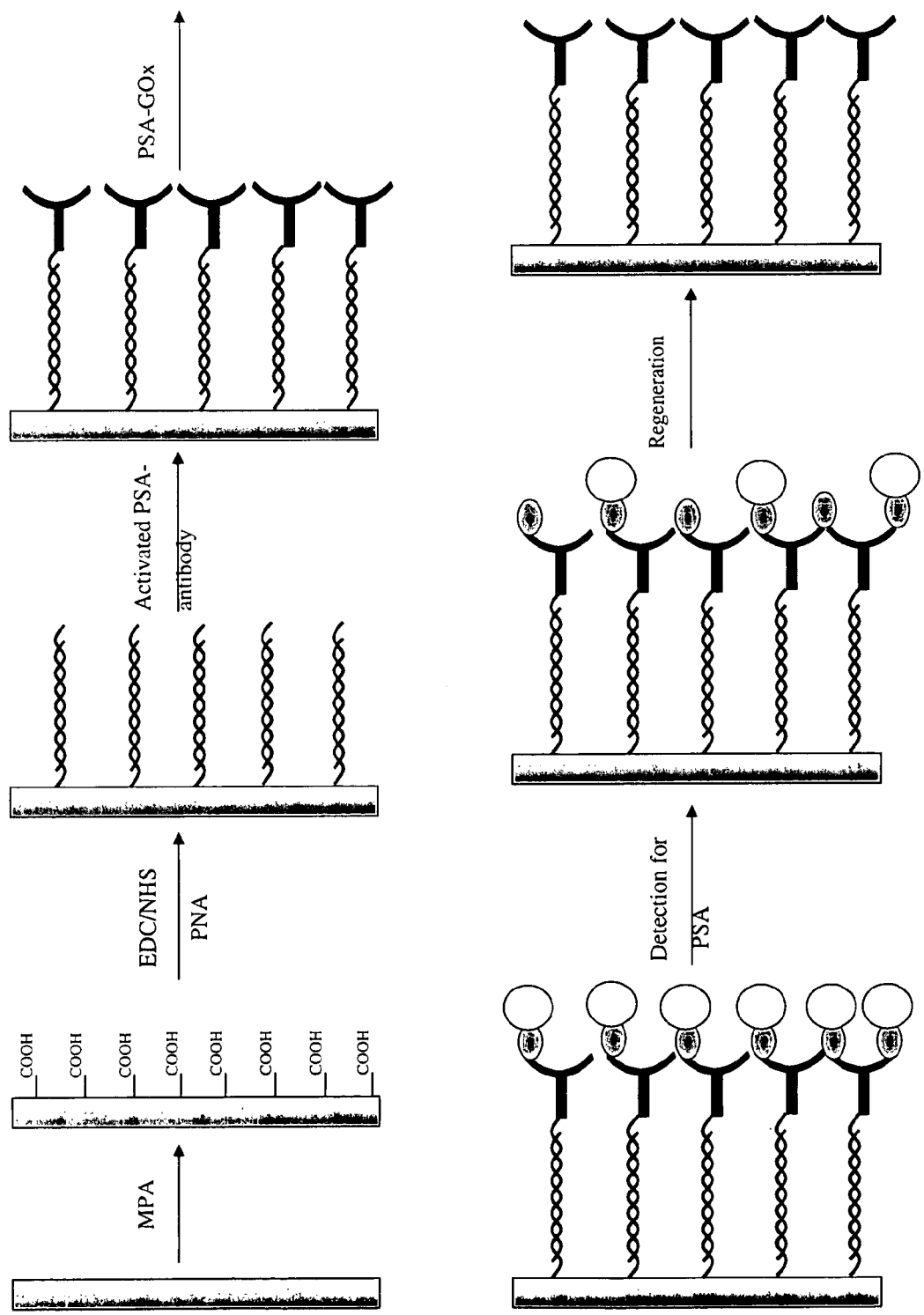
FIG. 14 provides a schematic illustration of the fabrication process and the detection process of a PSA biosensor, as described in Example 5.

Fabrication of PSA biosensor with the PNA—The gold disc electrode (1.6 mm in diameter, purchased from BASi) was polished using 0.05 μm alumina and sonicated in $ddH_2O$ for 10 min. The electrode was then pretreated electrochemically in 0.1 M $H_2SO_4$ by cyclic voltammetry in the potential range of 0 to 1.5 V at a scan rate of 0.1 V $s^{-1}$ for 15 min until a steady-state cyclic voltammogram of a clear and reproducible gold surface was obtained. Then the electrode was washed with $ddH_2O$ thoroughly followed by immersion in 10 mM MPA (in ethanol) overnight to form a MPA monolayer. The MPA monolayer modified gold electrode was then washed with ethanol and $ddH_2O$. It was further treated with a solution of 0.2 M EDC and 0.05 M NHS for 1 h at room temperature. The electrode was then washed with water and reacted with the PNA for 12 h to immobilize the PNA on the electrode surface. The PSA-antibody was reacted with an EDC/NHS mixture for 1 h and the excess free EDC/NHS in the PSA-antibody solution was removed with a Millipore YM-30 concentrator. Then the PNA modified electrode was immersed into the PSA-antibody solution overnight to anchor the PSA-antibody to the PNA terminal amino group. GOx was reacted with an EDC/NHS mixture for 1 h and then mixed with PSA (1:1) overnight to form a PSA-GOx complex. Then the PNA/PSA-antibody modified gold electrode was immersed into the PSA-GOx solution for 1 h and it was then used as the PSA biosensor. FIG. 14 shows a schematic illustration of the fabrication process of the PSA biosensor. The gold NEEs were also used to fabricate PSA biosensor and the process is the same with gold disc electrode.

Detection of PSA and regeneration—The PSA biosensor was immersed into the PSA analyte solution (or serum sample) for 15 min to allow PSA to displace the PSA-GOx complex due to the different affinities. The electrochemical change was then recorded. After the detection of PSA, the PSA biosensor was regenerated by using a glycine.HCl (pH 2.5) solution to break the antigen-antibody binding. The detection and regeneration processes are also shown in FIG. 14.

Electrochemical measurements—Electrochemical experiments were performed on an Epsilon Electrochemical Workstation from BASi. The electrochemical measurements were carried out in a three electrode cell with the modified gold electrodes as working electrodes, an Ag/AgCl electrode as reference electrode and a platinum wire electrode as the auxiliary electrode. All the measurements were carried out in $N_2$-saturated phosphate buffer (pH 7.5).

Surface plasmon resonance (SPR)—SPR experiments were performed with a BIAcore 3000 instrument and the affinities were calculated by the BIAevaluation software (Version 4.1, BIAcore). Buffer solutions used in all experiments were filtered and degassed. The PSA antibody was coupled to carboxymethylated dextran matrix (CM5) chips following the manufacturer's instructions. Briefly, the CM5 chip was activated by a freshly mixed solution containing 0.2 M EDC and 0.05 M NHS. Then the PSA antibody at 10 μg/ml in 10 mM sodium acetate (pH 4.5) was flowed over the activated chip surface and immobilized. Finally, 1M ethanolamine-HCl (pH 8.5) was injected to block unreacted sites on the chip surface. The affinity study of PSA or enzyme labeled PSA to PSA antibody was carried out with different concentrations of analytes. Glycine.HCl (pH 2.5) solution was used as the regeneration buffer.

Results and Discussion

Figure 15B:
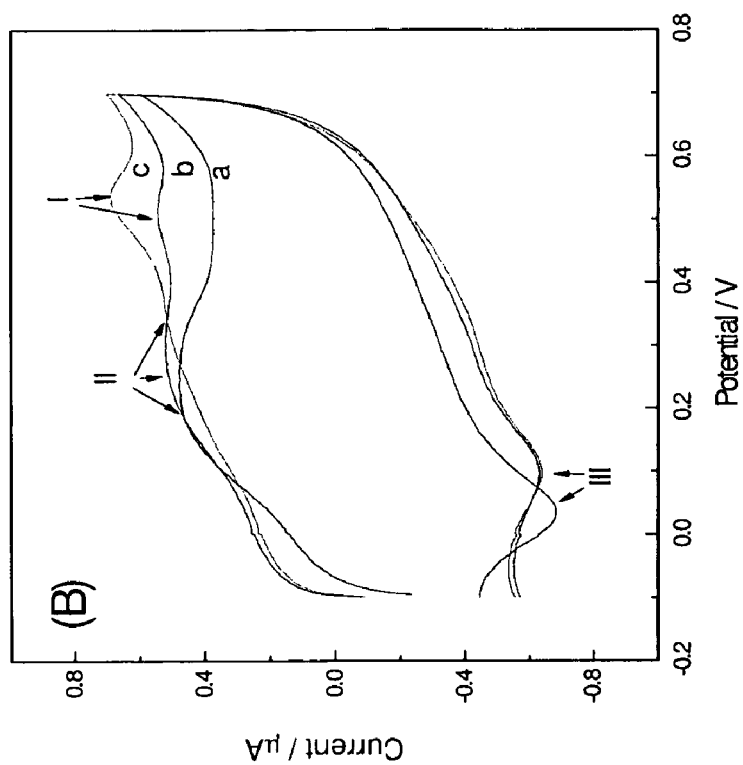
FIG. 15B shows CV curves of the differently modified gold NEEs in phosphate buffer (pH 7.5) at 0.1 V s$^{-1}$: (a) PNA/PSA-antibody modified gold electrode; (b) PNA/PSA-antibody/PSA-GOx modified electrode; and (c) the PNA/PSA-antibody/PSA-GOx modified electrode after incubation in 0.4 ng mL$^{-1}$ PSA solution, for the experiments described in Example 5.
Figure 15A:
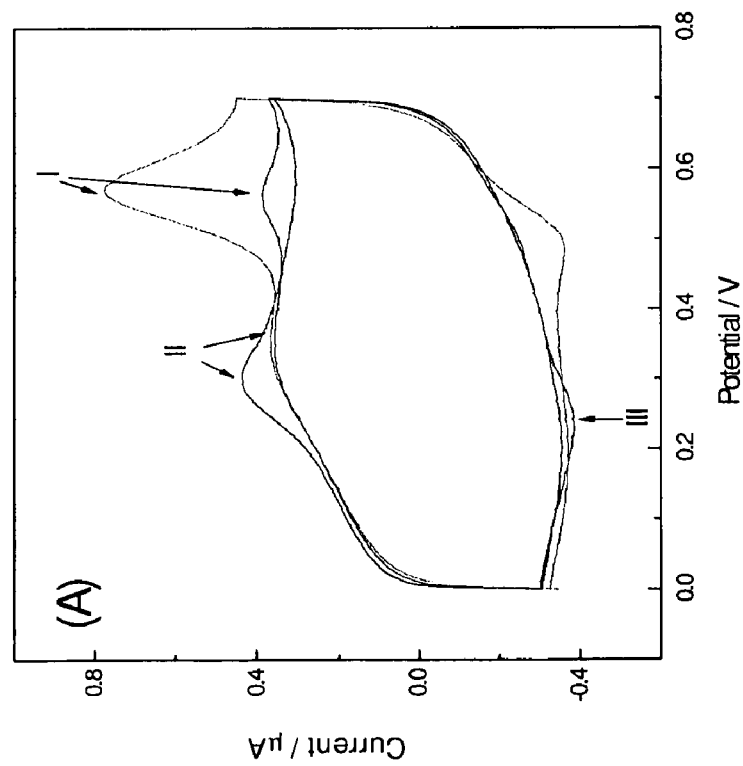
FIG. 15A shows CV curves of the differently modified gold disc electrodes in phosphate buffer (pH 7.5) at 0.1 V s$^{-1}$: (a): PNA/PSA-antibody modified electrode; (b): PNA/PSA-antibody/PSA-GOx modified electrode; (c): the PNA/PSA-antibody/PSA-GOx modified electrode after incubation in 1.0 ng mL$^{-1}$ PSA solution, for the experiments described in Example 5.

Electrochemical characteristics of the modified electrodes—Cyclic voltammetry (CV) curves of the modified gold disc electrodes (FIG. 15A) and gold NEEs (FIG. 15B) with the PNA (8hqR-$Cu^{2+}$) as the linker in phosphate buffer (pH 7.5) displays distinct redox peaks (FIGS. 15A and 15B). As shown in FIG. 15A curve a, redox peaks (II and III) corresponding to $Cu^{+/2+}$ metal ions bound in the PNA are observed in the PNA/PSA-antibody modified gold disc electrode. Another anodic peak (I) is observed for the PNA/PSA-antibody/PSA-GOx modified gold disc electrode, verifying the electroactive state of the assembly and immobilization of the various components on the electrode surface. Incubation of the PNA/PSA-antibody/PSA-GOx modified electrode in a solution containing free PSA, the anodic peak current signal (peak I) decreases due to disruption of GOx-PSA from the PSA antibody by free PSA in solution (shown as curve c in FIG. 15A). Displacement by free PSA is anticipated, due to the higher affinity of PSA to PSA-antibody compared to the affinity of the GOx-PSA complex. The affinities of PSA to PSA-antibody ($7.01 \times 10^{-10}$ M) and PSA-GOx complex ($1.82 \times 10^{-8}$ M) to PSA-antibody were obtained through SPR experiments. Similar to the PSA biosensor based on the gold disc electrode, the redox peaks of $Cu^{+/2+}$ bound to the PNA (shown peaks II and III in FIG. 15B) were also observed at the PNA/PSA-antibody modified gold NEE. After binding with PSA-GOx complex, the anodic peak (I) of the PSA-GOx complex was observed (shown as curve b in FIG. 15B). Moreover, the peak current (I) of PSA-GOx complex decreased after the incubation of the PNA/PSA-antibody/PSA-GOx modified gold NEE in the PSA solution (shown as curve c in FIG. 15B). It also indicates that the PSA-GOx complexes are partially displaced by PSA leading to the decrease of the anodic peak current. Moreover, a shift of peak potential of $Cu^{+/2+}$ (peaks II and III in FIGS. 15A and 15B) together with a decrease of the peak current was observed, which may be due to leakage of Cu ion from the electrode surface.

In addition, the surface coverage concentration (Γ) of the PSA-GOx complex on the electrode surface can be estimated according to the Cottrell equation ($I_p=n^2F^2v A\Gamma/4RT$, $I_P$: the peak current; n: number of electrons transferred/molecule; F: Faraday's constant; v: scan rate; A: electrode area; R: the gas constant; T: the temperature). The average surface coverage of the PSA-GOx on the gold disc electrode and gold NEE surface were calculated to be $3.9 \times 10^{-11}$ mol $cm^{-2}$ and $3.3 \times 10^{-11}$ mol $cm^{-2}$ respectively. Moreover, the electron transfer rate of the different PSA biosensors can be calculated using the method described previously (Xiao Y, Patolsky F, Katz E, Hainfeld J F, Willner I. Plugging into enzymes: nanowiring of redox enzymes by a gold nanoparticle. *Science.* 2003, 299, 1877-1881). The electron transfer rate constants of the PSA biosensors base on gold disc electrode and gold NEE were approximately 2.3 and 5.4 $s^{-1}$ respectively.

Figure 16A:
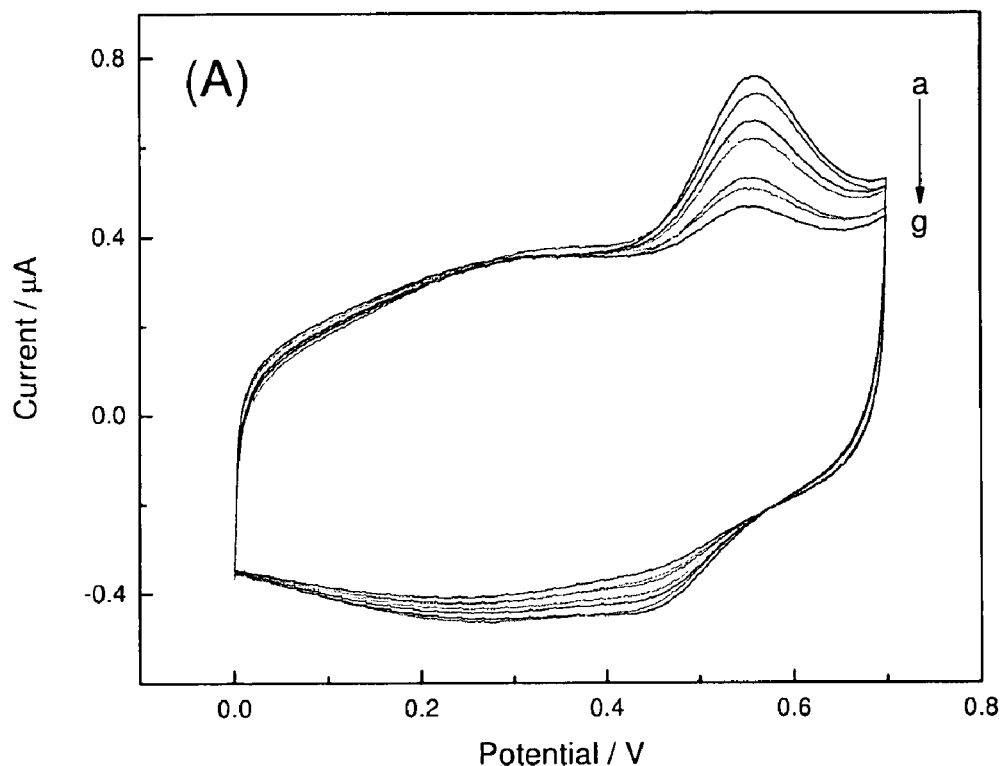
FIG. 16A shows responses of the PSA biosensor based on gold disc electrode after incubation in 0.0, 0.1, 0.2, 0.4, 0.6, 0.8 and 10.0 ng mL$^{-1}$ PSA solution (from curve a to curve g), for the experiments described in Example 5.
Figure 16B:
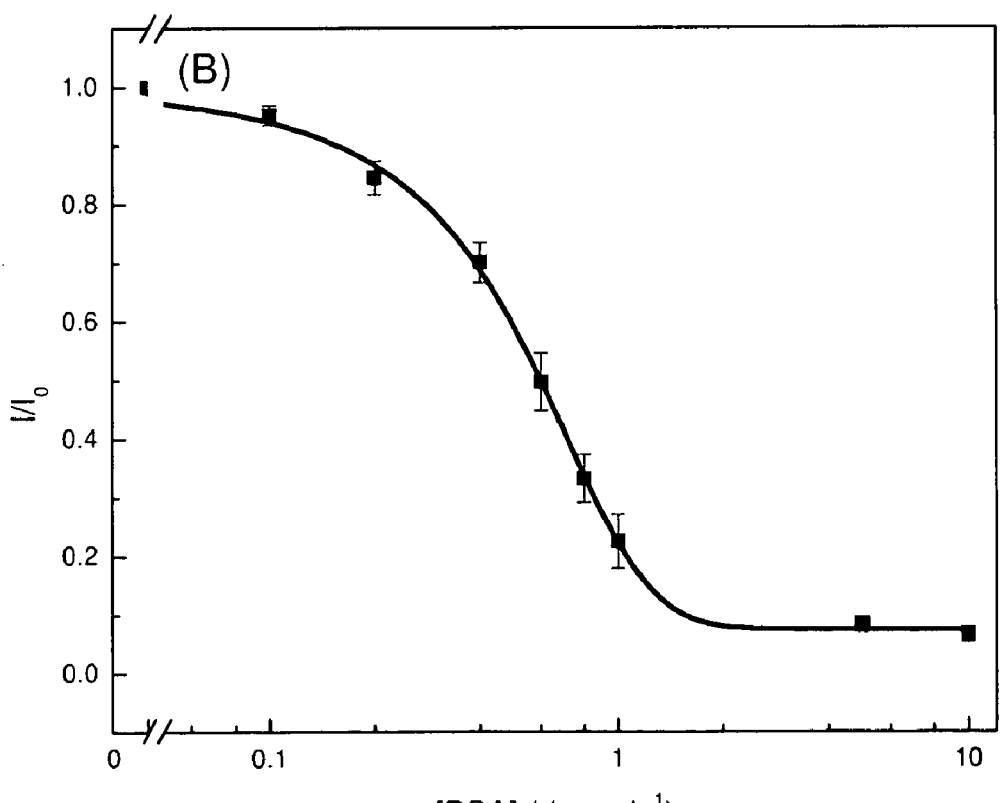
FIG. 16B shows the dependence of the decrease of anodic current on the PSA concentrations, for the experiments described in Example 5. The error bars indicate the R.S.D. of five replicative measurements (n=5).

Analytical performance of the PSA biosensor—Using PSA-GOx complex as the signaling molecule for the competitive reaction with PSA, the detection range of the PSA biosensor was determined using standard concentrations of PSA solutions. The response of the PSA biosensor, based on a gold disc electrode, to different concentrations of PSA solutions were measured (FIG. 16A), where the peak currents decreased after the PSA-GOx complex was displaced by the PSA gradually. The electrochemical current signal changes were plotted as a function of PSA concentration, shown in FIG. 16B. A series of repetitive measurements were performed and showed a relative standard deviation (R.S.D.) of 8.6% (n=5). The electrochemical evaluation revealed that the peak current decreased with increasing PSA concentration. The dynamic detection range of the PSA biosensor is from 0.1 to 1 ng $mL^{-1}$ PSA. Concentrations above 1 ng $mL^{-1}$ PSA saturates the biosensor, as shown by a plateauing of current, indicating maximal displacement of the PSA-GOx complex bound to the PSA antibody immobilized on the electrode surface. The detection limit of PSA biosensor based on PNA/ PSA-antibody/PSA-GOx modified gold disc electrode was determined to be 0.1 ng $mL^{-1}$.

Figure 17A:
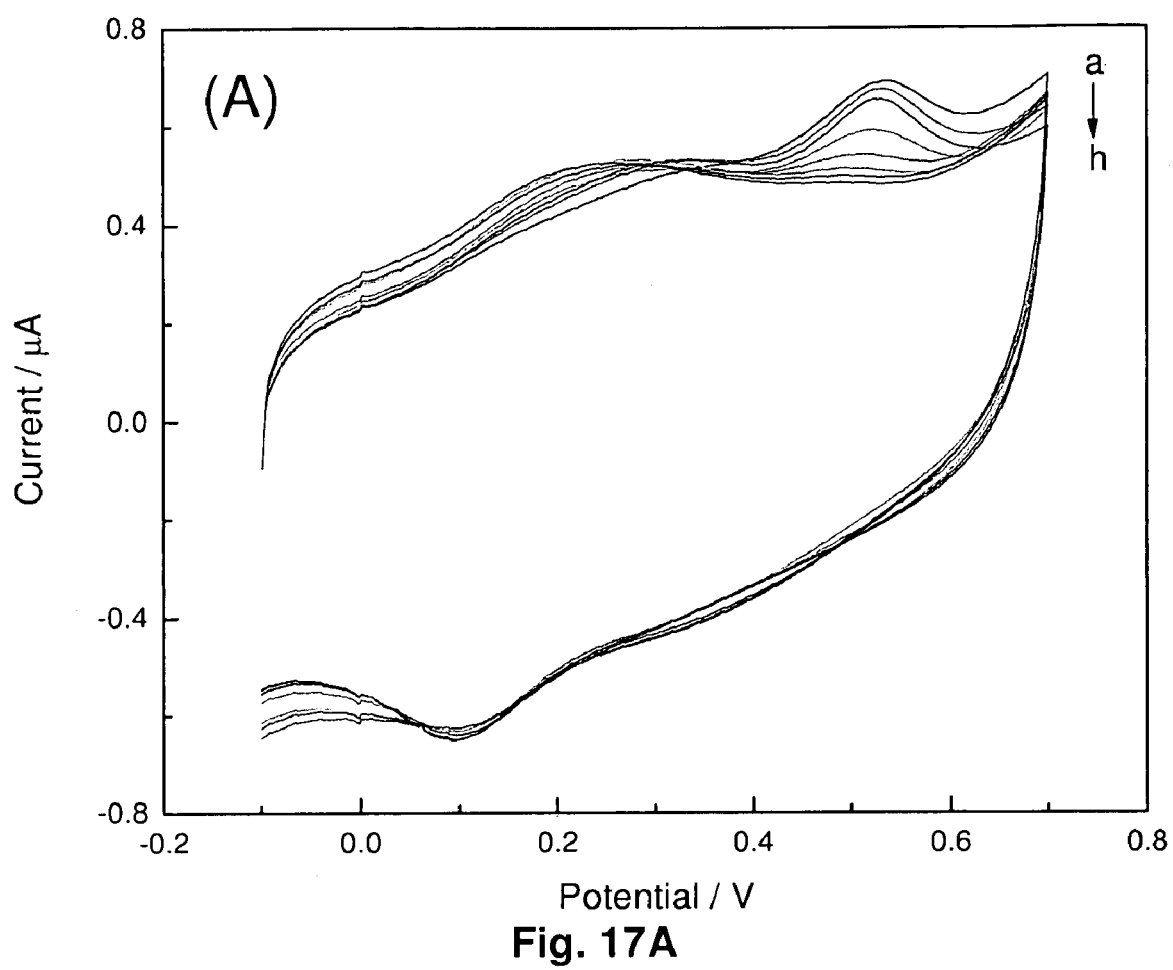
FIG. 17A shows the responses of the PSA biosensor based on gold NEE after incubation in 0.0, 0.05, 0.1, 0.2, 0.4, 0.6, 0.8 and 1.0 ng mL$^{-1}$ PSA solution (from curve a to curve h), for the experiments described in Example 5.
Figure 17B:
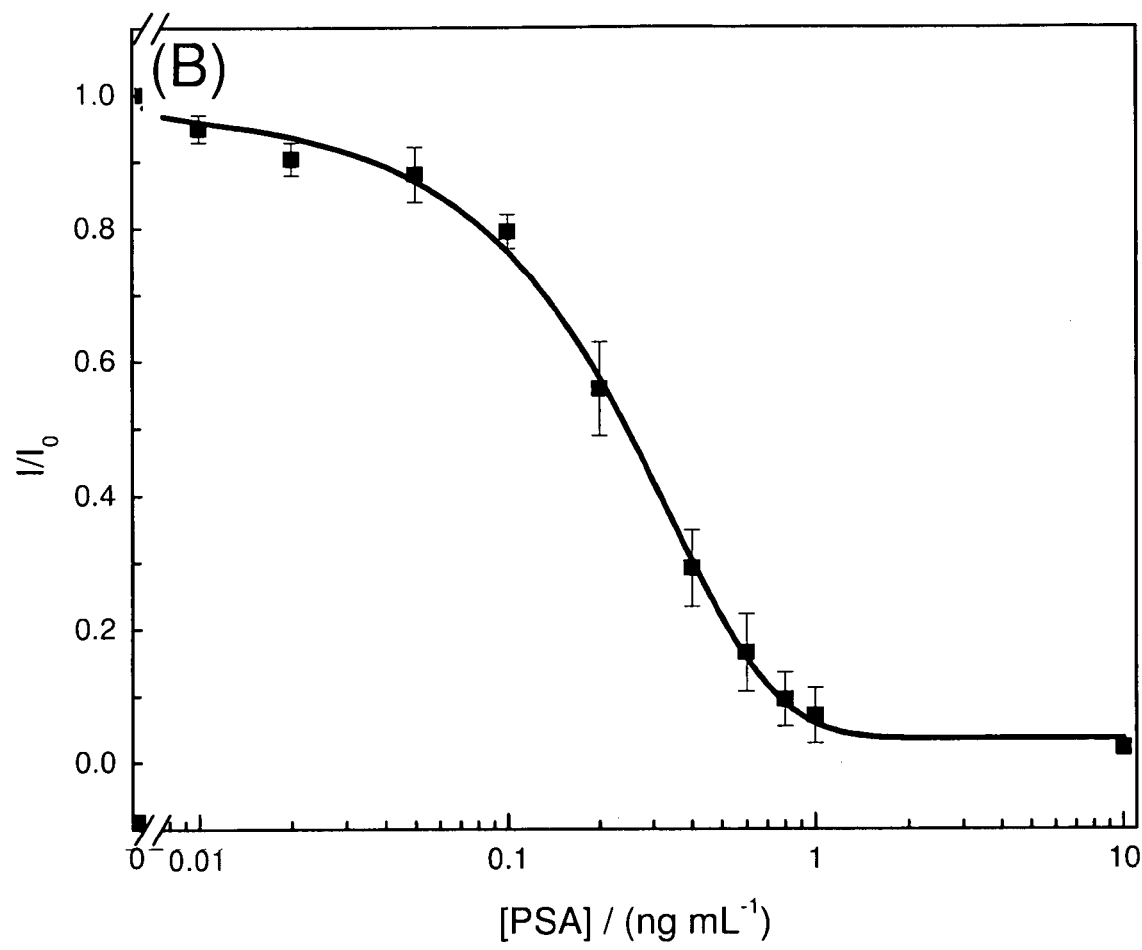
FIG. 17B shows the dependence of the decrease of anodic current on the PSA concentrations, for the experiments described in Example 5. The error bars indicate the R.S.D. of five replicative measurements (n=5).

PSA biosensors fabricated on gold NEEs display characteristic redox transitions, exhibiting dependency on free PSA concentrations in solution for current decreases (FIGS. 17A and 17B). The dynamic detection range of the PSA biosensor based on gold NEE is from 0.01 to 1 ng $mL^{-1}$ PSA, with a R.S.D. of 11.5% for five replicative measurements. Enhanced sensitivity was obtained using gold NEE, with a detection limit of 0.01 ng $mL^{-1}$, 10-fold lower than that of the PSA biosensor based on gold disc electrode. Optimization of sensitivity may be due to enhanced signal-to-noise current ratio using the nanoelectrode platform. Increased sensitivity of 2-3 orders of magnitude has been reported in other nanoelectrode platforms, relative to disc electrodes (Ugo P, Pepe N, Moretto L M, Battagliarin M. Direct voltammetry of cytochrome c at trace concentrations with nanoelectrode ensembles. *J. Electroanal. Chem.* 2003, 560, 51-58). The highest sensitivity for electrochemical detection of PSA is 4 pg $mL^{-1}$; our detection limit of 10 pg $mL^{-1}$ is among the lowest reported (Table 7).

TABLE 7

The comparison of detection limit with the literatures.

| Electrochemical Biosensor | Detection Limit | Refs |
|---|---|---|
| PNA/PSA-antibody/PSA-GOx modified gold NEE | 0.01 ng $mL^{-1}$ | Herein |
| PNA/PSA-antibody/PSA-GOx modified gold disc eletrode | 0.1 ng $mL^{-1}$ | Herein |
| A sandwich immunoassay | 3.0 ng $mL^{-1}$ | a |
| A sandwich immunoassay | 3.0 ng $mL^{-1}$ | b |
| A sandwich immunoassay based single-wall carbon nanotube forest platforms and secondary antibody-nanotube bioconjugates | 4 pg $mL^{-1}$ | c |
| Single-walled carbon nanotubes modified microelectrode arrays | 0.25 ng/mL | d |
| Peptide modified gold NEE with Ru(III)/Fe(III) | 1 pM (~0.03 ng $mL^{-1}$) | e |
| PSA-antibody/gold colloids/alumina sol-gel film modified gold electrode | 3.4 ng $mL^{-1}$ | f |
| A sandwich immunoassay based on multiwall carbon nanotubes modified glassy carbon electrode | 0.08 ng $mL^{-1}$ | g |
| A sandwich immunoassay with CdSe@ZnS nanoparticles as signal-amplifier vehicle | 0.02 ng $mL^{-1}$ | h |
| A sandwich immunoassay with functionalized silica nanoparticles as tracer | 0.76 ng $mL^{-1}$ | i |
| Phenylboronic acid monolayer/HPR-conjugated PSA-antibody modified gold electrode | 1.1 ng $mL^{-1}$ | j | a Sarkar P, et al. International Journal Pharmaceutics. 2002, 238, 1-9.
b Fernández-Sánchez C, et al. Anal. Chem. 76 (2004), 5649-5656.
c Yu X, et al. J. Am. Chem. Soc. 2006, 128, 11199-11205.
d Okuno J, et al. Biosen. Bioelectron. 2007, 22, 2377-2381.
e Roberts M A, et al. J. Am. Chem. Soc. 2007, 129, 11356-11357.
f Liu Y. Thin Solid Films. 2008, 8, 1803-1808.
g Panini N V, et al.. Biosen. Bioelectron. 2008, 7, 1145-1151.
h Lin Y Y, et al. Biosen. Bioelectron. 2008, 23, 1659-1665.
i Qu B, et al. Talanta. 2008, 76, 785-790
j Liu S Q, et al. Clin. Chim. Acta. 2008, 395, 51-56.

Figure 18:
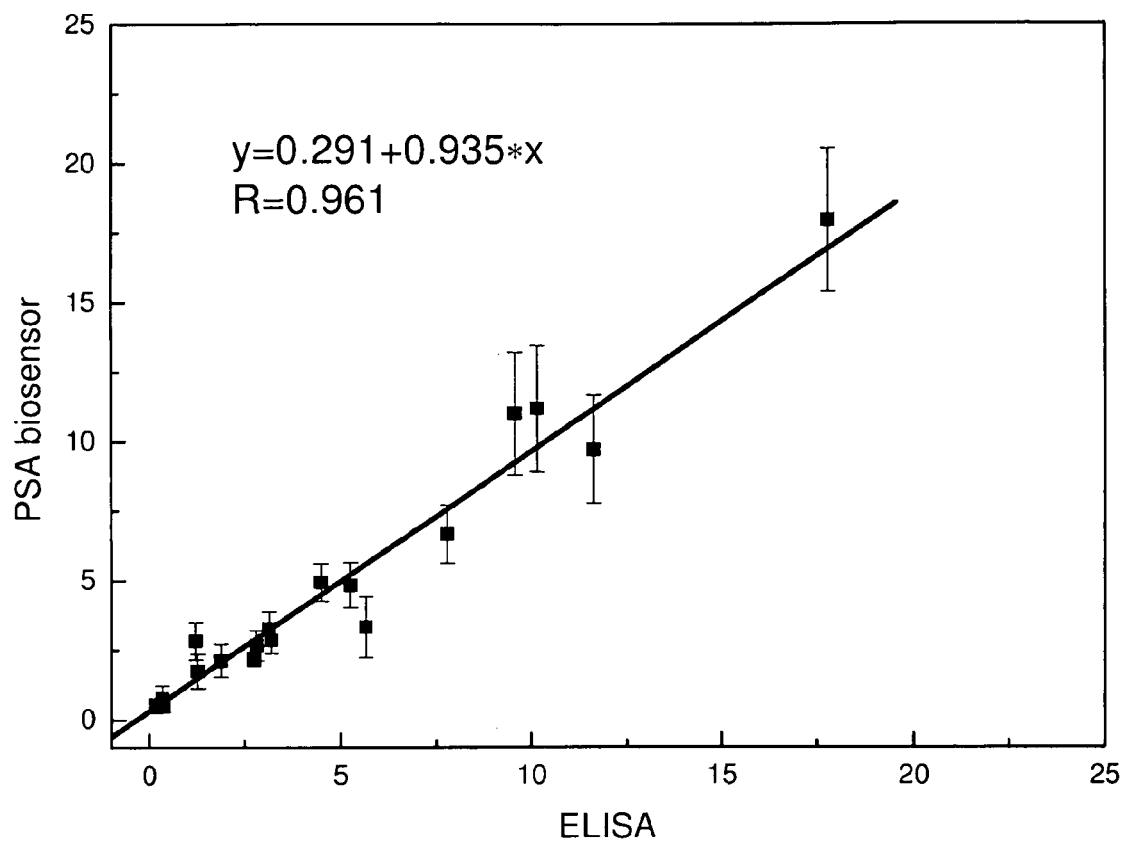
FIG. 18 shows a correlation between the PSA biosensor and ELISA method for the experiments described in Example 5.

Evaluation of clinical samples—To investigate the utility of the PSA biosensors for clinical analysis, 18 serum specimens were examined by both the PSA biosensors and the ELISA method. Prior to measurements using the PSA biosensors, clinical serum samples were diluted to keep the PSA concentration within the linear range of the biosensor. Comparison of the PSA biosensor values with ELISA results for the quantification of PSA shows that these agree well within the R.S.D of the measurements (Table 8) and linear regression analysis (y=0.291+0.935×($R^2$=0.961) (y-axis, PSA biosensor; x-axis, ELISA)) further signify this. FIG. 18 also shows the correlation between the PSA biosensor and ELISA method.

TABLE 8

Statistical Analysis of PSA Biosensor Results on Clinical Serum Samples (n = 10).

| Sample | ELISA (ng $mL^{-1}$) | PSA biosensor (ng $mL^{-1}$) | | |
|---|---|---|---|---|
| | | Mean | R.S.D. | CV % |
| 1 | 3.137 | 3.270 | 0.613 | 18.752 |
| 2 | 17.784 | 17.943 | 2.574 | 14.344 |
| 3 | 11.635 | 9.714 | 1.956 | 20.133 |
| 4 | 1.231 | 2.826 | 0.673 | 23.806 |
| 5 | 7.780 | 6.666 | 1.045 | 15.671 |
| 6 | 2.819 | 2.670 | 0.539 | 20.203 |
| _7_ | 0.343 | _0.735_ | _0.474_ | 64.491 |
| 8 | 1.287 | 1.735 | 0.629 | 36.276 |
| _9_ | 0.391 | _0.500_ | _0.261_ | 52.264 |
| 10 | 3.193 | 2.854 | 0.480 | 16.820 |
| 11 | 5.246 | 4.830 | 0.807 | 16.715 |
| 12 | 1.893 | 2.118 | 0.590 | 27.840 |
| 13 | 10.159 | 11.180 | 2.271 | 20.309 |
| 14 | 9.569 | 10.996 | 2.211 | 20.100 |
| 15 | 4.482 | 4.927 | 0.676 | 13.712 |
| 16 | 2.746 | 2.161 | 0.260 | 12.019 |
| 17 | 5.654 | 3.321 | 1.091 | 32.862 |
| _18_ | 0.186 | _0.500_ | _0.267_ | 53.390 | female controls underlined

Conclusions—We have fabricated a PSA biosensor coupling the redox enzyme GOx with a PSA antibody PNA to enable electrochemical quantitation of PSA in solution. Enhancement of sensitivity is due to nano-linker between the gold electrode surface and PSA-antibody. Based on a competitive reaction between free PSA and GOx-PSA on gold NEEs platforms, the detection limit of the PSA biosensor was enhanced to 0.01 ng $mL^{-1}$, which is highly competitive compared to other electrochemical PSA biosensors. The PSA biosensors accurately quantitated amounts of PSA in clinic serum and urine samples.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present application and the disclosure provided herein. Deference is to be given to definitions, descriptions, wording, language, data, statements, etc. provided in the present document where any material disclosed in such incorporated references, to include definitions, descriptions, data and statements, conflicts with material provided in the present application.

We claim:

1. A biosensor electrode assembly comprising a metalized peptide nucleic acid or peptide spacer linked to a conductive substrate and an anti-prostate specific antigen (PSA) binding reagent bound to a redox tag comprising PSA linked to a redox enzyme.

2. The biosensor of claim 1, in which the conductive substrate is gold.

3. The biosensor of claim 1, wherein the redox enzyme is chosen from one of NADH peroxidase, glucose oxidase, alkaline phosphatase and horseradish peroxidase.

4. The biosensor of claim 1, wherein the spacer comprises one or more metal-binding groups.

5. The biosensor of claim 4, wherein the one or more metal-binding groups is chosen from one or more of pyridine, bipyridine, porphyrin, and hydroxyquinoline groups.

6. The biosensor of claim 4, wherein the metal-binding group comprises a coordinated metal ion.

7. The biosensor of claim 1, wherein the peptide nucleic acidspacer is linked to a nanoelectrode.

8. The biosensor of claim 7, wherein the nanoelectrode is chosen from one or more of a nanowire of gold, copper, carbon, tin, silver, platinum, palladium, indium, tin oxide ITO or combinations thereof, a carbon nanotube, and a silicon nanotube.

9. A method of detecting or quantifying PSA in a sample comprising contacting the sample with a biosensor electrode assembly comprising a metalized peptide nucleic acid or peptide spacer linked to a conductive substrate and an anti-prostate specific antigen (PSA) binding reagent bound to a redox tag comprising PSA linked to a redox enzyme, and determining if, or the extent of which, a signal from the biological signal source is changed in the presence of the sample as indicative of the presence of PSA in the sample.

10. The method of claim 9, wherein displacement of the redox tag by PSA in the sample alters electron transfer rates through the spacer.

11. The biosensor of claim 1, wherein the conductive substrate is selected from the group consisting of an electrode, a nanoelectrode and a nanoelectrode needle.

12. The biosensor of claim 1, comprising an anti-PSA binding reagent linked to a nanoelectrode by a metallized polypeptide.

13. The biosensor of claim 12, wherein the anti-PSA binding reagent is bound to a redox tag comprising a PSA antigen linked to a redox enzyme.

14. The biosensor of claim 13, wherein the redox enzyme is glucose oxidase.

15. The biosensor of claim 1, comprising a plurality of metalized peptide nucleic acid or peptide spacers each linked to the conductive substrate and an anti-PSA binding reagent bound to a redox tag comprising PSA linked to a redox enzyme.

16. The method of claim 9, wherein the redox enzyme is one of NADH peroxidase, glucose oxidase, alkaline phosphatase and horseradish peroxidase.

17. The method of claim 9, wherein the redox enzyme is glucose oxidase.

18. The method of claim 9, wherein the spacer comprises one or more metal-binding groups.

19. The method of claim 18, wherein the one or more metal-binding groups is selected from the group consisting of pyridine, bipyridine, porphyrin, and hydroxyquinoline groups.

20. The method of claim 18, wherein the metal-binding group comprises a coordinated metal ion.

21. The method of claim 9, in which the conductive substrate is gold.

22. The method of claim 9, wherein the spacer is linked to a nanoelectrode.

23. The method of claim 22, wherein the nanoelectrode is selected from the group consisting of one or more of a nanowire of gold, copper, carbon, tin, silver, platinum, palladium, indium tin oxide (ITO) or combinations thereof, a carbon nanotube, and a silicon nanotube.

24. The method of claim 9, the biosensor electrode assembly comprising a plurality of metalized peptide nucleic acid or peptide spacers each linked to the conductive substrate and an anti-prostate serum antigen binding reagent bound to a redox tag comprising prostate serum antigen (PSA) linked to a redox enzyme.

25. The method of claim 9, in which the conductive substrate is selected from the group consisting of an electrode, a nanoelectrode and a nanoelectrode needle.

* * * * *

UNITED STATES PATENT AND TRADEMARK OFFICE
CERTIFICATE OF CORRECTION

| | | |
|---|---|---|
| PATENT NO. | : 8,198,039 B2 | Page 1 of 1 |
| APPLICATION NO. | : 12/204407 | |
| DATED | : June 12, 2012 | |
| INVENTOR(S) | : Haibin Shi et al. | |

It is certified that error appears in the above-identified patent and that said Letters Patent is hereby corrected as shown below:

IN THE CLAIMS:

Column 36, Lines 11-12, Claim 7, delete "wherein the peptide nucleic acidspacer" and insert -- wherein the spacer --

Column 36, Line 15, Claim 8, "indium, tin oxide ITO" should read -- indium tin oxide ITO --

Signed and Sealed this
Second Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,198,039 B2  
APPLICATION NO. : 12/204407  
DATED : June 12, 2012  
INVENTOR(S) : Haibin Shi et al.

It is certified that error appears in the above-identified patent and that said Letters Patent is hereby corrected as shown below:

Specification

Column 1, Lines 14-20, under the heading "STATEMENT REGARDING FEDERAL FUNDING", delete "The U.S. Government has a paid-up license in this invention and the right in limited circumstances to require the patent owner to license others on reasonable terms as provided for by the terms of Grant No. GM-66466 awarded by the National Institutes of Health and Grant No. F49620-03-1-0365 awarded by the Air Force Office of Scientific Research." and insert -- This invention was made with government support under grant number GM066466 awarded by the National Institutes of Health and grant number F49620-03-1-0365 awarded by the Air Force Office of Scientific Research. The government has certain rights in the invention. --

Signed and Sealed this  
Fifth Day of January, 2016

Michelle K. Lee  
*Director of the United States Patent and Trademark Office*